United States Patent
Fürstner et al.

(10) Patent No.: US 9,695,131 B2
(45) Date of Patent: Jul. 4, 2017

(54) SUBSTITUTED URACILS AS CHYMASE INHIBITORS

(71) Applicant: Bayer Pharma Aktiengesellschaft, Berlin (DE)

(72) Inventors: Chantal Fürstner, Mülheim/Ruhr (DE); Jens Ackerstaff, Düsseldorf (DE); Alexander Straub, Wuppertal (DE); Heinrich Meier, Wuppertal (DE); Hanna Tinel, Wuppertal (DE); Katja Zimmermann, Düsseldorf (DE); Dmitry Zubov, Remscheid (DE); Jens Schamberger, Velbert-Langenberg (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 15/034,995

(22) PCT Filed: Nov. 5, 2014

(86) PCT No.: PCT/EP2014/073800
§ 371 (c)(1),
(2) Date: May 6, 2016

(87) PCT Pub. No.: WO2015/067651
PCT Pub. Date: May 14, 2015

(65) Prior Publication Data
US 2016/0244415 A1   Aug. 25, 2016

(30) Foreign Application Priority Data

Nov. 8, 2013 (EP) ..................... 13192183

(51) Int. Cl.
| | | |
|---|---|---|
| *C07D 403/04* | (2006.01) | |
| *C07D 239/557* | (2006.01) | |
| *C07D 403/12* | (2006.01) | |
| *C07D 403/10* | (2006.01) | |
| *C07D 239/54* | (2006.01) | |
| *C07D 413/04* | (2006.01) | |
| *C07D 413/10* | (2006.01) | |
| *C07D 413/12* | (2006.01) | |
| *C07D 417/04* | (2006.01) | |
| *C07D 417/12* | (2006.01) | |
| *A61K 9/00* | (2006.01) | |
| *A61K 9/08* | (2006.01) | |
| *A61K 9/20* | (2006.01) | |
| *A61K 31/513* | (2006.01) | |
| *A61K 45/06* | (2006.01) | |
| *C07D 403/14* | (2006.01) | |
| *C07D 413/14* | (2006.01) | |
| *C07D 417/14* | (2006.01) | |

(52) U.S. Cl.
CPC ........ *C07D 239/557* (2013.01); *A61K 9/0053* (2013.01); *A61K 9/08* (2013.01); *A61K 9/20* (2013.01); *A61K 31/513* (2013.01); *A61K 45/06* (2013.01); *C07D 239/54* (2013.01); *C07D 403/04* (2013.01); *C07D 403/10* (2013.01); *C07D 403/12* (2013.01); *C07D 403/14* (2013.01); *C07D 413/04* (2013.01); *C07D 413/10* (2013.01); *C07D 413/12* (2013.01); *C07D 413/14* (2013.01); *C07D 417/04* (2013.01); *C07D 417/12* (2013.01); *C07D 417/14* (2013.01)

(58) Field of Classification Search
USPC ........................................ 514/269, 274, 393
See application file for complete search history.

(56) References Cited

U.S. PATENT DOCUMENTS 9,481,672 B2 * 11/2016 Furstner ............... C07D 413/14
2008/0090856 A1   4/2008 Flylnn et al.

FOREIGN PATENT DOCUMENTS

| EP | 0936216 | 8/1999 |
|---|---|---|
| JP | 10195063 | 7/1998 |
| WO | 96/33974 | 10/1996 |
| WO | 00/06568 | 2/2000 |
| WO | 00/06569 | 2/2000 |
| WO | 01/19355 | 3/2001 |
| WO | 01/19776 | 3/2001 |
| WO | 01/19778 | 3/2001 |
| WO | 01/19780 | 3/2001 |
| WO | 02/42301 | 5/2002 |
| WO | 02/070462 | 9/2002 |
| WO | 02/070510 | 9/2002 |
| WO | 03/095451 | 11/2003 |
| WO | 2007/120339 | 10/2007 |
| WO | 2007/150011 | 12/2007 |
| WO | 2008/056257 | 5/2008 |
| WO | 2008/103277 | 8/2008 |

(Continued)

OTHER PUBLICATIONS

Abdelaal, et al., "Synthesis of 1-[3-Methyl-2(3H)-benzazolon-5- or 6-yl]-4-{4-[cis-2-(2,4-dichlorophenyl)-2-(1H-imidazol-l-yl-methyl)-1,3-dioxolan-4-yl]methyleneoxyphenyl}piperazines", J. Heterocyclic Chem., 29, 1992, pp. 1069-1076.

(Continued)

*Primary Examiner* — Pancham Bakshi
(74) *Attorney, Agent, or Firm* — Morrison & Foerster LLP

(57) ABSTRACT

Substituted uracil derivatives of formula (I), processes for their preparation, their use alone or in combinations for the treatment and/or prophylaxis of diseases, and their use for preparing medicaments for the treatment and/or prophylaxis of diseases.

4 Claims, No Drawings

(56) References Cited

FOREIGN PATENT DOCUMENTS

| WO | 2009/049112 | 4/2009 |
|---|---|---|
| WO | 2009/156182 | 12/2009 |
| WO | 2010/019903 | 2/2010 |
| WO | 2013/074633 | 5/2013 |

OTHER PUBLICATIONS

Artico, et al., "Research on Compounds with Antiblastic Activity", Farmaco Sci. Ed. 179, 1969, 15 pages.
Bacani, et al., "Chymase: A New Pharmacologic Target in Cardiovascular Disease", Cardiology in Review, 14(4), Jul./Aug. 2006, pp. 187-193.
Dogrell, "Therapeutic Potential of Non-peptide Chymase Inhibitors", Expert Opin. Ther. Patents 18, 2008, pp. 485-499.
Fleming, "Signaling by the Angiotensin-Converting Enzyme", Circulation Research, Apr. 14, 2006, pp. 887-896.
Huang, et al., "Chymase is Upregulated in Diabetic Nephropathy: Implications for an Alternative Pathway of Angiotensin II-Mediated Diabetic Renal and Vascular Disease", Journal of the American Society of Nephrology, 14, 2003, pp. 1738-1747.
Hughes, "Progress in the Mitsunobu Reaction. A Review", Organic Preparations and Procedures International: The New Journal for Organic Synthesis, 28(2), 1996, pp. 127-164.
Hughes, "The Mitsunobu Reaction", Chapter 2, Organic Reactions, 42, 1992, pp. 335-656.
Jin, et al., "An Antiarrhythmic Effect of Chymase Inhibitor After Myocardial Infarction", Pharmacol. Exp. Ther. 309, 2004, pp. 409-417.
Jin, et al., "Beneficial effects of cardiac chymase inhibition during the acute phase of myocardial infarction", Life Sciences, 71, 2002, pp. 437-446.
Kovanen, et al., "Infiltrates of Activated Mast Cells at the Site of Coronary Atheromatous Erosion or Rupture in Myocardial Infarction", Circulation, 92(5), Sep. 1, 1995, pp. 1084-1088.
Libby, et al., "Mast Cells as Mediators and Modulators of Atherogenesis", Circulation 115, 2007, pp. 2555-2558.
Lucero, et al., "Synthesis and anti-HSV-1 activity of quinolonic acyclovir analogues", Bioorganic & Medicinal Chemistry Letters, 16, 2006, pp. 1010-1013.
Matusumoto, et al., "Chymase Inhibition Prevents Cardiac Fibrosis and Improves Diastolic Dysfunction in the Progression of Heart Failure", Circulation, May 27, 2003, pp. 2555-2558.
McPherson, et al., "Chymase-like Angiotensin II-Generating Activity in End-Stage Human Autosomal Dominant Polycystic Kidney Disease", Journal of the American Society of Nephrology, 15, 2004, pp. 493-500.
Miyazaki, et al., "Pathological roles of angiotensin II produced by mast cell chymase and the effects of chymase inhibition in animal models", Pharmacology & Therapeutics, 112, 2006, pp. 668-676.
Mulvany, et al., "Contractile Properties of Small Arterial Resistance Vessels in Spontaneously Hypertensive and Normotensive Rats", Circulation Research, 41(1), Jul. 1977, pp. 19-26.
Senda, et al., "Pyrimidine Derivatives and Related Compounds. XVI.1) Synthesis of 1,3-Disubstituted5-Cyanouracil Derivatives and Related Compounds", Chem. Pharm. Bull., vol. 20(7), 1972, pp. 1380-1388.
Shiota, et al., "Cardiac mast cells in the transition to heart failure: innocent bystanders or key actors?", Journal of Hypertension, 21, 2003, pp. 1823-1825.
Stabile, et al., "Mild, convenient and versatile Cu-mediated synthesis of N-aryl-2-imidazolidinones", Tetrahedron Letters, 51(24), 2010, pp. 3232-3235.
Takai, et al., "An Orally Active Chymase Inhibitor, BCEAB, Supresses Heart Chymase Activity in the Hamster", Japanese Journal of Pharmacology, 86, 2001, pp. 124-126.
Van Henegouwen, et al., "First Total Synthesis of ent-Gelsedine via a Novel Iodide-Promoted Allene N-Acyliminium Ion Cyclization", Journal of Organic Chemistry, 65(24), 2000, pp. 8317-8325.
Zanini, et al., "Chymase-positive mast cells play a role in the vascular component of airway remodeling in asthma", Journal of Allergy Clinical Immunology, 120(2), Aug. 2007, pp. 329-333.
International Bureau of WIPO, International Preliminary Report on Patentability (with English translation) for International Patent Application No. PCT/EP2014/073800, May 10, 2016, 7 pages.
European Patent Office, International Search Report (with English translation) for International Patent Application No. PCT/EP2014/073800, Dec. 12, 2014, 5 pages.
European Patent Office, Written Opinion (with English translation) for International Patent Application No. PCT/EP2014/073800, May 14, 2015, 13 pages.

\* cited by examiner

SUBSTITUTED URACILS AS CHYMASE INHIBITORS

CROSS-REFERENCE TO RELATED APPLICATIONS

This application is a U.S. national phase application of International Patent Application No. PCT/EP2014/073800, filed Nov. 5, 2014 and titled SUBSTITUTED URACILS AS CHYMASE INHIBITORS, which claims priority to European Patent Application No. 13192183.5, filed Nov. 8, 2013 and titled SUBSTITUTED URACILS AS CHYMASE INHIBITORS, the contents of both of which are incorporated herein by reference in their entirety.

The present application relates to novel substituted uracil derivatives, to processes for their preparation, to their use alone or in combinations for the treatment and/or prophylaxis of diseases, and to their use for preparing medicaments for the treatment and/or prophylaxis of diseases.

Chymase is a chymotrypsin-like serine protease which is stored as a macromolecular complex with heparin proteoglycans in secretory vesicles of mast cells. After activation of the mast cells, chymase is released into the extracellular matrix and activated.

Activated mast cells play an important role in healing wounds and in inflammation processes, for example fibrosis of wounds, angiogenesis and cardiac remodelling (Miyazaki et al., *Pharmacol. Ther.* 112 (2006), 668-676; Shiota et al., *J. Hypertens.* 21 (2003), 1823-1825). An increase in the number of mast cells has been observed in the event of heart failure, myocardial infarction and ischaemia, in human atherosclerotic plaques and in abdominal aortic aneurysms (Kovanen et al., *Circulation* 92 (1995), 1084-1088; Libby and Shi, *Circulation* 115 (2007), 2555-2558; Bacani and Frishman, *Cardiol. Rev.* 14(4) (2006), 187-193). Chymase-positive mast cells can also play an important role in the vascular remodelling of the respiratory pathways in the event of asthma and chronic obstructive pulmonary disease. An increased number of mast cells has been found in endobronchial biopsies of asthma patients (Zanini et al., *J. Allergy Clin. Immunol.* 120 (2007), 329-333). Moreover, chymase is suspected of being partly responsible for the genesis of many renal disorders, such as diabetic nephropathy and polycystic kidney disease (Huang et al., *J. Am. Soc. Nephrol.* 14(7) (2003), 1738-1747; McPherson et al., *J. Am. Soc. Nephrol.* 15(2) (2004), 493-500).

Chymase is predominantly involved in the production of angiotensin II in the heart, in the artery wall and in the lung, whereas the angiotensin-converting enzyme is responsible for the formation of the peptide in the circulation system (Fleming I., *Circ. Res.* 98 (2006), 887-896). In addition, chymase cleaves a number of other substrates of pathological significance. Chymase leads to degradation of extracellular matrix proteins, such as fibronectin, procollagen and vitronectin, and to the breakoff of focal adhesions. It brings about activation and release of TGFβ from its latent form, which plays an important role in the genesis of cardiac hypertrophy and cardiac fibrosis. The enzyme has atherogenic action, by degrading apolipoproteins and preventing the absorption of cholesterol by HDL. The action of chymase leads to release and activation of the cytokine interleukin 1 with its pro-inflammatory properties. Furthermore, it contributes to production of endothelin 1 (Bacani and Frishman, *Cardiol. Rev.* 14(4) (2006), 187-193). An accumulation of chymase-positive mast cells has been found in biopsies of patients having atopic dermatitis, Crohn's disease, chronic hepatitis and hepatic cirrhosis, and also idiopathic interstitial pneumonia (Dogrell S. A., *Expert Opin. Ther. Patents* 18 (2008), 485-499).

The possibility of using chymase inhibitors for the treatment of different diseases has been demonstrated in numerous studies involving animal experimentation. Inhibition of chymase can be useful for the treatment of myocardial infarction. Jin et al. (*Pharmacol. Exp. Ther.* 309 (2004), 409-417) showed that a ligature of the coronary artery in dogs led to ventricular arrhythmias and elevated production of angiotensin II and chymase activity in the heart. Intravenous administration of the chymase inhibitor TY-501076 reduced chymase activity and the angiotensin II concentration in the plasma, and suppressed the occurrence of arrhythmias. A positive effect of chymase inhibition was shown in an in vivo model for myocardial infarction in hamsters. Treatment of the animals with the chymase inhibitor BCEAB reduced chymase activity, improved haemodynamics and reduced mortality (Jin et al., *Life Sci.* 71 (2002), 437-446). In the cardiomyopathic Syrian hamster, where the number of mast cells in the heart is elevated, oral treatment of the animals with the chymase inhibitor reduced cardiac fibrosis by 50% (Takai et al., *Jpn. J. Pharmacol.* 86 (2001), 124-126). In a tachycardia-induced heart failure model in dogs, chymase inhibition with SUN-C82257 led to reduction in the number of mast cells and in fibrosis in the heart. In addition, the diastolic function of the heart was improved after the treatment (Matsumoto et al., *Circulation* 107 (2003), 2555-2558).

Inhibition of chymase thus constitutes an effective principle in the treatment of cardiovascular disorders, inflammation and allergic disorders, and various fibrotic disorders.

WO 2007/150011 and WO 2009/049112 disclose a process for preparing pyrimidinetriones with glycine substituents. WO 2008/056257 describes triazinediones as GABA-B receptor modulators for treatment of CNS disorders. WO 2008/103277 discloses various nitrogen heterocycles for treatment of cancer. WO 2009/156182 describes uracil derivatives for suppression or reduction of resistance development in the course of cytostatic treatment. JP10195063 describes uracil derivatives as leukotriene antagonists, WO 2013/074633 uracil derivatives as inhibitors of the tyrosine kinases AXL and c-MET.

It was an object of the present invention to provide novel substances which act as inhibitors of chymase and are suitable as such for treatment and/or prophylaxis of disorders, especially cardiovascular disorders.

The present invention relates to compounds of the general formula (I)

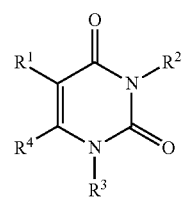

(I)

in which

R[1] represents cyano, 5- to 7-membered heterocyclyl or 5- or 6-membered heteroaryl,
  where 5- to 7-membered heterocyclyl may be substituted by 1 or 2 substituents independently of one another selected from the group consisting of oxo, $(C_1-C_4)$-alkyl and halogen, and
where 5- or 6-membered heteroaryl may be substituted by 1 or 2 substituents independently of one another selected from the group consisting of $(C_1-C_4)$-alkyl, hydroxy and halogen,
or
$R^1$ represents a group of the formula

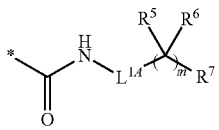

where
\* represents the point of attachment to the uracil group,
m represents 0 or 1,
$L^{1A}$ represents a bond or $(C_1-C_4)$-alkanediyl,
  in which $(C_1-C_4)$-alkanediyl may be substituted by 1 to 3 substituents independently of one another selected from the group consisting of fluorine, trifluoromethyl, $(C_1-C_4)$-alkyl, $(C_3-C_7)$-cycloalkyl, hydroxy and $(C_1-C_4)$-alkoxy,
$R^5$ represents hydrogen or $(C_1-C_4)$-alkyl,
$R^6$ represents hydrogen or $(C_1-C_4)$-alkyl,
  in which $(C_1-C_4)$-alkyl may be substituted by 1 or 2 substituents independently of one another selected from the group consisting of fluorine, trifluoromethyl, $(C_1-C_4)$-alkyl, hydroxy and $(C_1-C_4)$-alkoxy,
or
  $R^5$ and $R^6$ together with the carbon atoms to which they are attached form a 3- to 7-membered carbocycle,
$R^7$ represents hydrogen, cyano, $(C_3-C_7)$-cycloalkyl, hydroxycarbonyl or $(C_1-C_4)$-alkoxycarbonyl,
or
$R^1$ represents a group of the formula

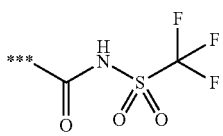

where
\*\*\* represents the point of attachment to the uracil group,
$R^2$ represents a group of the formula

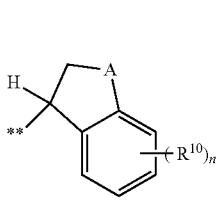 or 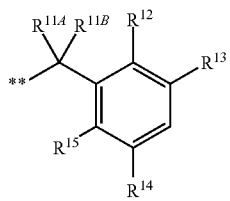

where
\*\* represents the point of attachment to the uracil nitrogen atom,
A represents $-CH_2-$, $-CH_2-CH_2-$, $-O-CH_2-\#\#$ or oxygen,
  in which ## represents the point of attachment to the phenyl ring,
n represents a number 0, 1 or 2,
$R^{10}$ represents hydrogen, halogen, difluoromethyl, trifluoromethyl, $(C_1-C_4)$-alkyl, difluoromethoxy, trifluoromethoxy or $(C_1-C_4)$-alkoxy,
$R^{11A}$ represents hydrogen or deuterium,
$R^{11B}$ represents hydrogen, deuterium or $(C_1-C_4)$-alkyl,
$R^{12}$ represents hydrogen, halogen, $(C_1-C_4)$-alkyl, difluoromethyl or trifluoromethyl,
$R^{13}$ represents halogen, $(C_1-C_4)$-alkyl, difluoromethyl or trifluoromethyl,
$R^{14}$ represents hydrogen or halogen,
$R^{15}$ represents hydrogen or halogen,
$R^3$ represents

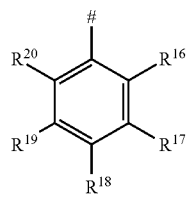

where
\# represents the point of attachment to the uracil nitrogen atom,
$R^{16}$ represents hydrogen,
$R^{17}$ represents hydrogen, halogen, $(C_1-C_4)$-alkyl or $(C_1-C_4)$-alkoxy,
$R^{18}$ represents $(C_1-C_4)$-alkyl, $(C_1-C_4)$-alkoxy, $(C_1-C_4)$-alkylthio, $(C_1-C_4)$-alkylsulfinyl, $(C_1-C_4)$-alkylsulfonyl or $-N(R^{21}R^{22})$,
  in which $(C_1-C_4)$-alkoxy may be substituted by a substituent independently of one another selected from the group consisting of hydroxy, $(C_1-C_4)$-alkoxycarbonyl, amino, mono-$(C_1-C_4)$-alkylamino, di-$(C_1-C_4)$-alkylamino, aminocarbonyl, mono-$(C_1-C_4)$-alkylaminocarbonyl and di-$(C_1-C_4)$-alkylaminocarbonyl,
where
$R^{21}$ represents $(C_1-C_4)$-alkyl, $(C_1-C_4)$-alkoxycarbonyl or $(C_1-C_4)$-alkylaminocarbonyl,
  in which $(C_1-C_4)$-alkylaminocarbonyl may be substituted by hydroxy or $(C_1-C_4)$-alkoxy,
$R^{22}$ represents hydrogen or $(C_1-C_4)$-alkyl,
or
$R^{18}$ represents 4- to 7-membered heterocyclyl or 5- to 6-membered heteroaryl,
  in which 4- to 7-membered heterocyclyl may be substituted by 1 to 3 substituents independently of one another selected from the group consisting of halogen, trifluoromethyl, $(C_1-C_4)$-alkyl, hydroxy, oxo, amino and $(C_1-C_4)$-alkoxycarbonyl,
    in which $(C_1-C_4)$-alkyl may be substituted by 1 or 2 substituents independently of one another selected from the group consisting of halogen, hydroxy and $-N(R^{23}R^{24})$,
      in which $R^{23}$ represents hydrogen, $(C_1-C_4)$-alkyl or $(C_1-C_4)$-alkylcarbonyl,
      in which $R^{24}$ represents hydrogen or $(C_1-C_4)$-alkyl,
  in which 5- to 6-membered heteroaryl may be substituted by 1 or 2 substituents independently of one another selected from the group consisting of halogen, trifluoromethyl, $(C_1-C_4)$-alkyl, hydroxy, amino and $(C_1-C_4)$-alkoxycarbonyl, in which $(C_1\text{-}C_4)$-alkyl may be substituted by 1 or 2 substituents independently of one another selected from the group consisting of halogen, hydroxy and —N($R^{23}R^{24}$),
  in which $R^{23}$ represents hydrogen, $(C_1\text{-}C_4)$-alkyl or $(C_1\text{-}C_4)$-alkylcarbonyl,
  in which $R^{24}$ represents hydrogen or $(C_1\text{-}C_4)$-alkyl,
$R^{19}$ represents hydrogen, halogen, cyano, $(C_1\text{-}C_4)$-alkyl or $(C_1\text{-}C_4)$-alkoxy,
$R^{20}$ represents hydrogen, halogen, $(C_1\text{-}C_4)$-alkyl or $(C_1\text{-}C_4)$-alkoxy,
or
$R^3$ represents

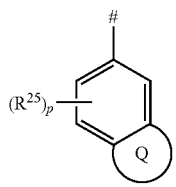

in which
represents the point of attachment to the uracil nitrogen atom,
the ring Q represents 5- to 7-membered heterocyclyl or 5- or 6-membered heteroaryl,
  in which 5- to 7-membered heterocyclyl may be substituted by 1 to 4 substituents independently selected from the group of halogen, difluoromethyl, trifluoromethyl, trideuteromethyl, $(C_1\text{-}C_6)$-alkyl, $(C_3\text{-}C_7)$-cycloalkyl, oxo, hydroxyl, $(C_1\text{-}C_4)$-alkylcarbonyl, $(C_1\text{-}C_4)$-alkoxycarbonyl, aminocarbonyl and $(C_1\text{-}C_4)$-alkylsulfonyl,
  in which 5- or 6-membered heteroaryl may be substituted by 1 to 2 substituents independently of one another selected from the group consisting of $(C_1\text{-}C_6)$-alkyl, $(C_3\text{-}C_7)$-cycloalkyl, hydroxy, $(C_1\text{-}C_4)$-alkylcarbonyl, $(C_1\text{-}C_4)$-alkoxycarbonyl, aminocarbonyl and $(C_1\text{-}C_4)$-alkylsulfonyl, and
  in which two $(C_1\text{-}C_6)$-alkyl radicals attached to a carbon atom of 5- to 7-membered heterocyclyl together with the carbon atom to which they are attached may form a 3- to 6-membered carbocycle,
$R^{25}$ represents halogen, $(C_1\text{-}C_4)$-alkyl or $(C_1\text{-}C_4)$-alkoxy,
p represents a number 0, 1, 2 or 3,
$R^4$ represents hydrogen or $(C_1\text{-}C_4)$-alkyl,
and the salts, solvates and solvates of the salts thereof.

The present invention relates to compounds of the general formula (I)
in which
$R^1$ represents cyano, 5- to 7-membered heterocyclyl or 5- or 6-membered heteroaryl,
  where 5- to 7-membered heterocyclyl may be substituted by 1 or 2 substituents independently of one another selected from the group consisting of oxo, $(C_1\text{-}C_4)$-alkyl and halogen,
  and
  where 5- or 6-membered heteroaryl may be substituted by 1 or 2 substituents independently of one another selected from the group consisting of $(C_1\text{-}C_4)$-alkyl, hydroxy and halogen,
or
$R^1$ represents a group of the formula

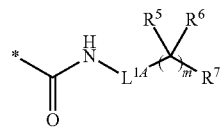

where
* represents the point of attachment to the uracil group,
m represents 0 or 1,
$L^{14}$ represents a bond or $(C_1\text{-}C_4)$-alkanediyl,
  in which $(C_1\text{-}C_4)$-alkanediyl may be substituted by 1 to 3 substituents independently of one another selected from the group consisting of fluorine, trifluoromethyl, $(C_1\text{-}C_4)$-alkyl, $(C_3\text{-}C_7)$-cycloalkyl, hydroxy and $(C_1\text{-}C_4)$-alkoxy,
$R^5$ represents hydrogen or $(C_1\text{-}C_4)$-alkyl,
$R^6$ represents hydrogen or $(C_1\text{-}C_4)$-alkyl,
  in which $(C_1\text{-}C_4)$-alkyl may be substituted by 1 or 2 substituents independently of one another selected from the group consisting of fluorine, trifluoromethyl, $(C_1\text{-}C_4)$-alkyl, hydroxy and $(C_1\text{-}C_4)$-alkoxy,
or
$R^5$ and $R^6$ together with the carbon atoms to which they are attached form a 3- to 7-membered carbocycle,
$R^7$ represents hydrogen, cyano, $(C_3\text{-}C_7)$-cycloalkyl, hydroxycarbonyl or $(C_1\text{-}C_4)$-alkoxycarbonyl,
$R^2$ represents a group of the formula

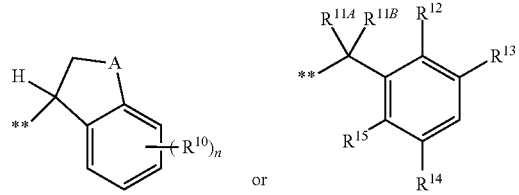

where
** represents the point of attachment to the uracil nitrogen atom,
A represents —$CH_2$—, —$CH_2$—$CH_2$—, —O—$CH_2$-## or oxygen,
  in which ## represents the point of attachment to the phenyl ring,
n represents a number 0, 1 or 2,
$R^{10}$ represents hydrogen, halogen, difluoromethyl, trifluoromethyl, $(C_1\text{-}C_4)$-alkyl, difluoromethoxy, trifluoromethoxy or $(C_1\text{-}C_4)$-alkoxy,
$R^{11A}$ represents hydrogen or deuterium,
$R^{11B}$ represents hydrogen, deuterium or $(C_1\text{-}C_4)$-alkyl,
$R^{12}$ represents hydrogen, halogen, $(C_1\text{-}C_4)$-alkyl, difluoromethyl or trifluoromethyl,
$R^{13}$ represents halogen, $(C_1\text{-}C_4)$-alkyl, difluoromethyl or trifluoromethyl,
$R^{14}$ represents hydrogen or halogen,
$R^{15}$ represents hydrogen or halogen, $R^3$ represents

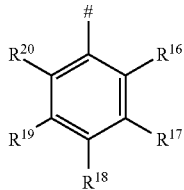

where
represents the point of attachment to the uracil nitrogen atom,
$R^{16}$ represents hydrogen,
$R^{17}$ represents hydrogen, halogen, $(C_1-C_4)$-alkyl or $(C_1-C_4)$-alkoxy,
$R^{18}$ represents $(C_1-C_4)$-alkyl, $(C_1-C_4)$-alkoxy, $(C_1-C_4)$-alkylthio, $(C_1-C_4)$-alkylsulfinyl, $(C_1-C_4)$-alkylsulfonyl or $-N(R^{21}R^{22})$,
　in which $(C_1-C_4)$-alkoxy may be substituted by a substituent independently of one another selected from the group consisting of hydroxy, $(C_1-C_4)$-alkoxycarbonyl, amino, mono-$(C_1-C_4)$-alkylamino, di-$(C_1-C_4)$-alkylamino, aminocarbonyl, mono-$(C_1-C_4)$-alkylaminocarbonyl and di-$(C_1-C_4)$-alkylaminocarbonyl,
　where
　　$R^{21}$ represents $(C_1-C_4)$-alkyl, $(C_1-C_4)$-alkoxycarbonyl or $(C_1-C_4)$-alkylaminocarbonyl,
　　　in which $(C_1-C_4)$-alkylaminocarbonyl may be substituted by hydroxy or $(C_1-C_4)$-alkoxy,
　　$R^{22}$ represents hydrogen or $(C_1-C_4)$-alkyl,
or
$R^{18}$ represents 4- to 7-membered heterocyclyl or 5- to 6-membered heteroaryl,
　in which 4- to 7-membered heterocyclyl may be substituted by 1 to 3 substituents independently of one another selected from the group consisting of halogen, trifluoromethyl, $(C_1-C_4)$-alkyl, hydroxy, oxo, amino and $(C_1-C_4)$-alkoxycarbonyl,
　　in which $(C_1-C_4)$-alkyl may be substituted by 1 or 2 substituents independently of one another selected from the group consisting of halogen, hydroxy and $-N(R^{23}R^{24})$,
　　　in which $R^{23}$ represents hydrogen, $(C_1-C_4)$-alkyl or $(C_1-C_4)$-alkylcarbonyl,
　　　in which $R^{24}$ represents hydrogen or $(C_1-C_4)$-alkyl,
　in which 5- to 6-membered heteroaryl may be substituted by 1 or 2 substituents independently of one another selected from the group consisting of halogen, trifluoromethyl, $(C_1-C_4)$-alkyl, hydroxy, amino and $(C_1-C_4)$-alkoxycarbonyl,
　　in which $(C_1-C_4)$-alkyl may be substituted by 1 or 2 substituents independently of one another selected from the group consisting of halogen, hydroxy and $-N(R^{23}R^{24})$,
　　　in which $R^{23}$ represents hydrogen, $(C_1-C_4)$-alkyl or $(C_1-C_4)$-alkylcarbonyl,
　　　in which $R^{24}$ represents hydrogen or $(C_1-C_4)$-alkyl,
$R^{19}$ represents hydrogen, halogen, cyano, $(C_1-C_4)$-alkyl or $(C_1-C_4)$-alkoxy,
$R^{20}$ represents hydrogen, halogen, $(C_1-C_4)$-alkyl or $(C_1-C_4)$-alkoxy,
or
$R^3$ represents

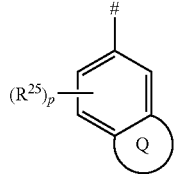

in which
represents the point of attachment to the uracil nitrogen atom,
the ring Q represents 5- to 7-membered heterocyclyl or 5- or 6-membered heteroaryl,
　in which 5- to 7-membered heterocyclyl and 5- or 6-membered heteroaryl may be substituted by 1 to 4 substituents independently of one another selected from the group consisting of halogen, difluoromethyl, trifluoromethyl, trideuteromethyl, $(C_1-C_6)$-alkyl, $(C_3-C_7)$-cycloalkyl, oxo, hydroxyl, $(C_1-C_4)$-alkylcarbonyl, $(C_1-C_4)$-alkoxycarbonyl, aminocarbonyl and $(C_1-C_4)$-alkylsulfonyl,
　in which 5- or 6-membered heteroaryl may be substituted by 1 to 2 substituents independently of one another selected from the group consisting of $(C_1-C_6)$-alkyl, $(C_3-C_7)$-cycloalkyl, hydroxy, $(C_1-C_4)$-alkylcarbonyl, $(C_1-C_4)$-alkoxycarbonyl, aminocarbonyl and $(C_1-C_4)$-alkylsulfonyl,
　and
　in which two $(C_1-C_6)$-alkyl radicals attached to a carbon atom of 5- to 7-membered heterocyclyl together with the carbon atom to which they are attached may form a 3- to 6-membered carbocycle,
$R^{25}$ represents halogen, $(C_1-C_4)$-alkyl or $(C_1-C_4)$-alkoxy,
p represents a number 0, 1, 2 or 3,
$R^4$ represents hydrogen or $(C_1-C_4)$-alkyl,
and the salts, solvates and solvates of the salts thereof.

Compounds of the invention are the compounds of the formula (I) and the salts, solvates and solvates of the salts thereof, the compounds that are encompassed by formula (I) and are of the formulae given below and the salts, solvates and solvates of the salts thereof and the compounds that are encompassed by the formula (I) and are mentioned below as embodiments and the salts, solvates and solvates of the salts thereof if the compounds that are encompassed by the formula (I) and are mentioned below are not already salts, solvates and solvates of the salts.

The compounds of the invention may, depending on their structure, exist in different stereoisomeric forms, i.e. in the form of configurational isomers or else, if appropriate, of conformational isomers (enantiomers and/or diastereomers, including those in the case of atropisomers). The present invention therefore encompasses the enantiomers and diastereomers and the respective mixtures thereof. It is possible to isolate the stereoisomerically homogeneous constituents from such mixtures of enantiomers and/or diastereomers in a known manner.

If the compounds of the invention can occur in tautomeric forms, the present invention encompasses all the tautomeric forms.

Preferred salts in the context of the present invention are physiologically acceptable salts of the compounds according to the invention. Also encompassed are salts which are not themselves suitable for pharmaceutical applications but can be used, for example, for isolation or purification of the compounds of the invention.

Physiologically acceptable salts of the compounds according to the invention include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the inventive compounds also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates in the context of the invention are described as those forms of the compounds of the invention which form a complex in the solid or liquid state by coordination with solvent molecules. Hydrates are a specific form of the solvates in which the coordination is with water. Solvates preferred in the context of the present invention are hydrates.

The present invention additionally also encompasses prodrugs of the compounds of the invention. The term "prodrugs" encompasses compounds which for their part may be biologically active or inactive but are converted during their residence time in the body into compounds according to the invention (for example by metabolism or hydrolysis).

In the context of the present invention, unless specified otherwise, the substituents are defined as follows:

Alkyl in the context of the invention is a straight-chain or branched alkyl radical having 1 to 4 carbon atoms. The following may be mentioned by way of example and by way of preference: methyl, ethyl, n-propyl, isopropyl, n-butyl, isobutyl, sec-butyl and tert-butyl.

Alkylcarbonyloxy in the context of the invention is a straight-chain or branched alkylcarbonyl radical which is attached via an oxygen atom and carries 1 to 4 carbon atoms in the alkyl chain. The following may be mentioned by way of example and by way of preference: methylcarbonyloxy, ethylcarbonyloxy, n-propylcarbonyloxy, isopropylcarbonyloxy, n-butylcarbonyloxy, isobutylcarbonyloxy and tert-butylcarbonyloxy.

Alkoxy in the context of the invention is a straight-chain or branched alkoxy radical 1 to 4 carbon atoms. The following may be mentioned by way of example and by way of preference: methoxy, ethoxy, n-propoxy, isopropoxy, n-butoxy and tert-butoxy.

Alkoxycarbonyl in the context of the invention is a straight-chain or branched alkoxy radical having 1 to 4 carbon atoms and a carbonyl group attached to the oxygen. Preference is given to a linear or branched alkoxycarbonyl radical having 1 to 4 carbon atoms in the alkoxy group. The following may be mentioned by way of example and by way of preference: methoxycarbonyl, ethoxycarbonyl, n-propoxycarbonyl, isopropoxycarbonyl and tert-butoxycarbonyl.

Alkoxycarbonylamino in the context of the invention is an amino group having a linear or branched alkoxycarbonyl substituent which has 1 to 4 carbon atoms in the alkyl chain and is attached to the nitrogen atom via the carbonyl group. The following may be mentioned by way of example and by way of preference: methoxycarbonylamino, ethoxycarbonylamino, propoxycarbonylamino, n-butoxycarbonylamino, isobutoxycarbonylamino and tert-butoxycarbonylamino.

Alkylthio in the context of the invention is a linear or branched alkyl radical which has 1 to 4 carbon atoms and is bonded via a sulfur atom. The following may be mentioned by way of example and by way of preference: methylthio, ethylthio, n-propylthio, isopropylthio, 1-methylpropylthio, n-butylthio, iso-butylthio and tert-butylthio.

Alkylsulfinyl in the context of the invention is a straight-chain or branched alkyl radical having 1 to 4 carbon atoms which is attached via a sulfoxide group. The following may be mentioned by way of example and by way of preference: methylsulfinyl, ethylsulfinyl, n-propylsulfinyl, isopropylsulfinyl, n-butylsulfinyl and tert-butylsulfinyl.

Alkylsulfonyl in the context of the invention is a straight-chain or branched alkyl radical which has 1 to 4 carbon atoms and is bonded via a sulfonyl group. Preferred examples include: methylsulfonyl, ethylsulfonyl, n-propylsulfonyl, isopropylsulfonyl, n-butylsulfonyl and tert-butylsulfonyl.

Monoalkylamino in the context of the invention is an amino group having a linear or branched alkyl substituent having 1 to 4 carbon atoms. The following may be mentioned by way of example and by way of preference: methylamino, ethylamino, n-propylamino, isopropylamino and tert-butylamino.

Dialkylamino in the context of the invention is an amino group having two identical or different, straight-chain or branched alkyl substituents each having 1 to 4 carbon atoms. The following may be mentioned by way of example and by way of preference: N,N-dimethylamino, N,N-diethylamino, N-ethyl-N-methylamino, N-methyl-N-n-propylamino, N-isopropyl-N-n-propylamino and N-tert-butyl-N-methylamino.

Monoalkylaminocarbonyl in the context of the invention is an amino group which is attached via a carbonyl group and has a straight-chain or branched alkyl substituent having 1 to 4 carbon atoms. The following may be mentioned by way of example and by way of preference: methylaminocarbonyl, ethylaminocarbonyl, n-propylaminocarbonyl, isopropylaminocarbonyl, n-butylaminocarbonyl and tert-butylaminocarbonyl.

Dialkylaminocarbonyl in the context of the invention is an amino group which is attached via a carbonyl group and has two identical or different, straight-chain or branched alkyl substituents each having 1 to 4 carbon atoms. The following may be mentioned by way of example and by way of preference: N,N-dimethylaminocarbonyl, N,N-diethylaminocarbonyl, N-ethyl-N-methylaminocarbonyl, N-methyl-N-n-propylaminocarbonyl, N-n-butyl-N-methylaminocarbonyl and N-tert-butyl-N-methylaminocarbonyl.

Monoalkylaminocarbonylamino in the context of the invention is an amino group which carries a straight-chain or branched alkylaminocarbonyl substituent having 1 to 4 carbon atoms in the alkyl chain and is attached via the carbonyl group. The following may be mentioned by way of example and by way of preference: methylaminocarbonylamino, ethylaminocarbonylamino, n-propylaminocarbonylamino, isopropylaminocarbonylamino, n-butylaminocarbonylamino and tert-butylaminocarbonylamino.

Dialkylaminocarbonylamino in the context of the invention is an amino group which carries a straight-chain or branched dialkylaminocarbonyl substituent having in each case 1 to 4 carbon atoms in the alkyl chain which may be identical or different, and is attached via the carbonyl group. The following may be mentioned by way of example and by way of preference: N,N-dimethylaminocarbonylamino, N,N-diethylaminocarbonylamino, N-ethyl-N-methylaminocarbonylamino, N-methyl-N-n-propylaminocarbonylamino, N-n-butyl-N-methylaminocarbonylamino and N-tert-butyl-N-methylaminocarbonylamino.

Heterocyclyl or heterocyclus in the context of the invention is a saturated or partially unsaturated heterocycle having a total of 4 to 7 ring atoms which contains 1 to 3 ring heteroatoms from the group consisting of N, O and S and is attached via a ring carbon atom or optionally a ring nitrogen atom. Examples include: azetidinyl, pyrrolidinyl, tetrahydrofuranyl, imidazolidinyl, dihydroimidazolyl, pyrazolidinyl, dihydrotriazolyl, oxazolidinyl, dihydrooxazolyl, thiazolidinyl, dihydrooxadiazolyl, piperidinyl, piperazinyl, tetrahydropyranyl, oxazinanyl, hexahydropyrimidinyl, morpholinyl, thiomorpholinyl and azepanyl. Preference is given to 5- or 6-membered heterocyclyl radicals having 1 to 3 ring heteroatoms. The following may be mentioned by way of example and by way of preference: imidazolidinyl, dihydroimidazolyl, pyrazolidinyl, dihydrotriazolyl, oxazolidinyl, dihydrooxazolyl, piperazinyl and morpholinyl.

Heteroaryl in the context of the invention is a monocyclic aromatic heterocycle (heteroaromatic) which has a total 5 or 6 ring atoms, contains up to three identical or different ring heteroatoms from the group of N, O and S and is joined via a ring carbon atom or via any ring nitrogen atom. Examples include: furyl, pyrrolyl, thienyl, pyrazolyl, imidazolyl, thiazolyl, oxazolyl, isoxazolyl, isothiazolyl, triazolyl, oxadiazolyl, thiadiazolyl, pyridyl, pyrimidinyl, pyridazinyl, pyrazinyl and triazinyl. Preference is given to monocyclic 5-membered heteroaryl radicals having two or three ring heteroatoms from the group consisting of N, O and S, for example thiazolyl, oxazolyl, isothiazolyl, isoxazolyl, pyrazolyl, imidazolyl, triazolyl, oxadiazolyl and thiadiazolyl.

Halogen in the context of the invention includes fluorine, chlorine, bromine and iodine. Preference is given to chlorine or fluorine.

An oxo group in the context of the invention is an oxygen atom attached to a carbon atom via a double bond.

In the formulae of the group that A, $R^1$, $R^2$, $R^3$ and $R^{18}$ may represent, the end point of the line marked by a symbol * or  or * or # or ## or ### does not represent a carbon atom or a $CH_2$ group but is part of the bond to the atom mentioned in each case.

When radicals in the compounds of the invention are substituted, the radicals may be mono- or polysubstituted, unless specified otherwise. In the context of the present invention, all radicals which occur more than once are defined independently of one another. Substitution by one or two identical or different substituents is preferred. Very particular preference is given to substitution by one substituent.

Preference is given in the context of the present invention to compounds of the formula (I) in which
$R^1$ represents cyano, 5-membered heterocyclyl or 5-membered heteroaryl,
where 5-membered heterocyclyl may be substituted by oxo, and
where 5-membered heteroaryl may be substituted by hydroxy,
or
$R^1$ represents a group of the formula

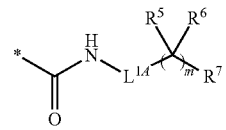

where
* represents the point of attachment to the uracil group,
m represents 0 or 1,
$L^{1A}$ represents a bond or $(C_1-C_4)$-alkanediyl,
$R^5$ represents hydrogen or $(C_1-C_4)$-alkyl,
$R^6$ represents hydrogen or $(C_1-C_4)$-alkyl,
in which $(C_1-C_4)$-alkyl may be substituted by 1 or 2 substituents independently of one another selected from the group consisting of fluorine, trifluoromethyl, $(C_1-C_4)$-alkyl, hydroxy and $(C_1-C_4)$-alkoxy,
or
$R^5$ and $R^6$ together with the carbon atoms to which they are attached form a 3- to 6-membered carbocycle,
$R^7$ represents hydrogen, $(C_1-C_4)$-alkyl, cyano, $(C_3-C_6)$-cycloalkyl, hydroxycarbonyl or $(C_1-C_4)$-alkoxycarbonyl,
or
$R^1$ represents a group of the formula

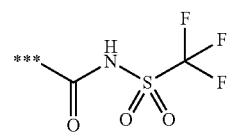

where
*** represents the point of attachment to the uracil group,
$R^2$ represents a group of the formula

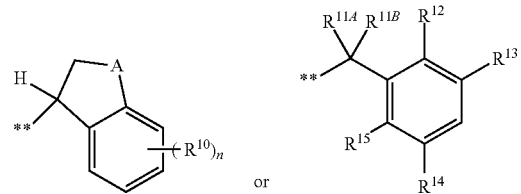

where
** represents the point of attachment to the uracil nitrogen atom,
A represents —$CH_2$— or —$CH_2$—$CH_2$—,
n represents a number 0, 1 or 2,
$R^{10}$ represents hydrogen, fluorine, chlorine, difluoromethyl, trifluoromethyl or methyl,
$R^{11A}$ represents hydrogen or deuterium,
$R^{11B}$ represents hydrogen or deuterium,
$R^{12}$ represents fluorine, chlorine, methyl or trifluoromethyl,
$R^{13}$ represents fluorine, chlorine, methyl or trifluoromethyl, $R^{14}$ represents hydrogen,
$R^{15}$ represents hydrogen,
$R^3$ represents

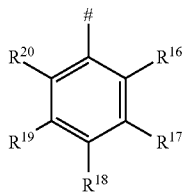

in which
represents the point of attachment to the uracil nitrogen atom,
$R^{16}$ represents hydrogen,
$R^{17}$ represents hydrogen, halogen, methoxy or ethoxy,
$R^{18}$ represents $(C_1-C_4)$-alkyl, methoxy or ethoxy,
or
$R^{18}$ represents 5- or 6-membered heterocyclyl,
where 5- or 6-membered heterocyclyl may be substituted by 1 or 2 substituents independently of one another selected from the group consisting of trifluoromethyl, methyl and oxo,
$R^{19}$ represents hydrogen,
$R^{20}$ represents hydrogen,
or
$R^3$ represents a group of the formula

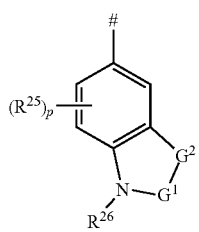 or 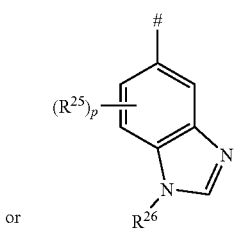

where
represents the point of attachment to the uracil nitrogen atom,
$G^1$ represents C=O or $SO_2$,
$G^2$ represents $CR^{27A}R^{27B}$, $NR^{28}$, O or S,
where
$R^{27A}$ represents hydrogen, fluorine, $(C_1-C_4)$-alkyl or hydroxy,
$R^{27B}$ represents hydrogen, fluorine, chlorine, $(C_1-C_4)$-alkyl or trifluoromethyl,
or
$R^{27A}$ and $R^{27B}$ together with the carbon atom to which they are attached form a 3- to 6-membered carbocycle,
$R^{28}$ represents hydrogen, $(C_1-C_6)$-alkyl or $(C_3-C_7)$-cycloalkyl,
$R^{25}$ represents fluorine or methyl,
p represents a number 0 or 1,
$R^{26}$ represents hydrogen, $(C_1-C_6)$-alkyl or $(C_3-C_6)$-cycloalkyl,
$R^4$ represents hydrogen or methyl,
and the salts, solvates and solvates of the salts thereof.
Preference is given in the context of the present invention to compounds of the formula (I) in which $R^1$ represents cyano, 5-membered heterocyclyl or 5-membered heteroaryl,
where 5-membered heterocyclyl may be substituted by oxo,
and
where 5-membered heteroaryl may be substituted by hydroxy,
or
$R^1$ represents a group of the formula

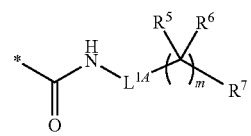

where
* represents the point of attachment to the uracil group,
m represents 0 or 1,
$L^{14}$ represents a bond or $(C_1-C_4)$-alkanediyl,
$R^5$ represents hydrogen or $(C_1-C_4)$-alkyl,
$R^6$ represents hydrogen or $(C_1-C_4)$-alkyl,
in which $(C_1-C_4)$-alkyl may be substituted by 1 or 2 substituents independently of one another selected from the group consisting of fluorine, trifluoromethyl, $(C_1-C_4)$-alkyl, hydroxy and $(C_1-C_4)$-alkoxy,
or
$R^5$ and $R^6$ together with the carbon atoms to which they are attached form a 3- to 6-membered carbocycle,
$R^7$ represents hydrogen, $(C_1-C_4)$-alkyl, cyano, $(C_3-C_6)$-cycloalkyl, hydroxycarbonyl or $(C_1-C_4)$-alkoxycarbonyl,
$R^2$ represents a group of the formula

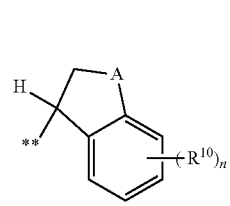 or 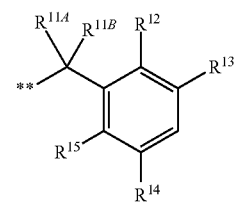

where
** represents the point of attachment to the uracil nitrogen atom,
A represents —$CH_2$— or —$CH_2$—$CH_2$—,
n represents a number 0, 1 or 2,
$R^{10}$ represents hydrogen, fluorine, chlorine, difluoromethyl, trifluoromethyl or methyl,
$R^{11A}$ represents hydrogen or deuterium,
$R^{11B}$ represents hydrogen or deuterium,
$R^{12}$ represents fluorine, chlorine, methyl or trifluoromethyl,
$R^{13}$ represents fluorine, chlorine, methyl or trifluoromethyl,
$R^{14}$ represents hydrogen,
$R^{15}$ represents hydrogen, $R^3$ represents

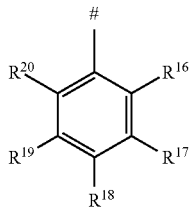

in which
represents the point of attachment to the uracil nitrogen atom,
$R^{16}$ represents hydrogen,
$R^{17}$ represents hydrogen, halogen, methoxy or ethoxy,
$R^{18}$ represents $(C_1-C_4)$-alkyl, methoxy or ethoxy,
or
$R^{18}$ represents 5- or 6-membered heterocyclyl,
where 5- or 6-membered heterocyclyl may be substituted by 1 or 2 substituents independently of one another selected from the group consisting of trifluoromethyl, methyl and oxo,
$R^{19}$ represents hydrogen,
$R^{20}$ represents hydrogen,
or
$R^3$ represents a group of the formula

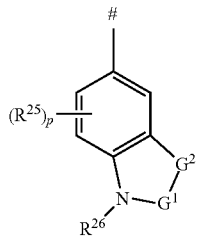 or 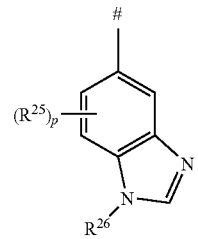

where
represents the point of attachment to the uracil nitrogen atom,
$G^1$ represents C=O or $SO_2$,
$G^2$ represents $CR^{27A}R^{27B}$, $NR^{28}$, O or S,
where
$R^{27A}$ represents hydrogen, fluorine, $(C_1-C_4)$-alkyl or hydroxy,
$R^{27B}$ represents hydrogen, fluorine, chlorine, $(C_1-C_4)$-alkyl or trifluoromethyl,
or
$R^{27A}$ and $R^{27B}$ together with the carbon atom to which they are attached form a 3- to 6-membered carbocycle,
$R^{28}$ represents hydrogen, $(C_1-C_6)$-alkyl or $(C_3-C_7)$-cycloalkyl,
$R^{25}$ represents fluorine or methyl,
p represents a number 0 or 1,
$R^{26}$ represents hydrogen, $(C_1-C_6)$-alkyl or $(C_3-C_6)$-cycloalkyl,
$R^4$ represents hydrogen or methyl,
and the salts, solvates and solvates of the salts thereof.
Particular preference is given in the context of the present invention to compounds of the formula (I) in which $R^1$ represents cyano,
or
$R^1$ represents a group of the formula

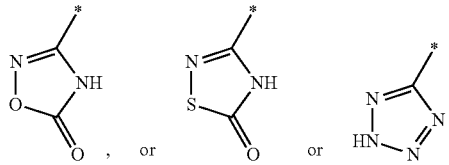 [SMILES: *c1noc(=O)[nH]1 ; *c1nsc(=O)[nH]1 ; *c1nn[nH]n1]

in which
* represents the point of attachment to the uracil carbon atom,
or
$R^1$ represents a group of the formula

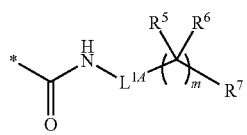

where
* represents the point of attachment to the uracil group,
m represents 0 or 1,
$L^{1A}$ represents a bond, methanediyl or ethanediyl,
$R^5$ represents hydrogen,
$R^6$ represents hydrogen or methyl,
in which methyl may be substituted by hydroxy,
or
$R^5$ and $R^6$ together with the carbon atom to which they are attached form a 3- to 5-membered carbocycle,
$R^7$ represents hydrogen, cyano, hydroxycarbonyl, methoxycarbonyl or ethoxycarbonyl,
$R^2$ represents a group of the formula

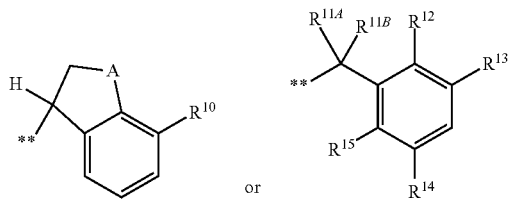

where
** represents the point of attachment to the uracil nitrogen atom,
A represents —$CH_2$— or —$CH_2$—$CH_2$—,
$R^{10}$ represents chlorine or trifluoromethyl,
$R^{11A}$ represents hydrogen,
$R^{11B}$ represents hydrogen,
$R^{12}$ represents chlorine or methyl,
$R^{13}$ represents chlorine or trifluoromethyl,
$R^{14}$ represents hydrogen,
$R^{15}$ represents hydrogen, $R^3$ represents

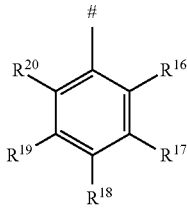

in which
represents the point of attachment to the uracil nitrogen atom,
$R^{16}$ represents hydrogen,
$R^{17}$ represents hydrogen or methoxy,
$R^{18}$ represents methoxy or ethoxy,
or
$R^{18}$ represents a group of the formula

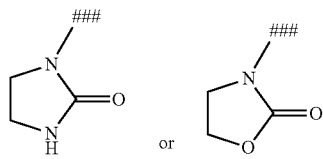

in which
represents the point of attachment to the phenyl ring,
$R^{19}$ represents hydrogen,
$R^{20}$ represents hydrogen,
or
$R^3$ represents a group of the formula

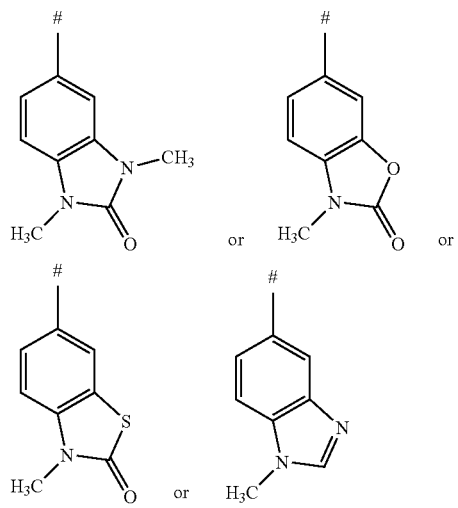

where
represents the point of attachment to the uracil nitrogen atom,
$R^4$ represents hydrogen,
and the salts, solvates and solvates of the salts thereof.
In the context of the present invention, preference is also given to compounds of the formula (I) in which $R^1$ represents cyano,
and the salts, solvates and solvates of the salts thereof.
In the context of the present invention, preference is also given to compounds of the formula (I) in which
$R^1$ represents a group of the formula

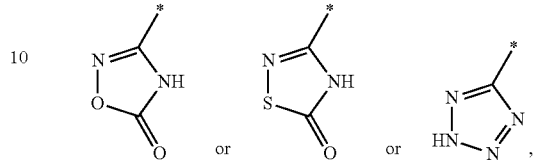

in which
* represents the point of attachment to the uracil carbon atom,
and the salts, solvates and solvates of the salts thereof.
In the context of the present invention, preference is also given to compounds of the formula (I) in which
$R^1$ represents a group of the formula

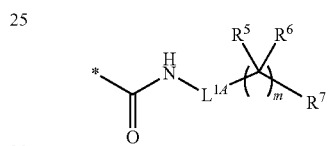

where
* represents the point of attachment to the uracil group,
m represents 0 or 1,
$L^{14}$ represents a bond, methanediyl or ethanediyl,
$R^5$ represents hydrogen,
$R^6$ represents hydrogen or methyl,
  in which methyl may be substituted by hydroxy,
or
$R^5$ and $R^6$ together with the carbon atom to which they are attached form a 3- to 5-membered carbocycle,
$R^7$ represents hydrogen, cyano, hydroxycarbonyl, methoxycarbonyl or ethoxycarbonyl,
and the salts, solvates and solvates of the salts thereof.
In the context of the present invention, preference is also given to compounds of the formula (I) in which
$R^2$ represents a group of the formula

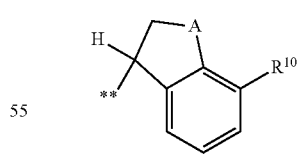

where
** represents the point of attachment to the uracil nitrogen atom,
A represents —$CH_2$— or —$CH_2$—$CH_2$—,
$R^{10}$ represents chlorine or trifluoromethyl,
and the salts, solvates and solvates of the salts thereof.
In the context of the present invention, preference is also given to compounds of the formula (I) in which $R^3$ represents

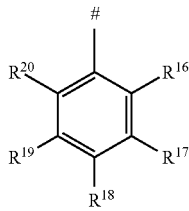

in which
represents the point of attachment to the uracil nitrogen atom,
$R^{16}$ represents hydrogen,
$R^{17}$ represents hydrogen,
$R^{18}$ represents methoxy or ethoxy,
or
$R^{18}$ represents a group of the formula

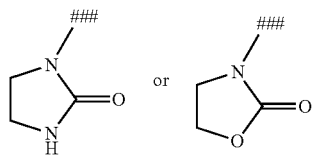

in which
represents the point of attachment to the phenyl ring,
$R^{19}$ represents hydrogen,
$R^{20}$ represents hydrogen,
and the salts, solvates and solvates of the salts thereof.

In the context of the present invention, preference is also given to compounds of the formula (I) in which
$R^3$ represents a group of the formula

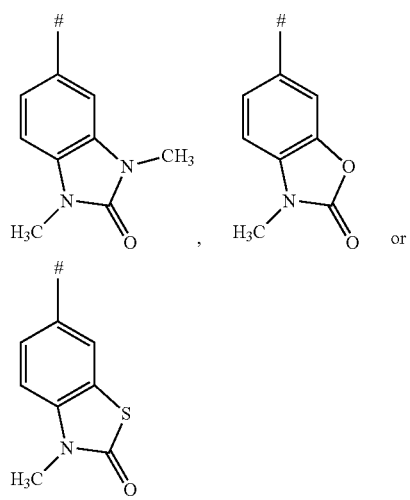

where
represents the point of attachment to the uracil nitrogen atom,
and the salts, solvates and solvates of the salts thereof.

Irrespective of the particular combinations of the radicals specified, the individual radical definitions specified in the particular combinations or preferred combinations of radicals are also replaced as desired by radical definitions from other combinations.

Very particular preference is given to combinations of two or more of the abovementioned preferred ranges.

The invention further provides a process for preparing compounds of the formula (I) according to the invention, characterized in that
[A] a compound of the formula (II)

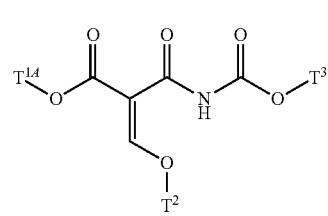

(II)

in which
$T^{1A}$ represents $(C_1-C_4)$-alkyl,
$T^2$ represents $(C_1-C_4)$-alkyl,
$T^3$ represents $(C_1-C_4)$-alkyl,
is reacted in an inert solvent, optionally in the presence of a suitable base, with a compound of the formula (III)

$$R^3-NH_2 \quad (III)$$

in which $R^3$ has the meaning given above
to give a compound of the formula (IV)

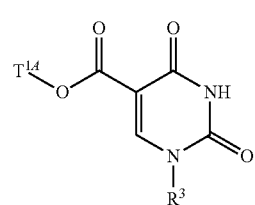

(IV)

in which $T^{1A}$ and $R^3$ each have the meanings given above, this is then reacted in an inert solvent, in the presence of a suitable base, with a compound of the formula (V)

$$X^1-R^2 \quad (V)$$

in which $R^2$ has the meaning given above
and
$X^1$ represents hydroxy or a suitable leaving group, in particular chlorine, bromine or iodine,
to give a compound of the formula (VI)

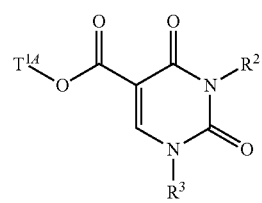

(VI)

in which $T^{1A}$, $R^2$ and $R^3$ each have the meanings given above, the compound of the formula (VI) is then hydrolyzed in an inert solvent in the presence of a suitable acid or base to give a compound of the formula (VII)

(VII)

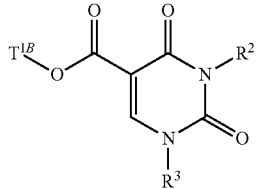

in which $T^{1B}$ represents hydrogen and
in which $R^2$ and $R^3$ each have the meanings given above,
and then in an inert solvent with a compound of the formula (VIII)

(VIII)

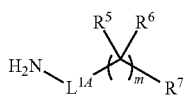

converted into a compound of the formula (I-1)

(I-1)

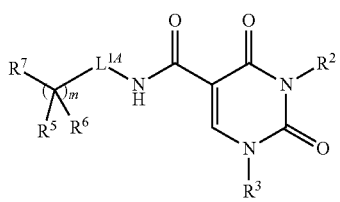

in which $R^2$, $R^3$, $R^5$, $R^6$, $R^7$, $L^{1A}$ and m each have the meanings given above,
or
[B] a compound of the formula (IX)

(IX)

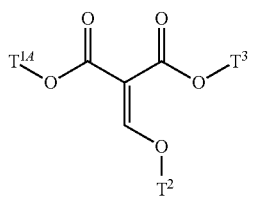

in which $T^{1A}$, $T^2$ and $T^3$ each have the meanings mentioned above,
is converted in an inert solvent or else without solvent with a compound of the formula (III) into a compound of the formula (X)

(X)

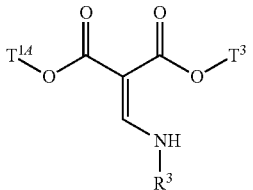

in which $R_3$, $T^{1A}$ and $T^3$ each have the meanings given above,
this is subsequently reacted in an inert solvent with chlorosulfonyl isocyanate to give a compound of the formula (IV) and this is subsequently converted analogously to process [A] to a compound of the formula (I-1),
or
[C] a compound of the formula (XI)

(XI)

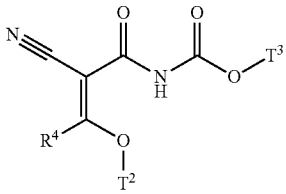

in which
$T^2$ represents $(C_1-C_4)$-alkyl,
$T^3$ represents $(C_1-C_4)$-alkyl and
$R^4$ has the meaning given above,
is reacted in an inert solvent, optionally in the presence of a suitable base, with a compound of the formula (III) to give a compound of the formula (XII)

(XII)

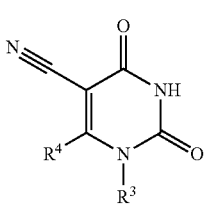

in which $R^3$ and $R^4$ each have the meanings given above,
and this is then, by reaction with a compound of the formula (V) in an inert solvent, if appropriate in the presence of a suitable base,
converted into a compound of the formula (I-2)

(I-2)

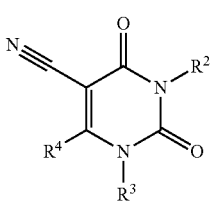

in which $R^2$, $R^3$ and $R^4$ each have the meanings given above, or

[D] a compound of the formula (I-2) is converted with an azide source in the presence of a catalyst in an inert solvent into a compound of the formula (I-3)

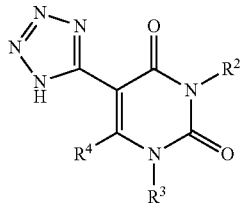

(I-3)

in which $R^2$, $R^3$ and $R^4$ each have the meanings given above, or

[E] a compound of the formula (I-2) is converted with hydroxylamine into a compound of the formula (XIII)

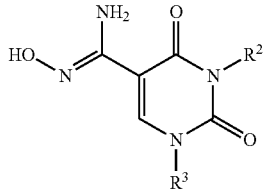

(XIII)

in which $R^2$ and $R^3$ each have the meanings given above, and then in an inert solvent with a carbonyl donor or a thiocarbonyl donor, if appropriate in the presence of a base, to give a compound of the formula (I-4)

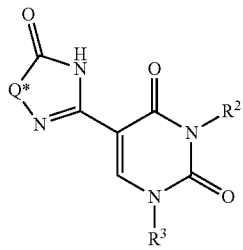

(I-4)

in which $R^2$ and $R^3$ each have the meanings given above and in which

Q* represents oxygen or sulfur, any protecting groups are detached and/or the compounds of the formulae (I-1), (I-2), (I-3) and (I-4) are, where appropriate, converted with the appropriate (i) solvents and/or (ii) bases or acids to the solvates, salts and/or solvates of the salts thereof.

The compounds of the formulae (I-1), (I-2), (I-3) and (I-4) form a subgroup of the compounds according to the invention of the formula (I).

Inert solvents for the process steps (II)+(III)→(IV), (IX)+(III)→(X) and (XI)+(III)→(XII) are, for example, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halohydrocarbons such as dichloromethane, 1,2-dichloroethane, trichloroethylene or chlorobenzene, alcohols such as methanol, ethanol, n-propanol, isopropanol or n-butanol, or other solvents such as dimethylformamide, dimethyl sulfoxide, N,N'-dimethylpropyleneurea (DMPU), N-methylpyrrolidinone (NMP), pyridine, acetone, 2-butanone or acetonitrile. It is also possible to use mixtures of the solvents mentioned. Preference is given to using ethanol or acetonitrile.

Suitable bases for the process steps (II)+(III)→(IV) und (XI)+(III)→(XII) are alkali metal alkoxides such as sodium or potassium methoxide, sodium or potassium ethoxide or sodium or potassium tert-butoxide, alkali metal hydrides such as sodium or potassium hydride, amides such as sodium amide, lithium or potassium bis(trimethylsilyl)amide or lithium diisopropylamide, or organic bases such as triethylamine, diisopropylethylamine, 1,5-diazabicyclo[4.3.0]non-5-ene (DBN), 1,8-diazabicyclo[5.4.0]undec-7-ene (DBU) or 1,4-diazabicyclo[2.2.2]octane (DABCO®) or phosphazene bases, for example 1-[N-tert-butyl-P,P-di(pyrrolidin-1-yl)phosphorimidoyl]pyrrolidine or N'''-tert-butyl-N,N,N',N'-tetramethyl-N''-[tris(dimethylamino)-lambda⁵-phosphanylidene]phosphorimidetriamide. Preference is given to sodium ethoxide, potassium tert-butoxide and triethylamine.

The base is generally used here in an amount of 1 to 5 mol, preferably in an amount of 1.2 to 3 mol, based on 1 mol of the compound of the formula (II) or (XI). A base is not required in all cases.

The conversions (II)+(III)→(IV), (IX)+(III)→(X) and (XI)+(III)→(XII) are generally carried out within a temperature range from 0° C. to +200° C., preferably at +20° C. to +120° C., optionally in a microwave. The reaction can be carried out under atmospheric, elevated or reduced pressure (for example from 0.5 to 5 bar). In general, the reactions are carried out at atmospheric pressure.

If $X^1$=OH, the conversions (IV)+(V)→(VI) and (XII)+(V)→(I-2) are carried out under Mitsunobu conditions [see: a) Hughes, D. L. "The Mitsunobu Reaction" *Organic Reactions*; John Wiley & Sons, Ltd, 1992, vol. 42, p. 335. b) Hughes, D. L. *Org. Prep. Proceed. Int.* 1996, 28, 127]. The Mitsunobu reaction is effected using triphenylphosphine, or tri-n-butylphosphine, 1,2-bis(diphenylphosphino)ethane (DPPE), diphenyl(2-pyridyl)phosphine (Ph2P-Py), (p-dimethylaminophenyl)diphenylphosphine (DAP-DP), tris(4-dimethylaminophenyl)phosphine (tris-DAP), and a suitable dialkyl azodicarboxylate, for example diethyl azodicarboxylate (DEAD), diisopropyl azodicarboxylate (DIAD), di-tert-butyl azodicarboxylate, N,N,N'N'-tetramethylazodicarboxamide (TMAD), 1,1'-(azodicarbonyl)dipiperidine (ADDP) or 4,7-dimethyl-3,5,7-hexahydro-1,2,4,7-tetrazocin-3,8-dione (DHTD). Preference is given to using triphenylphosphine and diisopropyl azodicarboxylate (DIAD).

Inert solvents for the Mitsunobu reactions (IV)+(V)→(VI) and (XII)+(V)→(I-2) are, for example, ethers such as tetrahydrofuran, diethyl ether, hydrocarbons such as benzene, toluene, xylene, halohydrocarbons such as dichloromethane, dichloroethane or other solvents such as acetonitrile or dimethylformamide (DMF). It is also possible to use mixtures of the solvents mentioned. Preference is given to using THF or a mixture of THF and DMF.

The Mitsunobu reactions (IV)+(V)→(VI) und (XII)+(V)→(I-2) are generally carried out within a temperature range from −78° C. to +180° C., preferably at 0° C. to +50° C., optionally in a microwave. The conversions can be performed at atmospheric, elevated or reduced pressure (for example from 0.5 to 5 bar).

If X¹ represents a suitable leaving group, the conversions (IV)+(V)→(VI) and (XII)+(V)→(I-2) are carried out under conditions for a nucleophilic substitution. In that case, inert solvents for the process steps (IV)+(V)→(VI) and (XII)+(V)→(I-2) are, for example, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halohydrocarbons such as dichloromethane, trichloromethane, 1,2-dichloroethane, trichloroethylene or chlorobenzene, or other solvents such as dimethylformamide, dimethyl sulfoxide, N,N'-dimethylpropyleneurea (DMPU), N-methylpyrrolidinone (NMP), pyridine, acetone, 2-butanone or acetonitrile. It is also possible to use mixtures of the solvents mentioned. Preference is given to using acetonitrile, DMF or acetonitrile in a mixture with dimethylformamide.

Suitable bases for the process steps (IV)+(V)→(VI) and (XII)+(V)→(I-2) are customary inorganic bases. These include in particular alkali metal or alkaline earth metal carbonates such as lithium carbonate, sodium carbonate, potassium carbonate, calcium carbonate or caesium carbonate, optionally with addition of an alkali metal iodide, for example potassium iodide, alkali metal alkoxides such as sodium methoxide or potassium methoxide, sodium ethoxide or potassium ethoxide or sodium tert-butoxide or potassium tert-butoxide, alkali metal hydrides such as sodium hydride or potassium hydride, amides such as sodium amide, lithium bis(trimethylsilyl)amide or potassium bis(trimethylsilyl)amide or lithium diisopropylamide. Preference is given to using potassium carbonate with potassium iodide or sodium hydride.

The base is generally used here in an amount of 1 to 5 mol, preferably in an amount of 1.2 to 3 mol, based on 1 mol of the compound of the formula (IV) or (XII).

The reactions (IV)+(V)→(VI) and (XII)+(V)→(I-2) are generally carried out within a temperature range from 0° C. to +100° C., preferably at +20° C. to +80° C., optionally in a microwave. The reaction can be carried out under atmospheric, elevated or reduced pressure (for example from 0.5 to 5 bar). In general, the reactions are carried out at atmospheric pressure.

The hydrolysis of the compounds of the formula (VI) to compounds of the formula (VII) is effected by treating the esters in inert solvents with acids or bases, in which latter case the salts formed at first are converted to the free carboxylic acids by treating with acid. In general, the ester hydrolysis is preferably effected with acids.

Suitable inert solvents for these reactions are water, diethyl ether, tetrahydrofuran, dioxane or glycol dimethyl ether, or other solvents such as acetonitrile, acetic acid, dimethylformamide or dimethyl sulfoxide. It is also possible to use mixtures of the solvents mentioned. In the case of a basic ester hydrolysis, preference is given to using mixtures of water with dioxane, tetrahydrofuran or acetonitrile. For the hydrolysis of tert-butyl esters, the solvent used in the case of reaction with trifluoroacetic acid is preferably dichloromethane, and in the case of reaction with hydrogen chloride preferably tetrahydrofuran, diethyl ether or dioxane. For the hydrolysis of other esters under acidic conditions, preference is given to acetic acid or a mixture of acetic acid and water.

Suitable bases are the alkali metal or alkaline earth metal hydrogencarbonates such as sodium or potassium hydrogencarbonate. Preference is given to sodium hydrogencarbonate.

Suitable acids for the ester cleavage are generally sulfuric acid, hydrogen chloride/hydrochloric acid, hydrogen bromide/hydrobromic acid, phosphoric acid, acetic acid, trifluoroacetic acid, toluenesulfonic acid, methanesulfonic acid or trifluoromethanesulfonic acid, or mixtures thereof, optionally with addition of water. Preference is given to hydrogen chloride or trifluoroacetic acid in the case of the tert-butyl esters, and to hydrochloric acid in a mixture with acetic acid, and to sulfuric acid in a mixture with acetic acid and water in the case of the methyl esters and ethyl esters.

The ester hydrolysis is generally carried out within a temperature range from 0° C. to 180° C., preferably at +20° C. to 120° C.

These conversions can be performed at atmospheric, elevated or reduced pressure (for example from 0.5 to 5 bar). In general, the reactions are in each case carried out at atmospheric pressure.

Inert solvents for the process step (VII)+(VIII)→(I-1) are, for example, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halohydrocarbons such as dichloromethane, trichloromethane, tetrachloromethane, 1,2-dichloroethane, trichloroethylene or chlorobenzene, or other solvents such as acetone, ethyl acetate, acetonitrile, pyridine, dimethyl sulfoxide, N,N-dimethylformamide, N,N'-dimethylpropyleneurea (DMPU) or N-methylpyrrolidone (NMP). It is likewise possible to use mixtures of the solvents mentioned. Preference is given to dichloromethane, tetrahydrofuran, dimethylformamide or mixtures of these solvents.

Suitable condensing agents for the amide formation in process step (VII)+(VIII)→(I-1) are, for example, carbodiimides such as N,N'-diethyl-, N,N'-dipropyl-, N,N'-diisopropyl- and N,N'-dicyclohexylcarbodiimide (DCC) or N-(3-dimethylaminopropyl)-N'-ethylcarbodiimide hydrochloride (EDC), phosgene derivatives such as N,N'-carbonyldiimidazole (CDI), 1,2-oxazolium compounds such as 2-ethyl-5-phenyl-1,2-oxazolium 3-sulfate or 2-tert-butyl-5-methylisoxazolium perchlorate, acylamino compounds such as 2-ethoxy-1-ethoxycarbonyl-1,2-dihydroquinoline, or isobutyl chloroformate, propanephosphonic anhydride (T3P), 1-chloro-N,N,2-trimethylprop-1-en-1-amine, diethyl cyanophosphonate, bis(2-oxo-3-oxazolidinyl)phosphoryl chloride, benzotriazol-1-yloxytris(dimethylamino)phosphonium hexafluorophosphate, benzotriazol-1-yloxytris(pyrrolidino) phosphonium hexafluorophosphate (PyBOP), O-(benzotriazol-1-yl)-N,N,N',N'-tetramethyluronium tetrafluoroborate (TBTU), O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU), O-(7-azabenzotriazol-1-yl)-N,N,N',N'-tetramethyluronium hexafluorophosphate (HATU) or O-(1H-6-chlorobenzotriazol-1-yl)-1,1,3,3-tetramethyluronium tetrafluoroborate (TCTU), optionally in combination with further auxiliaries such as 1-hydroxybenzotriazole (HOBt) or N-hydroxysuccinimide (HOSu), and also as bases alkali metal carbonates, for example sodium carbonate or potassium carbonate or sodium hydrogencarbonate or potassium hydrogencarbonate, or organic bases such as trialkylamines, e.g. triethylamine, N-methylmorpholine, N-methylpiperidine or N,N-diisopropylethylamine. Preference is given to using TBTU in combination with N-methylmorpholine, HATU in combination with N,N-diisopropylethylamine or 1-chloro-N,N,2-trimethylprop-1-en-1-amine.

The condensations (VII)+(VIII)→(I-1) are generally conducted within a temperature range from −20° C. to +100° C., preferably at 0° C. to +60° C. The conversion can be carried out under atmospheric, elevated or reduced pressure (for example from 0.5 to 5 bar). In general, the reactions are carried out at atmospheric pressure.

Azide sources for the process step (I-2)→(I-3) are, for example, trimethylsilyl azide and sodium azide. Preference is given to using trimethylsilyl azide. In general, the azide source is, in particular in the case of trimethylsilyl azide, employed in excess, for example in an amount of from 1.3 mol to 100 mol, based on 1 mol of the compound of the formula (I-2).

Inert solvents for the process step (I-2)→(I-3) using trimethylsilyl azide are, for example, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, or other solvents such as chlorobenzene, dimethylformamide, dimethyl sulfoxide, N,N'-dimethylpropyleneurea (DMPU) or N-methylpyrrolidinone (NMP). It is also possible to use mixtures of the solvents mentioned. Preference is given to using toluene. If sodium azide is used, it may also be suitable to use water, alcohols such as ethanol, n-butanol, isopropanol or mixtures with one of the solvents mentioned.

Suitable catalysts for the conversion (I-2)→(I-3) when using trimethylsilyl azide, are organotin oxides, preferably di-(n-butyl)tin oxide. A suitable catalyst for the conversion (I-2)→(I-3) when using sodium azide is also a Lewis acid such as zinc bromide, zinc chloride, copper(II) sulfate, aluminum trichloride or tributyltin chloride. The catalyst is generally used in an amount of 0.01 to 0.3 mol, preferably in an amount of 0.05 to 0.2 mol, based on 1 mol of the compound of the formula (I-2).

The conversion (I-2)→(I-3) is generally carried out within a temperature range from 20° C. to +180° C., preferably at +80° C. to +120° C., optionally in a microwave. The reaction can be carried out under atmospheric, elevated or reduced pressure (for example from 0.5 to 5 bar). In general, the reactions are carried out at atmospheric pressure.

Inert solvents for the process step (I-2)→(XIII) are, for example, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halohydrocarbons such as dichloromethane, trichloromethane, 1,2-dichloroethane, trichloroethylene or chlorobenzene, or other solvents such as dimethylformamide, dimethyl sulfoxide, N,N'-dimethylpropyleneurea (DMPU), N-methylpyrrolidinone (NMP) or pyridine. It is also possible to use mixtures of the solvents mentioned. Preference is given to using toluene, DMF or DMSO.

The conversion (I-2)→(XIII) is generally carried out within a temperature range from 20° C. to +180° C., preferably at +50° C. to +110° C., optionally in a microwave. The reaction can be carried out under atmospheric, elevated or reduced pressure (for example from 0.5 to 5 bar). In general, the reactions are carried out at atmospheric pressure.

Carbonyl donors for the conversion (XIII)→(I-4) are, for example, carbonyldiimidazole, esters of chloroformic acid such as isobutyl chloroformate or phosgene derivatives such as diphosgene and triphosgene. Preference is given to using isobutyl chloroformate. Preferred for use as thiocarbonyl donor is thiocarbonyldiimidazole.

Inert solvents for the reaction of the compound of the formula (XIII) with a carbonyl donor or a thiocarbonyl donor are, for example, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halohydrocarbons such as dichloromethane, trichloromethane, 1,2-dichloroethane, trichloroethylene or chlorobenzene, or other solvents such as dimethylformamide, dimethyl sulfoxide, N,N'-dimethylpropyleneurea (DMPU), N-methylpyrrolidinone (NMP), acetonitrile or pyridine. It is also possible to use mixtures of the solvents mentioned. Preference is given to using toluene, THF or DMF.

When using a chlorine-containing carbonyl donor such as isobutyl chloroformate, it is advantageous to carry out the reaction in the presence of a suitable base. Suitable bases are, for example, pyridine and organic bases such as triethylamine, diisopropylethylamine, 1,5-diazabicyclo[4.3.0]non-5-ene (DBN) or 1,8-diazabicyclo[5.4.0]undec-7-ene (DBU). Preference is given to pyridine.

The conversion of the compound of the formula (XIII) with a carbonyl donor or a thiocarbonyl donor into the corresponding intermediate is generally carried out in a temperature range of from 0° C. to 80° C., preferably at RT.

The cyclization of the intermediate from the reaction with a carbonyl donor to give the oxadiazolone is in most cases carried out at elevated temperatures, for example from RT to 200° C., optionally in a microwave. In some cases, it is advantageous to employ a base such as potassium tert-butoxide or sodium tert-butoxide.

The cyclization of the intermediate from the reaction with a thiocarbonyl donor to give the thiadiazolone is carried out using boron trifluoride/diethyl ether complex. Suitable solvents are ethers such as diethyl ether, dioxane, tetrahydrofuran, glycol dimethyl ether or diethylene glycol dimethyl ether. Preference is given to THF. The conversion is carried out in a temperature range from 0° C. to 70° C., preferably at RT.

The preparation of the inventive compounds can be illustrated by way of example by the following synthesis schemes:

Scheme 1:

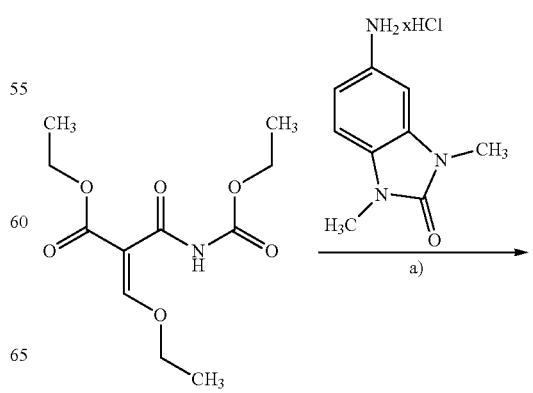

29 -continued 30 -continued
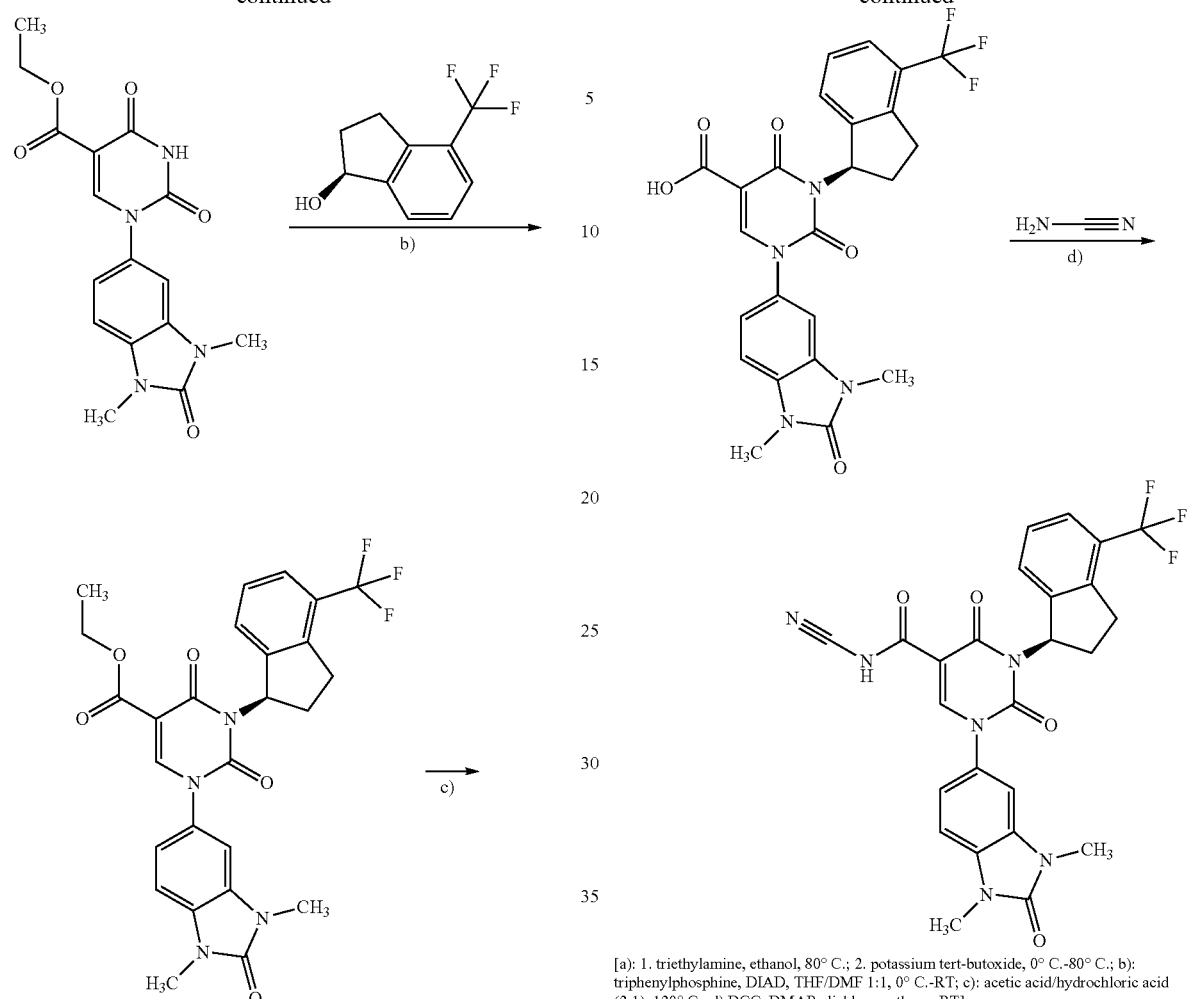
[a]: 1. triethylamine, ethanol, 80° C.; 2. potassium tert-butoxide, 0° C.-80° C.; b): triphenylphosphine, DIAD, THF/DMF 1:1, 0° C.-RT; c): acetic acid/hydrochloric acid (2:1), 120° C.; d) DCC, DMAP, dichloromethane, RT].
Scheme 2:
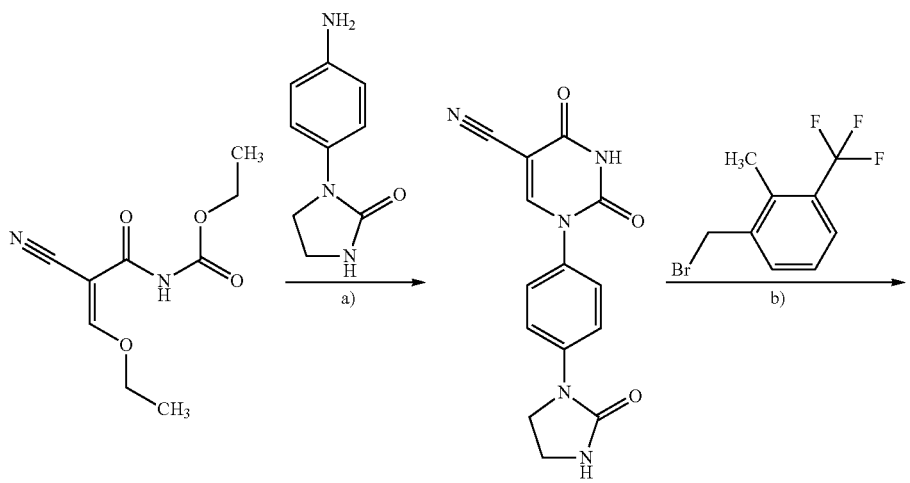

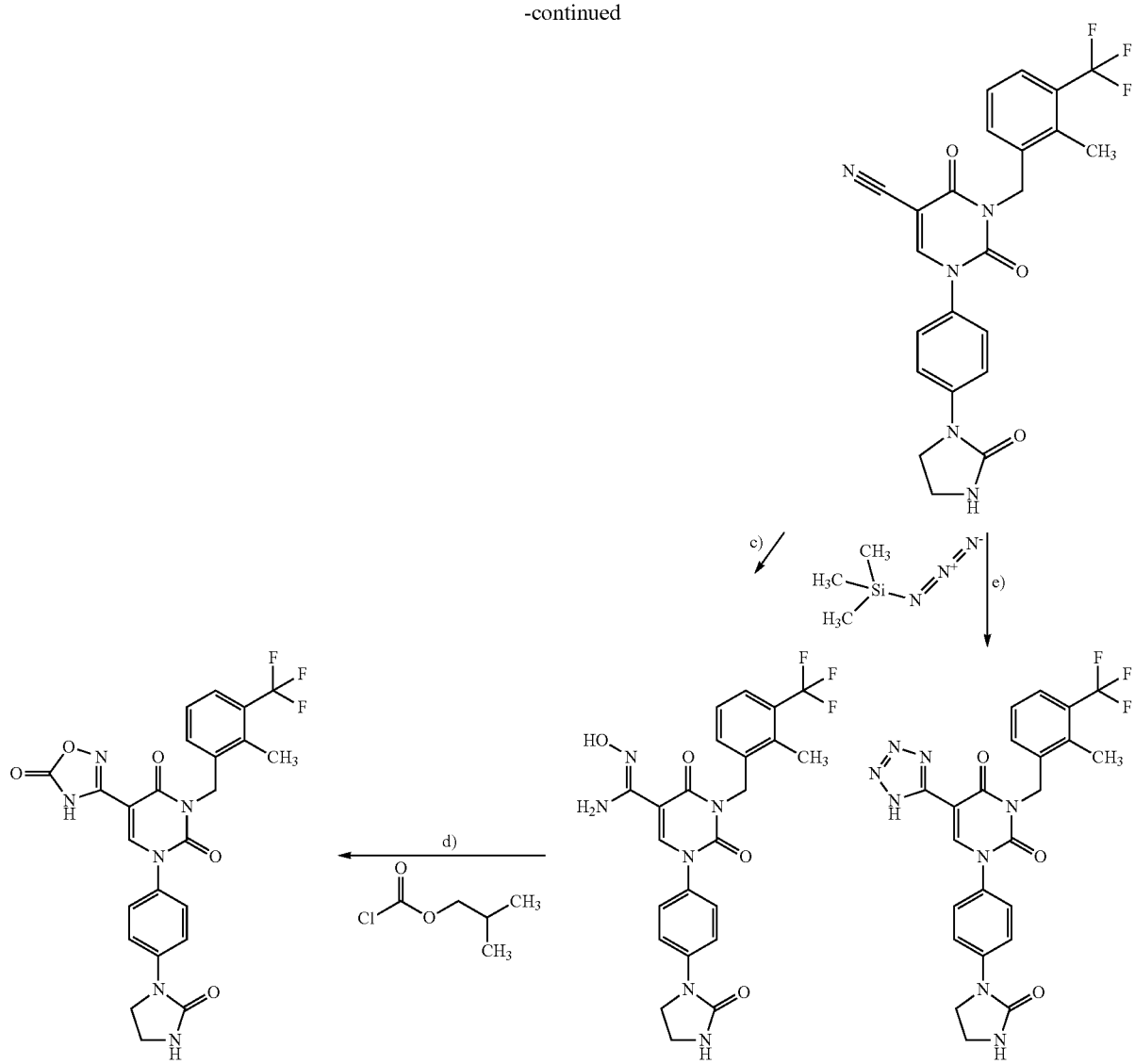

[a]: acetonitrile 180° C., microwave; b): K₂CO₃, KI, acetonitrile, reflux; c): hydroxylamine hydrochloride, triethylamine, DMSO, 75° C.; d) 1. pyridine, DMF, RT, 2) acetonitrile, 180° C., microwave; e) nBu₂Sn=O, toluene, reflux].

The compounds of the formulae (II), (III), (V), (VIII), (IX) and (XI) are commercially available or known from the literature, or can be prepared in analogy to processes known from the literature.

Further compounds of the invention can optionally also be prepared by conversions of functional groups of individual substituents, starting with the compounds of the formula (I) obtained by above processes. These conversions are performed as described in the present experimental section, by customary methods known to those skilled in the art and include, for example, reactions such as nucleophilic and electrophilic substitutions, oxidations, reductions, hydrogenations, transition metal-catalysed coupling reactions, eliminations, alkylation, amination, esterification, ester hydrolysis, etherification, ether cleavage, formation of carbonamides, and introduction and removal of temporary protecting groups.

The compounds of the invention have valuable pharmacological properties and can be used for treatment and/or prophylaxis of diseases in humans and animals.

The compounds of the invention are chymase inhibitors and are therefore suitable for treatment and/or prophylaxis of cardiovascular, inflammatory, allergic and/or fibrotic disorders.

In the context of the present invention, disorders of the cardiovascular system or cardiovascular disorders are understood to mean, for example, the following disorders: acute and chronic heart failure, arterial hypertension, coronary heart disease, stable and unstable angina pectoris, myocardial ischaemia, myocardial infarction, shock, atherosclerosis, cardiac hypertrophy, cardiac fibrosis, atrial and ventricular arrhythmias, transitory and ischaemic attacks, stroke, pre-eclampsia, inflammatory cardiovascular disorders, peripheral and cardiac vascular disorders, peripheral perfusion disorders, arterial pulmonary hypertension, spasms of the coronary arteries and peripheral arteries, thromboses, thromboembolic disorders, oedema development, for example pulmonary oedema, cerebral oedema, renal oedema or heart failure-related oedema, and restenoses such as after thrombolysis treatments, percutaneous transluminal angioplasty (PTA), transluminal coronary angioplasty (PTCA), heart transplants and bypass operations, and micro- and macrovascular damage (vasculitis), reperfusion damage, arterial and venous thromboses, microalbuminuria, myocardial insufficiency, endothelial dysfunction, elevated levels of fibrinogen and of low-density LDL and elevated concentrations of plasminogen activator/inhibitor 1 (PAI-1).

In the context of the present invention, the term "heart failure" also includes more specific or related types of disease, such as acutely decompensated heart failure, right heart failure, left heart failure, global failure, ischaemic cardiomyopathy, dilated cardiomyopathy, congenital heart defects, heart valve defects, heart failure associated with heart valve defects, mitral stenosis, mitral insufficiency, aortic stenosis, aortic insufficiency, tricuspid stenosis, tricuspid insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, and diastolic and systolic heart failure.

The compounds according to the invention are further suitable for the prophylaxis and/or treatment of polycystic kidney disease (PCKD) and of the syndrome of inappropriate ADH secretion (SIADH).

The compounds of the invention are also suitable for treatment and/or prophylaxis of kidney disorders, in particular of acute and chronic renal insufficiency and acute and chronic renal failure.

In the context of the present invention, the term "acute renal insufficiency" encompasses acute manifestations of kidney disease, of kidney failure and/or renal insufficiency with and without the need for dialysis, and also underlying or related renal disorders such as renal hypoperfusion, intradialytic hypotension, volume deficiency (e.g. dehydration, blood loss), shock, acute glomerulonephritis, haemolytic-uraemic syndrome (HUS), vascular catastrophe (arterial or venous thrombosis or embolism), cholesterol embolism, acute Bence-Jones kidney in the event of plasmacytoma, acute supravesicular or subvesicular efflux obstructions, immunological renal disorders such as kidney transplant rejection, immune complex-induced renal disorders, tubular dilatation, hyperphosphataemia and/or acute renal disorders characterized by the need for dialysis, including in the case of partial resections of the kidney, dehydration through forced diuresis, uncontrolled blood pressure rise with malignant hypertension, urinary tract obstruction and infection and amyloidosis, and systemic disorders with glomerular factors, such as rheumatological-immunological systemic disorders, for example lupus erythematodes, renal artery thrombosis, renal vein thrombosis, analgesic nephropathy and renal tubular acidosis, and x-ray contrast agent- and medicament-induced acute interstitial renal disorders.

In the context of the present invention, the term "chronic renal insufficiency" encompasses chronic manifestations of kidney disease, of kidney failure and/or renal insufficiency with and without the need for dialysis, and also underlying or related renal disorders such as renal hypoperfusion, intradialytic hypotension, obstructive uropathy, glomerulopathy, glomerular and tubular proteinuria, renal oedema, haematuria, primary, secondary and chronic glomerulonephritis, membranous and membranoproliferative glomerulonephritis, Alport syndrome, glomerulosclerosis, tubulointerstitial disorders, nephropathic disorders such as primary and congenital kidney disease, renal inflammation, immunological renal disorders such as kidney transplant rejection, immune complex-induced renal disorders, diabetic and non-diabetic nephropathy, pyelonephritis, renal cysts, nephrosclerosis, hypertensive nephrosclerosis and nephrotic syndrome, which can be characterized diagnostically, for example, by abnormally reduced creatinine and/or water excretion, abnormally elevated blood concentrations of urea, nitrogen, potassium and/or creatinine, altered activity of renal enzymes, for example glutamyl synthetase, altered urine osmolarity or urine volume, elevated microalbuminuria, macroalbuminuria, glomerular and arteriolar lesions, tubular dilatation, hyperphosphataemia and/or the need for dialysis, and in the event of renal cell carcinoma, after partial resections of the kidney, dehydration through forced diuresis, uncontrolled blood pressure rise with malignant hypertension, urinary tract obstruction and infection and amyloidosis, and systemic disorders with glomerular factors, such as rheumatological-immunological systemic disorders, for example lupus erythematodes, and also renal artery stenosis, renal artery thrombosis, renal vein thrombosis, analgesic nephropathy and renal tubular acidosis. In addition, x-ray contrast agent- and medicament-induced chronic interstitial renal disorders, metabolic syndrome and dyslipidaemia. The present invention also encompasses the use of the compounds of the invention for the treatment and/or prophylaxis of sequelae of renal insufficiency, for example pulmonary oedema, heart failure, uraemia, anaemia, electrolyte disorders (for example hyperkalaemia, hyponatraemia) and disorders in bone and carbohydrate metabolism.

In addition, the compounds according to the invention are also suitable for treatment and/or prophylaxis of pulmonary arterial hypertension (PAH) and other forms of pulmonary hypertension (PH), of chronic obstructive pulmonary disease (COPD), of acute respiratory distress syndrome (ARDS), of acute lung injury (ALI), of alpha-1-antitrypsin deficiency (AATD), of pulmonary fibrosis, of pulmonary emphysema (for example pulmonary emphysema caused by cigarette smoke), of cystic fibrosis (CF), of acute coronary syndrome (ACS), heart muscle inflammation (myocarditis) and other autoimmune cardiac disorders (pericarditis, endocarditis, valvolitis, aortitis, cardiomyopathy), cardiogenic shock, aneurysms, sepsis (SIRS), multiple organ failure (MODS, MOF), inflammation disorders of the kidney, chronic intestinal disorders (IBD, Crohn's Disease, UC), pancreatitis, peritonitis, rheumatoid disorders, inflammatory skin disorders and inflammatory eye disorders.

The compounds according to the invention can furthermore be used for treatment and/or prophylaxis of asthmatic disorders of varying severity with intermittent or persistent characteristics (refractive asthma, bronchial asthma, allergic asthma, intrinsic asthma, extrinsic asthma, medicament- or dust-induced asthma), of various forms of bronchitis (chronic bronchitis, infectious bronchitis, eosinophilic bronchitis), of Bronchiolitis obliterans, bronchiectasis, pneumonia, idiopathic interstitial pneumonia, farmer's lung and related disorders, of coughs and colds (chronic inflammatory cough, iatrogenic cough), inflammation of the nasal mucosa (including medicament-related rhinitis, vasomotoric rhinitis and seasonal allergic rhinitis, for example hay fever) and of polyps.

The compounds according to the invention are also suitable for treatment and/or prophylaxis of fibrotic disorders of the internal organs, for example the lung, the heart, the kidney, the bone marrow and in particular the liver, and also dermatological fibroses and fibrotic eye disorders. In the context of the present invention, the term "fibrotic disorders" encompasses particularly the following terms: hepatic fibrosis, cirrhosis of the liver, pulmonary fibrosis, endomyocardial fibrosis, cardiomyopathy, nephropathy, glomerulonephritis, interstitial renal fibrosis, fibrotic damage resulting from diabetes, bone marrow fibrosis and similar fibrotic disorders, scleroderma, morphea, keloids, hypertrophic scarring (also following surgical procedures), naevi, diabetic retinopathy and proliferative vitroretinopathy.

The compounds according to the invention are also suitable for controlling postoperative scarring, for example as a result of glaucoma operations.

Furthermore, the compounds according to the invention can also be used cosmetically for ageing and keratinized skin.

In addition, the compounds of the invention can also be used for treatment and/or prophylaxis of dyslipidaemias (hypercholesterolaemia, hypertriglyceridaemia, elevated concentrations of the postprandial plasma triglycerides, hypoalphalipoproteinaemia, combined hyperlipidaemias), nephropathy and neuropathy), cancers (skin cancer, brain tumours, breast cancer, bone marrow tumours, leukaemias, liposarcomas, carcinoma of the gastrointestinal tract, of the liver, pancreas, lung, kidney, urinary tract, prostate and genital tract, and also malignant tumours in the lymphoproliferative system, for example Hodgkin's and non-Hodgkin's lymphoma), of disorders of the gastrointestinal tract and of the abdomen (glossitis, gingivitis, periodontitis, oesophagitis, eosinophilic gastroenteritis, mastocytosis, Crohn's disease, colitis, proctitis, pruritus ani, diarrhoea, coeliac disease, hepatitis, chronic hepatitis, hepatic fibrosis, cirrhosis of the liver, pancreatitis and cholecystitis), skin disorders (allergic skin disorders, psoriasis, acne, eczema, neurodermitis, various forms of dermatitis, and also keratitis, bullosis, vasculitis, cellulitis, panniculitis, lupus erythematodes, erythema, lymphoma, skin cancer, Sweet's syndrome, Weber-Christian syndrome, scarring, warts, chillblains), of disorders of the skeletal bone and of the joints, and also of the skeletal muscle (various forms of arthritis, various forms of arthropathies, scleroderma and of further disorders with an inflammatory or immunological component, for example paraneoplastic syndrome, in the event of rejection reactions after organ transplants and for wound healing and angiogenesis, especially in the case of chronic wounds.

The compounds of the formula (I) according to the invention are additionally suitable for treatment and/or prophylaxis of ophthalmologic disorders, for example glaucoma, normotensive glaucoma, high intraocular pressure and combinations thereof, of age-related macular degeneration (AMD), of dry or non-exudative AMD, moist or exudative or neovascular AMD, choroidal neovascularization (CNV), detached retina, diabetic retinopathy, atrophic lesions to the retinal pigment epithelium (RPE), hypertrophic lesions to the retinal pigment epithelium (RPE), diabetic macular oedema, retinal vein occlusion, choroidal retinal vein occlusion, macular oedema, macular oedema due to retinal vein occlusion, angiogenesis at the front of the eye, for example corneal angiogenesis, for example following keratitis, cornea transplant or keratoplasty, corneal angiogenesis due to hypoxia (extensive wearing of contact lenses), pterygium conjunctiva, subretinal oedema and intraretinal oedema.

In addition, the compounds of the formula (I) according to the invention are suitable for the treatment and/or prophylaxis of elevated and high intraocular pressure resulting from traumatic hyphaema, periorbital oedema, postoperative viscoelastic retention, intraocular inflammation, use of corticosteroids, pupillary block or idiopathic causes, and of elevated intraocular pressure following trabeculectomy and due to pre-operative conditions.

The present invention further provides for the use of the compounds according to the invention for treatment and/or prophylaxis of disorders, especially the disorders mentioned above.

The present invention further provides for the use of the compounds according to the invention for production of a medicament for treatment and/or prophylaxis of disorders, especially the disorders mentioned above.

The present invention further provides the compounds according to the invention for use in a method for treatment and/or prophylaxis of heart failure, pulmonary hypertension, chronic obstructive pulmonary disease, asthma, kidney failure, nephropathy, fibrotic disorders of the internal organs and dermatological fibroses.

The compounds of the invention can be used alone or, if required, in combination with other active ingredients. Accordingly, the present invention further provides medicaments comprising at least one of the compounds according to the invention and one or more further active compounds, especially for treatment and/or prophylaxis of the aforementioned disorders. Preferred examples of active compounds suitable for combinations include:

compounds which inhibit the signal transduction cascade, by way of example and with preference from the group of the kinase inhibitors, especially from the group of the tyrosine kinase and/or serine/threonine kinase inhibitors;

compounds which inhibit the degradation and alteration of the extracellular matrix, by way of example and with preference inhibitors of the matrix metalloproteases (MMPs), especially inhibitors of stromelysin, collagenases, gelatinases and aggrecanases (in this context particularly of MMP-1, MMP-3, MMP-8, MMP-9, MMP-10, MMP-11 and MMP-13) and of metalloelastase (MMP-12);

compounds which block the binding of serotonin to its receptors, by way of example and with preference antagonists of the $5\text{-HT}_{2b}$ receptor;

organic nitrates and NO donors, for example sodium nitroprusside, nitroglycerin, isosorbide mononitrate, isosorbide dinitrate, molsidomine or SIN-1, and inhaled NO;

NO-independent but haem-dependent stimulators of soluble guanylate cyclase, such as especially the compounds described in WO 00/06568, WO 00/06569, WO 02/42301 and WO 03/095451;

NO- and haem-independent activators of soluble guanylate cyclase, such as especially the compounds described in WO 01/19355, WO 01/19776, WO 01/19778, WO 01/19780, WO 02/070462 and WO 02/070510;

prostacyclin analogues, by way of example and with preference iloprost, beraprost, treprostinil or epoprostenol;

compounds which inhibit soluble epoxide hydrolase (sEH), for example N,N'-dicyclohexylurea, 12-(3-adamantan-1-ylureido)dodecanoic acid or 1-adamantan-1-yl-3-{5-[2-(2-ethoxyethoxy)ethoxy]pentyl}urea;

compounds which influence the energy metabolism of the heart, by way of example and with preference etomoxir, dichloroacetate, ranolazine or trimetazidine;

compounds which inhibit the degradation of cyclic guanosine monophosphate (cGMP) and/or cyclic adenosine monophosphate (cAMP), for example inhibitors of phosphodiesterases (PDE) 1, 2, 3, 4 and/or 5, especially PDE 5 inhibitors such as sildenafil, vardenafil and tadalafil;

antithrombotic agents, by way of example and with preference from the group of the platelet aggregation inhibitors, the anticoagulants or the profibrinolytic substances;

hypotensive active ingredients, for example and with preference from the group of calcium antagonists, angiotensin AII antagonists, ACE inhibitors, vasopeptidase inhibitors, endothelin antagonists, renin inhibitors, alpha-receptor blockers, beta-receptor blockers, mineralocorticoid receptor antagonists, and rho kinase inhibitors and the diuretics;

vasopressin receptor antagonists, for example and with preference conivaptan, tolvaptan, lixivaptan, mozavaptan, satavaptan, SR-121463, RWJ 676070 or BAY 86-8050;

bronchodilatory agents, by way of example and with preference from the group of the beta-adrenergic receptor agonists, such as especially albuterol, isoproterenol, metaproterenol, terbutalin, formoterol or salmeterol, or from the group of the anticholinergics, such as especially ipratropium bromide;

anti-inflammatory agents, by way of example and with preference from the group of the glucocorticoids, such as especially prednisone, prednisolone, methylprednisolone, triamcinolone, dexamethasone, beclomethasone, betamethasone, flunisolide, budesonide or fluticasone; and/or active compounds altering lipid metabolism, for example and with preference from the group of the thyroid receptor agonists, cholesterol synthesis inhibitors such as, by way of example and preferably, HMG-CoA reductase inhibitors or squalene synthesis inhibitors, the ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein(a) antagonists.

In a preferred embodiment of the invention, the compounds according to the invention are used in combination with a kinase inhibitor, by way of example and with preference bortezomib, canertinib, erlotinib, gefitinib, imatinib, lapatinib, lestaurtinib, lonafarnib, pegaptinib, pelitinib, semaxanib, sorafenib, regorafenib, sunitinib, tandutinib, tipifarnib, vatalanib, fasudil, lonidamine, leflunomide, BMS-3354825 or Y-27632.

In a preferred embodiment of the invention, the compounds according to the invention are used in combination with a serotonin receptor antagonist, by way of example and with preference PRX-08066.

Antithrombotic agents are preferably understood to mean compounds from the group of the platelet aggregation inhibitors, the anticoagulants or the profibrinolytic substances.

In a preferred embodiment of the invention, the compounds of the invention are administered in combination with a platelet aggregation inhibitor, by way of example and with preference aspirin, clopidogrel, ticlopidine or dipyridamole.

In a preferred embodiment of the invention, the compounds according to the invention are administered in combination with a thrombin inhibitor, by way of example and with preference ximelagatran, melagatran, bivalirudin or clexane.

In a preferred embodiment of the invention, the compounds of the invention are administered in combination with a GPIIb/IIIa antagonist, by way of example and with preference tirofiban or abciximab.

In a preferred embodiment of the invention, the compounds according to the invention are administered in combination with a factor Xa inhibitor, by way of example and with preference rivaroxaban, DU-176b, fidexaban, razaxaban, fondaparinux, idraparinux, PMD-3112, YM-150, KFA-1982, EMD-503982, MCM-17, mLN-1021, DX 9065a, DPC 906, JTV 803, SSR-126512 or SSR-128428.

In a preferred embodiment of the invention, the compounds of the invention are administered in combination with heparin or with a low molecular weight (LMW) heparin derivative.

In a preferred embodiment of the invention, the compounds of the invention are administered in combination with a vitamin K antagonist, by way of example and with preference coumarin.

Hypotensive agents are preferably understood to mean compounds from the group of calcium antagonists, angiotensin AII antagonists, ACE inhibitors, endothelin antagonists, renin inhibitors, alpha-receptor blockers, beta-receptor blockers, mineralocorticoid receptor antagonists, rho kinase inhibitors, and the diuretics.

In a preferred embodiment of the invention, the compounds of the invention are administered in combination with a calcium antagonist, by way of example and with preference nifedipine, amlodipine, verapamil or diltiazem.

In a preferred embodiment of the invention, the compounds of the invention are administered in combination with an alpha-1-receptor blocker, by way of example and with preference prazosin.

In a preferred embodiment of the invention, the compounds of the invention are administered in combination with a beta-receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds of the invention are administered in combination with an angiotensin AII antagonist, by way of example and with preference losartan, candesartan, valsartan, telmisartan or embursatan.

In a preferred embodiment of the invention, the compounds of the invention are administered in combination with an ACE inhibitor, by way of example and with preference enalapril, captopril, lisinopril, ramipril, delapril, fosinopril, quinopril, perindopril or trandopril.

In a preferred embodiment of the invention, the compounds of the invention are administered in combination with an endothelin antagonist, by way of example and with preference bosentan, darusentan, ambrisentan or sitaxsentan.

In a preferred embodiment of the invention, the compounds of the invention are administered in combination with a renin inhibitor, by way of example and with preference aliskiren, SPP-600 or SPP-800.

In a preferred embodiment of the invention, the compounds of the invention are administered in combination with a mineralocorticoid receptor antagonist, by way of example and with preference spironolactone or eplerenone.

In a preferred embodiment of the invention, the compounds according to the invention are administered in combination with a rho kinase inhibitor, by way of example and with preference fasudil, Y-27632, SLx-2119, BF-66851, BF-66852, BF-66853, KI-23095, SB-772077, GSK-269962A or BA-1049.

In a preferred embodiment of the invention, the compounds according to the invention are administered in combination with a diuretic, by way of example and with preference furosemide.

Lipid metabolism modifiers are preferably understood to mean compounds from the group of the CETP inhibitors, thyroid receptor agonists, cholesterol synthesis inhibitors such as HMG-CoA reductase inhibitors or squalene synthesis inhibitors, the ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and the lipoprotein(a) antagonists.

In a preferred embodiment of the invention, the compounds according to the invention are administered in combination with a CETP inhibitor, by way of example and with preference torcetrapib (CP-529 414), JJT-705 or CETP vaccine (Avant).

In a preferred embodiment of the invention, the compounds of the invention are administered in combination with a thyroid receptor agonist such as, for example and preferably, D-thyroxine, 3,5,3'-triiodothyronine (T3), CGS 23425 or axitirome (CGS 26214).

In a preferred embodiment of the invention, the compounds of the invention are administered in combination with an HMG-CoA reductase inhibitor from the class of statins, by way of example and with preference lovastatin, simvastatin, pravastatin, fluvastatin, atorvastatin, rosuvastatin or pitavastatin.

In a preferred embodiment of the invention, the compounds of the invention are administered in combination with a squalene synthesis inhibitor, by way of example and with preference BMS-188494 or TAK-475.

In a preferred embodiment of the invention, the compounds of the invention are administered in combination with an ACAT inhibitor, by way of example and with preference avasimibe, melinamide, pactimibe, eflucimibe or SMP-797.

In a preferred embodiment of the invention, the compounds of the invention are administered in combination with an MTP inhibitor, by way of example and with preference implitapide, BMS-201038, R-103757 or JTT-130.

In a preferred embodiment of the invention, the compounds of the invention are administered in combination with a PPAR-gamma agonist, by way of example and with preference pioglitazone or rosiglitazone.

In a preferred embodiment of the invention, the compounds of the invention are administered in combination with a PPAR-delta agonist, by way of example and with preference GW 501516 or BAY 68-5042.

In a preferred embodiment of the invention, the compounds of the invention are administered in combination with a cholesterol absorption inhibitor, by way of example and with preference ezetimibe, tiqueside or pamaqueside.

In a preferred embodiment of the invention, the compounds of the invention are administered in combination with a lipase inhibitor, by way of example and with preference orlistat.

In a preferred embodiment of the invention, the compounds of the invention are administered in combination with a polymeric bile acid adsorbent, by way of example and with preference cholestyramine, colestipol, colesolvam, CholestaGel or colestimide.

In a preferred embodiment of the invention, the compounds of the invention are administered in combination with a bile acid reabsorption inhibitor, by way of example and with preference ASBT (=IBAT) inhibitors, for example AZD-7806, S-8921, AK-105, BARI-1741, SC-435 or SC-635.

In a preferred embodiment of the invention, the compounds of the invention are administered in combination with a lipoprotein(a) antagonist, by way of example and with preference gemcabene calcium (CI-1027) or nicotinic acid.

The present invention further provides medicaments which comprise at least one compound of the invention, typically together with one or more inert, nontoxic, pharmaceutically suitable excipients, and for the use thereof for the aforementioned purposes.

The compounds of the invention can act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

The compounds of the invention can be administered in administration forms suitable for these administration routes.

Suitable administration forms for oral administration are those which work according to the prior art and release the compounds of the invention rapidly and/or in a modified manner and which contain the compounds of the invention in crystalline and/or amorphized and/or dissolved form, for example tablets (uncoated or coated tablets, for example with gastric juice-resistant or retarded-dissolution or insoluble coatings which control the release of the compound of the invention), tablets or films/oblates which disintegrate rapidly in the oral cavity, films/lyophilizates, capsules (for example hard or soft gelatin capsules), sugar-coated tablets, granules, pellets, powders, emulsions, suspensions, aerosols or solutions.

Parenteral administration can bypass an absorption step (e.g. intravenously, intraarterially, intracardially, intraspinally or intralumbally) or include an absorption (e.g. inhalatively, intramuscularly, subcutaneously, intracutaneously, percutaneously or intraperitoneally). Administration forms suitable for parenteral administration include preparations for injection and infusion in the form of solutions, suspensions, emulsions, lyophilizates or sterile powders.

For the other administration routes, suitable examples are inhalation medicaments (including powder inhalers, nebulizers, aerosols), nasal drops, solutions or sprays; tablets for lingual, sublingual or buccal administration, films/oblates or capsules, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, dusting powders, implants or stents.

Oral and parenteral administration are preferred, especially oral, intravenous and inhalative administration.

The compounds of the invention can be converted to the administration forms mentioned. This can be done in a manner known per se, by mixing with inert, nontoxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulfate, polyoxysorbitan oleate), binders (for example polyvinylpyrrolidone), synthetic and natural polymers (for example albumin), stabilizers (e.g. antioxidants, for example ascorbic acid), colorants (e.g. inorganic pigments, for example iron oxides) and flavour and/or odour correctants.

In general, it has been found to be advantageous in the case of parenteral administration to administer amounts of about 0.001 to 1 mg/kg, preferably about 0.01 to 0.5 mg/kg, of body weight to achieve effective results. In the case of oral administration the dosage is about 0.01 to 100 mg/kg, preferably about 0.01 to 20 mg/kg and most preferably 0.1 to 10 mg/kg of body weight.

It may nevertheless be necessary in some cases to deviate from the stated amounts, specifically as a function of the body weight, route of administration, individual response to the active ingredient, nature of the preparation and time or interval over which administration takes place. Thus, in some cases less than the abovementioned minimum amount may be sufficient, while in other cases the upper limit mentioned must be exceeded. In the case of administration of greater amounts, it may be advisable to divide them into several individual doses over the day.

The working examples which follow illustrate the invention. The invention is not restricted to the examples.

Unless stated otherwise, the percentages in the tests and examples which follow are percentages by weight; parts are parts by weight. Solvent ratios, dilution ratios and concentration data for liquid/liquid solutions, unless indicated otherwise, are based in each case on volume.

A. EXAMPLES

Abbreviations

Ac acetyl
aq. aqueous, aqueous solution
br.d broad doublet (NMR)
br.m broad multiplet (NMR)
br.s broad singlet (NMR)
br.t broad triplet (NMR)
Ex. Example
c concentration
cat. catalytic
TLC thin-layer chromatography
DCI direct chemical ionization (in MS)
DCC dicyclohexylcarbodiimide
DIAD diisopropyl azodicarboxylate
DIEA N,N-diisopropylethylamine
DMAP 4-N,N-dimethylaminopyridine
DMF dimethylformamide
DMSO dimethyl sulfoxide
EDC N'-(3-dimethylaminopropyl)-N-ethylcarbodiimide hydrochloride
ee enantiomeric excess
eq. equivalent(s)
ESI electrospray ionization (in MS)
Et ethyl
GC-MS gas chromatography-coupled mass spectrometry
h hour(s)
HATU O-(7-azabenzotriazol-1-yl)-N,N,N',N'-tetramethyluronium hexafluorophosphate
HOBt 1-hydroxy-1H-benzotriazole hydrate
HPLC high-pressure, high-performance liquid chromatography
conc. concentrated
LC-MS liquid chromatography-coupled mass spectrometry
Me methyl
min minute(s)
MS mass spectrometry
MTBE methyl tert-butyl ether
NMR nuclear magnetic resonance spectrometry
Pd/C palladium on activated carbon
Ph phenyl
PyBOP benzotriazol-1-yloxytris(pyrrolidino)phosphonium hexafluorophosphate
quant. quantitative (in yield)
quin quintet (NMR)
rac racemic, racemate
RT room temperature
$R_t$ retention time (in HPLC)
tBu tert-butyl
TBTU (benzotriazol-1-yloxy)bisdimethylaminomethylium fluoroborate
tert tertiary
TFA trifluoroacetic acid
TFAA trifluoroacetic anhydride
THF tetrahydrofuran
TPPO triphenylphosphine oxide
UV ultraviolet spectrometry
v/v volume to volume ratio (of a solution)

HPLC, GC-MS and LC-MS Methods:

Method 1 (LC-MS): Instrument: Waters ACQUITY SQD UPLC system; column: Waters Acquity UPLC HSS T3 1.8μ 50×1 mm; mobile phase A: 1 l of water+0.25 ml of 99% strength formic acid, mobile phase B: 1 l of acetonitrile+ 0.25 ml of 99% strength formic acid; gradient: 0.0 min 90% A→1.2 min 5% A→2.0 min 5% A; oven: 50° C.; flow rate: 0.40 ml/min; UV detection: 210-400 nm.

Method 2 (LC-MS) instrument: Micromass Quattro Premier with Waters UPLC Acquity; column: Thermo Hypersil GOLD 1.9μ 50×1 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→1.5 min 10% A→2.2 min 10% A oven: 50° C.; flow rate: 0.33 ml/min; UV detection: 210 nm.

Method 3 (LC-MS): Instrument: Micromass Quattro Premier with Waters UPLC Acquity; column: Thermo Hypersil GOLD 1.9μ 50×1 mm; mobile phase A: 1 l of water+0.5 ml of 50% strength formic acid, mobile phase B: 1 l of acetonitrile+0.5 ml of 50% strength formic acid; gradient: 0.0 min 97% A→0.5 min 97% A→3.2 min 5% A→4.0 min 5% A oven: 50° C.; flow rate: 0.3 ml/min; UV detection: 210 nm.

Method 4 (LC-MS): MS instrument type: Waters (Micromass) Quattro Micro; HPLC instrument type: Agilent 1100 series; column: Thermo Hypersil GOLD 3μ 20×4 mm; mobile phase A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A; oven: 50° C.; flow rate: 2 ml/min; UV detection: 210 nm.

Method 5 (preparative HPLC): Column: Reprosil C18, 10 μm, 250 mm×30 mm. Mobile phase A: formic acid 0.1% in water, mobile phase B: acetonitrile; flow rate: 50 ml/min; gradient: 0 to 6 min: 90% A/10% B; 6 min to 27 min: gradient to 95% B; 27 min to 38 min 95% B; 38 min to 39 min gradient to 10% B; 39 min to 43 min (end): 60% A/40% B. Slight variations in the gradient are possible.

Method 6 (preparative HPLC): As Method 4, but using the Chromatorex C18 5 μm, 250×20 mm column.

Method 7 (preparative HPLC): Column: Reprosil C18 10 μm, 250×30, flow rate 50 ml/min, detection at 210 nm, mobile phase acetonitrile (A), water (B); gradient: 3 min 10% A, 27 min 95% A, 34 min 95% A, 34-38 min 10% A.

Method 8 (preparative HPLC): Column: Reprosil C18, 10 μm, 250 mm×30 mm. Mobile phase A: formic acid 0.1% in water, mobile phase B: methanol; flow rate: 50 ml/min; programme: 0 to 4.25 min: 60% A/40% B; 4.25 to 4.50 min: gradient to 60% B; 4.50 min to 17 min gradient to 100% B; 17 min to 19.50 min 100% B; 19.50 min to 19.75 min gradient to 40% B; 19.75 min to 22 min (end): 60% A/40% B. Slight variations in the gradient are possible.

Method 9 (preparative HPLC): Column: Reprosil C18, 10 μm, 250 mm×30 mm. Mobile phase A: water, mobile phase B: methanol; flow rate: 50 ml/min; programme: 0 to 4.25 min: 50% A/50% B; 4.25 to 4.50 min: gradient to 70% B; 4.50 min to 11.5 min gradient to 90% B; 12.00 min to 14.50 min 100% B; 14.50 min to 18.00 min gradient to 50% B (end): Slight variations in the gradient are possible.

Method 10 (preparative HPLC): Column: Reprosil C18, 10 μm, 250 mm×30 mm. Mobile phase A: water, mobile phase B: methanol; flow rate: 50 ml/min; programme: 0 to 4.25 min: 70% A/30% B; 4.25 to 4.50 min: gradient to 50% B; 4.50 min to 11.5 min gradient to 70% B; 12.00 min to 14.50 min 100% B; 14.50 min to 18.00 min gradient to 30% B (end): Slight variations in the gradient are possible.

Method 11 (preparative HPLC): Column: Reprosil C18, 10 μm, 250 mm×30 mm. Mobile phase A: water, mobile phase B: methanol; flow rate: 50 ml/min; programme: 0 to 4.25 min: 60% A/40% B; 4.25 to 4.50 min: gradient to 60% B; 4.50 min to 17 min gradient to 100% B; 17 min to 19.50 min 100% B; 19.50 min to 19.75 min gradient to 40% B; 19.75 min to 22 min (end): 60% A/40% B.

Method 12 (MS; DCI NH$_3$): Instrument: Thermo Fisher-Scientific DSQ; chemical ionization; reactant gas NH$_3$; source temperature: 200° C.; ionization energy 70 eV.

Method 13: Instrument: Waters ACQUITY SQD UPLC system; column: Waters Acquity UPLC HSS T3 1.8μ 30×2 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; oven: 50° C.; flow rate: 0.60 ml/min; UV detection: 208-400 nm.

Method 14 (chiral preparative HPLC): Column: Daicel Chiralpak OD-H 5 μm, 250 mm×20 mm; mobile phase: 0.2% glacial acetic acid in acetonitrile/0.2% glacial acetic acid in ethanol 70:30 (v/v). flow rate 20 ml/min. UV detection: 210 nM, RT.

Method 15 (chiral analytical HPLC): Column: Daicel Chiralpak AD-H 5 μm, 250 mm×4.6 mm; mobile phase: 0.2% glacial acetic acid in acetonitrile/0.2% glacial acetic acid in ethanol 30:70 (v/v). flow rate 1 ml/min. UV detection: 230 nM, RT.

Method 16 (chiral preparative HPLC): Column: Daicel Chiralpak AD-H 5 μm, 250 mm×20 mm; mobile phase: isohexane/ethanol/trifluoroacetic acid/water 49.4:49.4:0.2:1 (v/v/v/v). flow rate 20 ml/min. UV detection: 220 nM, 25° C.

Method 17 (chiral analytical HPLC): Column: Daicel Chiralpak AD-H 5 μm, 250 mm×4.6 mm; mobile phase: isohexane/ethanol/trifluoroacetic acid/water 49.4:49.4:0.2:1 (v/v/v/v). flow rate 20 ml/min. UV detection: 220 nM, 30° C.

Method 18 (chiral preparative HPLC): Column: Daicel Chiralpak AD-H 5 μm, 250 mm×20 mm; mobile phase: isohexane/ethanol/trifluoroacetic acid/water 29.6:69.2:0.2:1 (v/v/v/v). flow rate 20 ml/min. UV detection: 210 nM, 25° C.

Method 19 (LC-MS): MS instrument: Waters (Micromass) QM; HPLC instrument: Agilent 1100 series; column: Agilent ZORBAX Extend-C18 3.0×50 mm 3.5 micron; mobile phase A: 1 l of water+0.01 mol of ammonium carbonate, mobile phase B: 1 l of acetonitrile; gradient: 0.0 min 98% A→0.2 min 98% A→3.0 min 5% A→4.5 min 5% A; oven: 40° C.; flow rate: 1.75 ml/min; UV detection: 210 nm.

Method 20 (preparative HPLC): Column: Chromatorex C18, 10 μm, 250 mm×30 mm. Mobile phase A: water, mobile phase B: methanol; flow rate: 75 ml/min; programme: 0 to 4.25 min: 60% A/40% B; 4.25 to 4.50 min: gradient to 60% B; 4.50 min to 9.99 min: gradient to 80% B; 9.99 to 12.40 min: gradient to 100% B; 12.40 to 17.21 min: 100% B; 17.21 to 17.46 min: gradient to 40% B; 17.46 to 18.22 min (end): 60% A/40% B.

Starting Materials and Intermediates

Example 1A 1,3,3-Trimethyl-5-nitro-1,3-dihydro-2H-indol-2-one

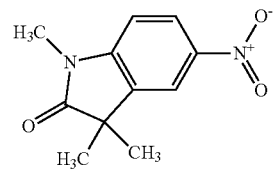 [SMILES: CN1C(=O)C(C)(C)c2cc([N+](=O)[O-])ccc21]

2.44 g (13.96 mmol) of 1,3,3-trimethyl-1,3-dihydro-2H-indol-2-one [preparation see: Journal of Organic Chemistry, 2000, vol. 65, 24, p. 8317-8325] were initially charged in 12 ml of acetic acid, 0.96 ml (13.96 mmol) of nitric acid (65%) was then added dropwise at RT and the reaction mixture was stirred at RT for 2 weeks. The reaction mixture was added to ice-water, and the solid formed was filtered off with suction, washed with water and dried at 50° C. under reduced pressure. This gave 2.32 g (72% of theory) of the title compound.

LC-MS (Method 1): $R_t$=0.89 min; MS (ESIpos): m/z=221 (M+H)$^+$.

$^1$H-NMR (400 MHz, DMSO-d$_6$): δ [ppm]=1.35 (s, 6H), 3.22 (s, 3H), 7.25 (d, 1H), 8.26 (dd, 1H), 8.33 (d, 1H).

Example 2A

5-Amino-1,3,3-trimethyl-1,3-dihydro-2H-indol-2-one

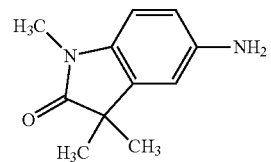

2.32 g (10.56 mmol) of 1,3,3-trimethyl-5-nitro-1,3-dihydro-2H-indol-2-one from Example 1A were initially charged in 71.5 ml of ethanol, 330 mg (0.32 mmol) of palladium (10% on activated carbon) were added and the mixture was hydrogenated at hydrogen standard pressure for 2 days. Subsequently, the reaction mixture was filtered through kieselguhr, the residue was washed with ethanol and the filtrate was concentrated. The residue was stirred with a little ethanol, filtered off, washed with a little ethanol, filtered off with suction and dried. This gave 1.95 g (93% of theory) of the title compound.

LC-MS (Method 4): $R_t$=0.76 min; MS (ESIpos): m/z=191 (M+H)$^+$.

$^1$H-NMR (400 MHz, DMSO-d$_6$): δ [ppm]=1.20 (s, 6H), 3.04 (s, 3H), 4.70-4.80 (m, 2H), 6.46 (dd, 1H), 6.58 (d, 1H), 6.67 (d, 1H).

Example 3A

Ethyl 2,4-dioxo-1-[4-(2-oxoimidazolidin-1-yl)phenyl]-1,2,3,4-tetrahydropyrimidine-5-carboxylate

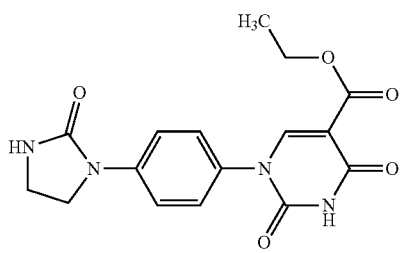 [SMILES: CCOC(=O)c1cn(-c2ccc(N3CCNC3=O)cc2)c(=O)[nH]c1=O]

15.96 g (61.6 mmol) of ethyl 3-ethoxy-2-[(ethoxycarbonyl)carbamoyl]acrylate (for preparation see: Senda, Shigeo; Hirota, Kosaku; Notani, Jiyoji, Chemical & Pharmaceutical Bulletin (1972), 20(7), 1380-8) and 12.0 g (67.7 mmol) of 1-(4-aminophenyl)imidazolidin-2-one (for preparation see: P. Stabile et al., Tetrahedron Letters 2010, 51 (24), 3232-3235) in 724 ml of ethanol were heated at reflux with stirring for two hours. The mixture was allowed to cool to 20° C., 6.91 g (61.6 mmol) of potassium tert-butoxide were added and the mixture was stirred at 20° C. for a further 18 hours. 1000 ml of water were added and the mixture was acidified to pH 3 with 1N aqueous hydrochloric acid. The solid formed was filtered off, washed with water (200 ml), ethyl acetate (100 ml) and diethyl ether (100 ml) and dried under high vacuum. This gave 13.54 g (54% of theory) of the title compound.

LC-MS (Method 1): $R_t$=0.62 min; m/z=345 (M+H)$^+$.
$^1$H-NMR (400 MHz, DMSO-$d_6$): δ=1.21 (t, 3H), 3.44 (m, 2H), 3.88 (m, 2H), 4.19 (q, 2H), 7.10 (s, 1H), 7.40 (d, 2H), 7.65 (d, 2H), 8.23 (s, 1H), 11.65 (br. s, 1H).

Example 4A

Ethyl 2,4-dioxo-1-[4-(2-oxo-1,3-oxazolidin-3-yl)phenyl]-1,2,3,4-tetrahydropyrimidine-5-carboxylate

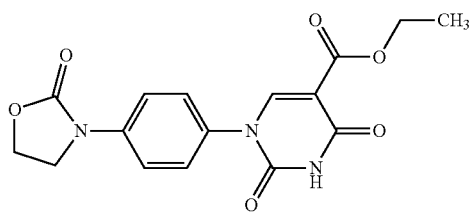 [SMILES: CCOC(=O)c1cn(-c2ccc(N3CCOC3=O)cc2)c(=O)[nH]c1=O]

3.02 g (17 mmol) of 3-(4-aminophenyl)-1,3-oxazolidin-2-one (preparation: see WO2010/019903, p. 222, Method 38; or Farmaco Sci. Ed. (1969), 179) and 4.0 g (15.4 mmol) of ethyl 3-ethoxy-2-[(ethoxycarbonyl)carbamoyl]acrylate (for preparation see: Senda, Shigeo; Hirota, Kosaku; Notani, Jiyoji, Chemical & Pharmaceutical Bulletin (1972), 20(7), 1380-8) in 170 ml of ethanol were heated at reflux for 2 h. After cooling to RT, 1.73 g (15.4 mmol) of potassium tert-butoxide were added and the mixture was stirred first at RT overnight and then at 50° C. for 5 h. The reaction mixture was poured into 1.4 l of 1N aqueous hydrochloric acid and the solid formed was isolated by filtration. The solid was stirred with diethyl ether and then dried under high vacuum. This gave 4.2 g (66% of theory, purity 92%) of the title compound.

LC-MS (Method 1): $R_t$=0.59 min; m/z=346 (M+H)$^+$.
$^1$H-NMR (400 MHz, DMSO-$d_6$): δ=1.22 (t, 3H), 4.06-4.14 (m, 2H), 4.17 (q, 2H), 4.43-4.51 (m, 2H), 7.51 (d, 2H), 7.68 (d, 2H), 8.26 (s, 1H), 11.69 (s, 1H).

Example 5A

Ethyl 1-(3-methyl-2-oxo-2,3-dihydro-1,3-benzoxazol-6-yl)-2,4-dioxo-1,2,3,4-tetrahydropyrimidine-5-carboxylate

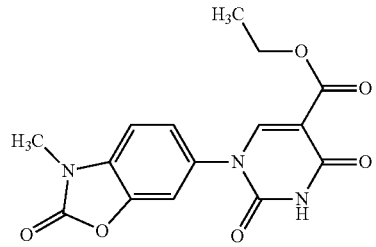 [SMILES: CCOC(=O)c1cn(-c2ccc3c(c2)oc(=O)n3C)c(=O)[nH]c1=O]

40.0 g (243.7 mmol) of 6-amino-3-methyl-1,3-benzoxazol-2(3H)-one were initially charged in 2.5 l of ethanol, and 63.2 g (243.7 mmol) ethyl 3-ethoxy-2-[(ethoxycarbonyl)carbamoyl]acrylate (for preparation see: Senda, Shigeo; Hirota, Kosaku; Notani, Jiyoji, Chemical & Pharmaceutical Bulletin (1972), 20(7), 1380-8) were added. After a few minutes, a thick suspension formed. This mixture was heated at reflux temperature for 1.5 h. After cooling to about 60° C., 27.3 g (243.7 mmol) of potassium tert-butoxide were added and the reaction mixture was stirred further at reflux temperature for 4.5 h. The mixture was cooled to about 60 C and then stirred into 10 l of cooled 1N aqueous hydrochloric acid. The solid was filtered off with suction, washed with water and dried in a vacuum drying cabinet at 70° C. overnight. This gave 64.0 g (79% of theory) of the title compound.

LC-MS (Method 1): $R_t$=0.59 min; MS (ESIpos): m/z=332 (M+H)$^+$.
$^1$H-NMR (400 MHz, DMSO-$d_6$): δ [ppm]=1.22 (t, 3H), 3.38 (s, 3H), 4.17 (q, 2H), 7.38 (s, 2H), 7.59 (s, 1H), 8.26 (s, 1H), 11.69 (s, 1H).

Example 6A

Ethyl 1-(4-methoxyphenyl)-2,4-dioxo-1,2,3,4-tetrahydropyrimidine-5-carboxylate

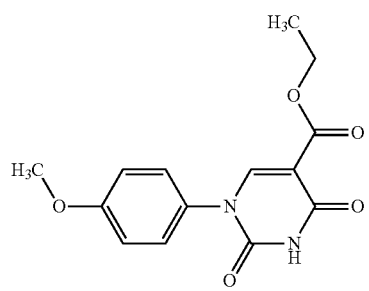 [SMILES: CCOC(=O)c1cn(-c2ccc(OC)cc2)c(=O)[nH]c1=O]

5.00 g (17.0 mmol) of diethyl {[(4-methoxyphenyl) amino]methylene}malonate (prepared according to Bioorg. Med. Chem. Lett., 16(4) 1010-1013; 2006) and 2.65 g (18.8 mmol) of chlorosulfonyl isocyanate in 30 ml of toluene were stirred in a microwave apparatus (CEM Discover, initial irradiation power 200 W, target temperature 120° C.) for 45 min. After concentration, the crude mixture was separated by chromatography on silica gel using dichloromethane/methanol mixtures with increasing methanol content (50:1-30:1-10:1). This gave, after concentration and drying of the appropriate fractions under reduced pressure, 1.14 g (23% of theory) of the target compound.

LC-MS (Method 2): $R_t$=0.86 min; m/z=291 (M+H)$^+$.

$^1$H-NMR (400 MHz, DMSO-$d_6$): δ=1.22 (t, 3H), 3.80 (s, 3H), 4.17 (q, 2H), 7.01-7.07 (m, 2H), 7.38-7.44 (m, 2H), 8.22 (s, 1H), 11.63 (br. s, 1H).

Example 7A

Ethyl 1-(3-methyl-2-oxo-2,3-dihydro-1,3-benzothiazol-6-yl)-2,4-dioxo-1,2,3,4-tetrahydropyrimidine-5-carboxylate

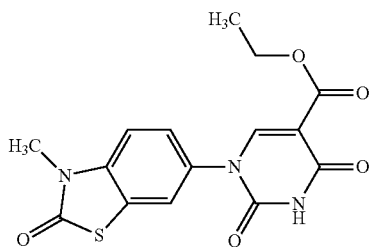 [SMILES: CCOC(=O)c1cn(-c2ccc3c(c2)sc(=O)n3C)c(=O)[nH]c1=O]

450 mg (2.50 mmol) of 6-amino-3-methyl-1,3-benzothiazol-2(3H)-one (J. Het. Chem. 1992, 29 (5), 1069-1076, Example 8b) and 647 mg (2.50 mmol) of ethyl 3-ethoxy-2-[(ethoxycarbonyl)carbamoyl]acrylate were initially charged in 19 ml of ethanol and the mixture was heated to reflux for 2 h. After cooling to RT, 280 mg (2.50 mmol) of potassium tert-butoxide were added and the reaction mixture was stirred further at RT overnight. For work-up, the reaction mixture was diluted with water and acidified with 1N aqueous hydrochloric acid, and the solid formed was filtered off. The solid was washed with water and ethyl acetate, and dried under reduced pressure at 50° C. overnight. This gave 736 mg (85% of theory) of the target compound.

LC-MS (Method 1): $R_t$=0.70 min; MS (ESIpos): m/z=348 (M+H)$^+$.

$^1$H-NMR (400 MHz, DMSO-$d_6$): δ [ppm]=1.22 (t, 3H), 3.45 (s, 3H), 4.17 (q, 2H), 7.42-7.47 (m, 1H), 7.51-7.55 (m, 1H), 7.83-7.86 (m, 1H), 8.32 (s, 1H), 11.71 (s, 1H).

Example 8A

Ethyl 2,4-dioxo-1-(1,3,3-trimethyl-2-oxo-2,3-dihydro-1H-indol-5-yl)-1,2,3,4-tetrahydropyrimidine-5-carboxylate

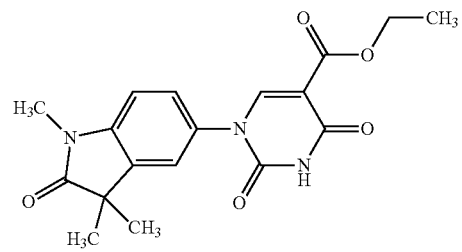 [SMILES: CCOC(=O)c1cn(-c2ccc3c(c2)C(C)(C)C(=O)N3C)c(=O)[nH]c1=O]

Preparation and purification of the target compound were analogous to Example 7A. Starting with 1.95 g (10.26 mmol) of 5-amino-1,3,3-trimethyl-1,3-dihydro-2H-indol-2-one from Example 2A and 2.66 g (10.26 mmol) of ethyl 3-ethoxy-2-[(ethoxycarbonyl)carbamoyl]acrylate, 2.84 g (77% of theory) of the title compound were obtained.

LC-MS (Method 4): $R_t$=1.62 min; MS (ESIpos): m/z=358 (M+H)$^+$.

$^1$H-NMR (400 MHz, DMSO-$d_6$): δ [ppm]=1.22 (t, 3H), 1.29 (s, 6H), 3.17 (s, 3H), 4.17 (q, 2H), 7.13 (d, 1H), 7.40 (dd, 1H), 7.51 (d, 1H), 8.25 (s, 1H), 11.65-11.71 (m, 1H).

Example 9A

Ethyl 1-(1-methyl-1H-benzimidazol-5-yl)-2,4-dioxo-1,2,3,4-tetrahydropyrimidine-5-carboxylate

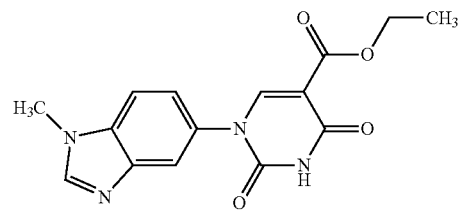 [SMILES: CCOC(=O)c1cn(-c2ccc3c(c2)ncn3C)c(=O)[nH]c1=O]

1.76 g (6.79 mmol) of ethyl 3-ethoxy-2-[(ethoxycarbonyl)carbamoyl]acrylate and 1.00 g (6.79 mmol) of 1-methyl-1H-benzimidazol-5-amine [for preparation see: US 2008/0090856, Ex. B23] in 51 ml of ethanol were heated to reflux for 2 h. Thereafter, at RT, 0.76 g (6.79 mmol) of potassium tert-butoxide were added and the reaction mixture was heated to reflux for a further 3 h. Water was added, and the reaction mixture was acidified with 1N aqueous hydrochloric acid. The aqueous phase was concentrated, dichloromethane/methanol (1:1) was added and the solid formed was filtered off. The filtrate was concentrated, MTBE/ethyl acetate (1:1) was added, and the solid formed was filtered off, washed with ethyl acetate and then dried at 50° C. under reduced pressure. This gave 1.55 g (73% of theory) of the title compound.

LC-MS (Method 4): $R_t$=1.00 min; MS (ESIpos): m/z=315 (M+H)$^+$.

$^1$H-NMR (400 MHz, DMSO-d$_6$): δ [ppm]=1.22 (t, 3H), 4.03 (s, 3H), 4.18 (q, 2H), 7.62-7.68 (m, 1H), 7.94-8.00 (m, 1H), 8.00-8.03 (m, 1H), 8.35 (s, 1H), 9.24 (br.s, 1H), 11.73 (s, 1H).

Example 10A

5-Amino-1,3-dimethyl-1,3-dihydro-2H-benzimidazol-2-one hydrochloride

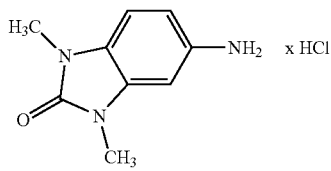

33.2 g (160 mmol) of 1,3-dimethyl-5-nitro-1,3-dihydro-2H-benzimidazol-2-one (preparation: see WO 2007/120339, Example 2, page 33) in 1790 ml of ethanol (only partly dissolved) were hydrogenated in the presence of 8.8 g of palladium catalyst (10% on activated carbon, moistened with 50% water) at RT and hydrogen standard pressure. After completion of conversion (6 h), the catalyst was removed by filtration through kieselguhr. 45 ml of a hydrogen chloride solution (4N in dioxane) were added to the filtrate, and the mixture was concentrated to dryness on a rotary evaporator. The residue was dried under high vacuum. This gave 31.8 g (91% of theory) of the title compound.

LC-MS (Method 1): R$_t$=0.18 min; m/z=178 (M+H)$^+$.

$^1$H-NMR (400 MHz, DMSO-d$_6$): δ [ppm]=3.33 (s, 3H), 3.34 (s, 3H), 7.06-7.15 (m, 2H), 7.23 (d, 1H), 10.29 (br.s, 3H).

Example 11A

Ethyl 1-(1,3-dimethyl-2-oxo-2,3-dihydro-1H-benzimidazol-5-yl)-2,4-dioxo-1,2,3,4-tetrahydropyrimidine-5-carboxylate

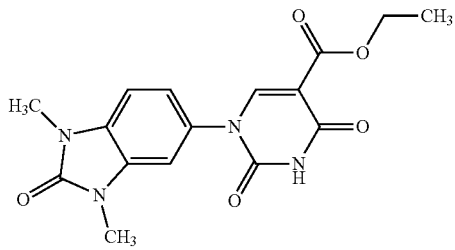 [SMILES: CCOC(=O)c1cn(-c2ccc3c(c2)n(C)c(=O)n3C)c(=O)[nH]c1=O]

52.80 g (247.1 mmol) of the compound from Example 10A and 64.07 g (247.1 mmol) ethyl 3-ethoxy-2-[(ethoxycarbonyl)carbamoyl]acrylate (for preparation see: Senda, Shigeo; Hirota, Kosaku; Notani, Jiyoji, Chemical & Pharmaceutical Bulletin (1972), 20(7), 1380-8) were initially charged in 2 l of ethanol, and 51.7 ml (370.7 mmol) of triethylamine were added. The thick suspension formed was heated to reflux temperature for 1.5 h, forming a clear solution. After cooling to about 60° C., 27.73 g (247.1 mmol) of potassium tert-butoxide were added. The reaction mixture was heated again to reflux temperature and stirred at this temperature for a further 7 h. After cooling to RT, about half the solvent was removed on a rotary evaporator. The reaction mixture was then poured into 7.5 l of 1N hydrochloric acid. The solid formed was filtered off, washed with 800 ml of water and dried under high vacuum. This gave 71.7 g (85% of theory) of the title compound.

LC-MS (Method 1): R$_t$=0.63 min; m/z=345 (M+H)$^+$.

$^1$H-NMR (400 MHz, DMSO-d$_6$): δ [ppm]=1.22 (t, 3H), 3.30 (s, 3H), 3.37 (s, 3H), 4.17 (q, 2H), 7.19 (dd, 1H), 7.25 (d, 1H), 7.37 (d, 1H), 8.26 (s, 1H).

Example 12A

Ethyl 3-[2-methyl-3-(trifluoromethyl)benzyl]-2,4-dioxo-1-[4-(2-oxoimidazolidin-1-yl)phenyl]-1,2,3,4-tetrahydropyrimidine-5-carboxylate

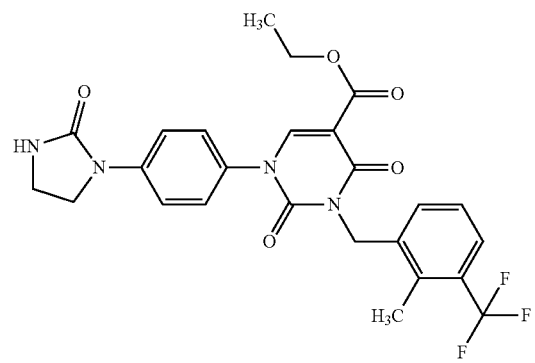 [SMILES: CCOC(=O)c1cn(-c2ccc(N3CCNC3=O)cc2)c(=O)n(Cc2cccc(C(F)(F)F)c2C)c1=O]

A mixture of 400 mg (1.16 mmol) of ethyl 2,4-dioxo-1-[4-(2-oxoimidazolidin-1-yl)phenyl]-1,2,3,4-tetrahydropyrimidine-5-carboxylate from Example 3A, 353 mg (1.39 mmol) of 2-methyl-3-(trifluoromethyl)benzyl bromide, 321 mg (2.32 mmol) of potassium carbonate and 193 mg (1.16 mmol) of potassium iodide in 16 ml of acetonitrile was stirred at 60° C. for 18 hours. The mixture was then cooled to 20° C., and 50 ml of water were added. The product formed was filtered off with suction, washed with a little diethyl ether and dried under high vacuum. 537 mg (89% of theory) of the target compound were obtained.

LC-MS (Method 2): R$_t$=1.05 min; m/z=517 (M+H)$^+$.

$^1$H-NMR (400 MHz, DMSO-d$_6$): δ=1.22 (t, 3H), 2.48 (s, 3H), 3.42 (m, 2H), 3.87 (m, 2H), 4.19 (q, 2H), 5.08 (s, 2H), 7.08 (s, 1H), 7.30-7.40 (m, 2H), 7.46 (d, 2H), 7.59 (d, 1H), 7.68 (d, 2H), 8.39 (s, 1H).

Example 13A

Ethyl 3-[2-methyl-3-(trifluoromethyl)benzyl]-2,4-dioxo-1-[4-(2-oxo-1,3-oxazolidin-3-yl)phenyl]-1,2,3,4-tetrahydropyrimidine-5-carboxylate

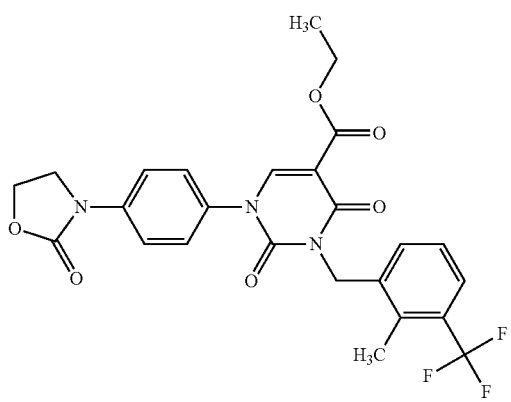 [SMILES: CCOC(=O)c1cn(-c2ccc(N3CCOC3=O)cc2)c(=O)n(Cc2cccc(C(F)(F)F)c2C)c1=O]

The preparation was carried out analogously to Example 12A from 200 mg (0.58 mmol) of ethyl 2,4-dioxo-1-[4-(2-oxo-1,3-oxazolidin-3-yl)phenyl]-1,2,3,4-tetrahydropyrimidine-5-carboxylate from Example 4A and 146.6 mg (0.58 mmol) of 2-methyl-3-(trifluoromethyl)benzyl bromide. Yield: 37 mg (12% of theory).

LC-MS (Method 4): $R_t$=2.36 min; m/z=518 (M+H)$^+$.

$^1$H-NMR (400 MHz, DMSO-$d_6$): δ=1.23 (t, 3H), 2.45 (s, 3H), 4.10 (m, 2H), 4.20 (q, 2H), 4.45 (m, 2H), 5.05 (s, 2H), 7.30-7.40 (m, 2H), 7.52-7.62 (m, 3H), 7.70 (d, 2H), 8.41 (s, 1H).

Example 14A

Ethyl 1-(3-methyl-2-oxo-2,3-dihydro-1,3-benzoxazol-6-yl)-2,4-dioxo-3-[(1R)-4-(trifluoromethyl)-2,3-dihydro-1H-inden-1-yl]-1,2,3,4-tetrahydropyrimidine-5-carboxylate (R Enantiomer)

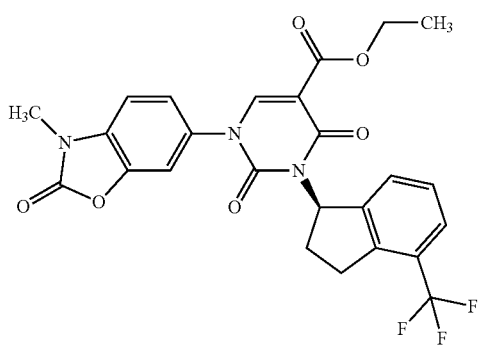 [SMILES: CCOC(=O)c1cn(-c2ccc3c(c2)oc(=O)n3C)c(=O)n([C@@H]2CCc3c2cccc3C(F)(F)F)c1=O]

A solution of 5.0 g (15.1 mmol) of ethyl 1-(3-methyl-2-oxo-2,3-dihydro-1,3-benzoxazol-6-yl)-2,4-dioxo-1,2,3,4-tetrahydropyrimidine-5-carboxylate from Example 5A, 6.73 g (25.7 mmol) of triphenylphosphine and 3.66 g (18.1 mmol) of (1S)-4-(trifluoromethyl)indan-1-ol was initially charged under argon in 240 ml of DMF/THF 2:1 (v/v) and cooled to −15° C. 4.76 ml (24.15 mmol) of diisopropyl azodicarboxylate was slowly added dropwise at such a rate that the temperature of the reaction mixture did not rise above −10° C. At the end of the addition, the mixture was stirred at −10° C. for another 1 h, then warmed to RT and poured onto 1.3 l of water. The mixture was extracted twice with 300 ml each time of ethyl acetate. The combined organic phases were washed with a saturated aqueous sodium chloride solution, dried over magnesium sulfate and freed of the solvent on a rotary evaporator. The residue (18 g) was purified in two chromatography steps: first using a 200 g silica gel column with dichloromethane/acetone 97.5:2.5 as the mobile phase. The resulting product-containing fractions were concentrated and the residue was applied again to a 200 g silica gel column. 2.5 l of cyclohexane/ethyl acetate 1:1 as mobile phase were used to elute further impurities, then the desired product was eluted from the column with dichloromethane/methanol 95:5. This gave 3.40 g (44% of theory) of the title compound in 95% purity (the NMR showed about 5% ethyl acetate). A further 920 mg were obtainable by a new purification of a mixed fraction. Total yield: 4.32 g (56% of theory).

LC-MS (Method 1): $R_t$=1.15 min; m/z=516 (M+H)$^+$.

$^1$H-NMR (400 MHz, CD$_2$Cl$_2$): δ [ppm]=1.31 (t, 3H), 2.37-2.49 (m, 1H), 2.59 (dtd, 1H), 3.14 (dt, 1H), 3.40 (s, 3H), 3.42-3.53 (m, 1H), 4.29 (q, 2H), 6.54-6.68 (m, 1H), 7.06 (d, 1H), 7.17 (d, 1H), 7.22 (s, 1H), 7.26-7.36 (m, 2H), 7.49 (d, 1H), 8.28 (s, 1H).

Example 15A

Ethyl 1-(1,3-dimethyl-2-oxo-2,3-dihydro-1H-benzimidazol-5-yl)-2,4-dioxo-3-[(1R)-4-(trifluoromethyl)-2,3-dihydro-1H-inden-1-yl]-1,2,3,4-tetrahydropyrimidine-5-carboxylate (R Enantiomer)

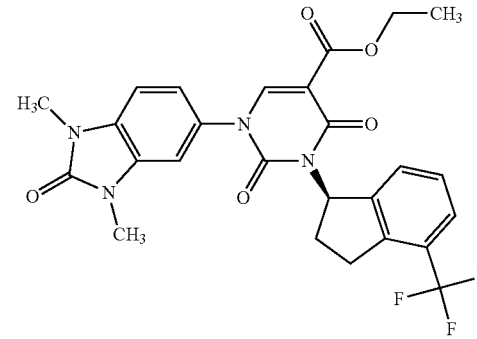

3.05 g (8.86 mmol) of ethyl 1-(1,3-dimethyl-2-oxo-2,3-dihydro-1H-benzimidazol-5-yl)-2,4-dioxo-1,2,3,4-tetrahydropyrimidine-5-carboxylate from Example 11A, 2.15 g (10.63 mmol) of (1S)-4-(trifluoromethyl)indan-1-ol and 6.97 g (26.6 mmol) of triphenylphosphine were initially charged under argon in THF/DMF 1:1 (1.7 l) and cooled to −15° C. 3.48 ml (17.71 mmol) of diisopropyl azodicarboxylate were added gradually. Subsequently, the reaction mixture was stirred at RT for another 30 min. While cooling with ice, a further 0.8 equivalent (1.39 ml, 6.86 mmol) of diisopropyl azodicarboxylate was added dropwise and the reaction mixture was stirred at RT for 1 h. The reaction mixture was cooled to −40° C., 1M hydrochloric acid was added, and the mixture was diluted with ethyl acetate and stirred vigorously for a few minutes. The organic phase was separated, washed twice with 1M sodium carbonate solution and once with saturated sodium chloride solution, dried over sodium sulfate and concentrated on a rotary evaporator. MTBE was added to the residue and the mixture was stirred at RT overnight, then stirred with ice bath cooling for 20 min. The solid formed was filtered off with suction and washed with cold MTBE. The whole filtrate was concentrated and purified by means of preparative HPLC (Method 5). This gave 2.90 g (62% of theory) of the title compound.

LC-MS (Method 1): $R_t$=1.05 min; m/z=529 (M+H)$^+$.

$^1$H-NMR (400 MHz, CD$_2$Cl$_2$): δ=1.36 (t, 3H), 2.42-2.55 (m, 1H), 2.57-2.71 (m, 1H), 3.12-3.24 (m, 1H), 3.43 (s, 3H), 3.43-3.58 (m, 1H), 3.45 (s, 3H), 4.33 (q, 2H), 6.60-6.73 (m, 1H), 6.99 (s, 1H), 7.07 (s, 2H), 7.30-7.42 (m, 2H), 7.54 (d, 2H), 8.36 (s, 1H).

Example 16A

Ethyl 1-(3-methyl-2-oxo-2,3-dihydro-1,3-benzothiazol-6-yl)-2,4-dioxo-3-[(1R)-4-(trifluoromethyl)-2,3-dihydro-1H-inden-1-yl]-1,2,3,4-tetrahydropyrimidine-5-carboxylate (R Enantiomer)

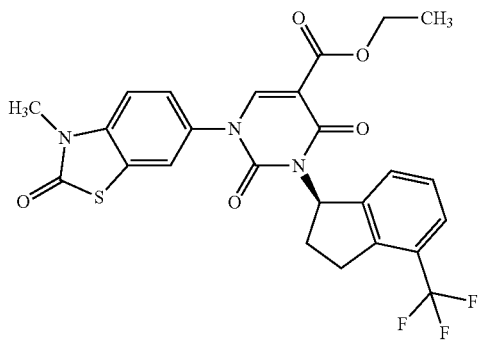 [SMILES: CCOC(=O)c1cn(-c2ccc3c(c2)sc(=O)n3C)c(=O)n([C@@H]2CCc3c2cccc3C(F)(F)F)c1=O]

8.00 g (23.03 mmol) of ethyl 1-(3-methyl-2-oxo-2,3-dihydro-1,3-benzothiazol-6-yl)-2,4-dioxo-1,2,3,4-tetrahydropyrimidine-5-carboxylate from Example 7A, 5.12 g (25.33 mmol) of (1S)-4-(trifluoromethyl)indan-1-ol and 10.27 g (39.15 mmol) of triphenylphosphine were initially charged in 317 ml of THF and 317 ml of DMF and cooled to 5° C. 7.25 ml (36.85 mmol) of diisopropyl azodicarboxylate were added in portions. The cooling bath was removed and the mixture was stirred at RT for 1 h. For workup, 200 ml of 1N hydrochloric acid were added and the mixture was stirred vigorously for 5 min. 400 ml of ethyl acetate were added. After stirring vigorously for 10 minutes, the organic phase was removed. The aqueous phase was extracted once more with 400 ml of ethyl acetate. The combined organic phases were washed twice with 100 ml each time of a saturated sodium carbonate solution, then with 100 ml of a saturated sodium chloride solution, then dried over sodium sulfate and concentrated on a rotary evaporator. 400 ml of MTBE were added to the residue, and the mixture was stirred while cooling with an ice bath for 30 min. The solid formed was filtered off with suction and washed twice with cold MTBE. The combined filtrates were concentrated and the residue was purified by means of flash chromatography (cyclohexane/ethyl acetate 1:2→1:4). The product thus obtained was recrystallized from acetonitrile and dried under high vacuum. This gave 6.3 g (50% of theory) of the title compound.

LC-MS (Method 1): $R_t$=1.18 min; m/z=532 (M+H)$^+$.

$^1$H-NMR (400 MHz, CD$_2$Cl$_2$): δ [ppm]=1.31 (t, 3H), 2.37-2.49 (m, 1H), 2.53-2.65 (m, 1H), 3.08-3.20 (m, 1H), 3.40-3.52 (m, 1H), 3.45 (s, 3H), 4.29 (q, 2H), 6.56-6.68 (m, 1H), 7.09-7.18 (m, 1H), 7.25-7.36 (m, 3H), 7.44 (s, 1H), 7.47-7.54 (m, 1H), 8.29 (s, 1H).

Example 17A

Ethyl 1-(1-methyl-1H-benzimidazol-5-yl)-3-[2-methyl-3-(trifluoromethyl)benzyl]-2,4-dioxo-1,2,3,4-tetrahydropyrimidine-5-carboxylate

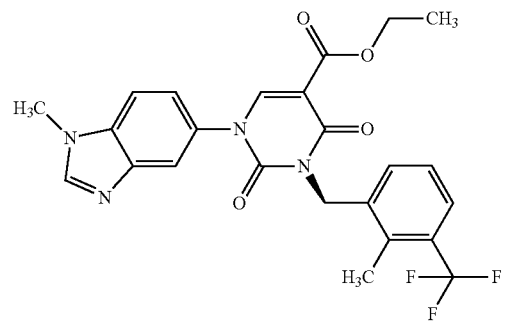

1.00 g (3.18 mmol) of ethyl 1-(1-methyl-1H-benzimidazol-5-yl)-2,4-dioxo-1,2,3,4-tetrahydropyrimidine-5-carboxylate from Example 9A were initially charged in DMF (8 ml), and 886 mg (3.50 mmol) of 1-(bromomethyl)-2-methyl-3-(trifluoromethyl)benzene, 879 mg (6.36 mmol) of potassium carbonate and 53 mg (0.32 mmol) of potassium iodide were added. Subsequently, the reaction mixture was left to stir at 60° C. for 5 h. The mixture cooled to RT, water was added and the precipitate was filtered off with suction, washed with water and ethanol/MTBE, and dried under reduced pressure at 50° C. This gave 1.06 g (68% of theory) of the title compound.

LC-MS (Method 1): $R_t$=0.93 min; m/z=487 (M+H)$^+$.

$^1$H-NMR (400 MHz, DMSO-d$_6$): δ [ppm]=1.23 (t, 3H), 2.46 (s, 3H), 3.89 (s, 3H), 4.19 (q, 2H), 5.09 (s, 2H), 7.32-7.46 (m, 3H), 7.60 (d, 1H), 7.71 (d, 1H), 7.89 (d, 1H), 8.33 (s, 1H), 8.46 (s, 1H).

Example 18A

Ethyl 3-[2-methyl-3-(trifluoromethyl)benzyl]-2,4-dioxo-1-(1,3,3-trimethyl-2-oxo-2,3-dihydro-1H-indol-5-yl)-1,2,3,4-tetrahydropyrimidine-5-carboxylate

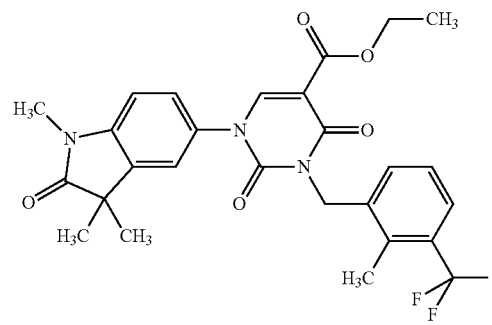

Preparation and purification of the title compound were analogous to Example 17A. Starting with 500 mg (1.39 mmol) of ethyl 2,4-dioxo-1-(1,3,3-trimethyl-2-oxo-2,3-dihydro-1H-indol-5-yl)-1,2,3,4-tetrahydropyrimidine-5-carboxylate from Example 8A and 389 mg (1.53 mmol) of 1-(bromomethyl)-2-methyl-3-(trifluoromethyl)benzene, 571 mg (77% of theory) of the title compound were obtained.

LC-MS (Method 1): $R_t$=1.11 min; m/z=530 (M+H)$^+$.

$^1$H-NMR (400 MHz, DMSO-d$_6$): δ [ppm]=1.29 (s, 6H), 2.46 (s, 3H), 3.18 (s, 3H), 3.30 (s, 3H), 4.20 (q, 2H), 5.08 (s, 2H), 7.15 (d, 1H), 7.34-7.39 (m, 2H), 7.44-7.49 (m, 1H), 7.53-7.56 (m, 1H), 7.58-7.63 (m, 1H), 8.42 (s, 1H).

Example 19A

Ethyl 1-(1,3-dimethyl-2-oxo-2,3-dihydro-1H-benzimidazol-5-yl)-3-[2-methyl-3-(trifluoromethyl)benzyl]-2,4-dioxo-1,2,3,4-tetrahydropyrimidine-5-carboxylate

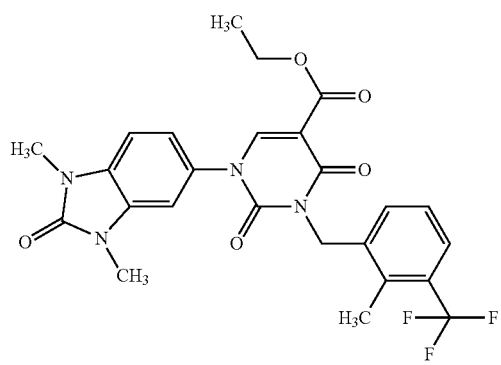 [SMILES: CCOC(=O)c1cn(-c2ccc3c(c2)n(C)c(=O)n3C)c(=O)n(Cc2cccc(C(F)(F)F)c2C)c1=O]

To a solution of 14.95 g (43.42 mmol) of ethyl 1-(1,3-dimethyl-2-oxo-2,3-dihydro-1H-benzimidazol-5-yl)-2,4-dioxo-1,2,3,4-tetrahydropyrimidine-5-carboxylate from Example 3A in DMF (200 ml) were added 12.00 g (86.84 mmol) of potassium carbonate, 12.09 g (47.76 mmol) of 2-methyl-3-(trifluoromethyl)benzyl bromide and 0.721 g (4.34 mmol) of potassium iodide, and the reaction mixture was left to stir at 80° C. for 3 h. Subsequently, the mixture was cooled to RT, water was added and the precipitate formed was filtered off. The solid was washed successively with water and MTBE, and dried under reduced pressure at 50° C. This gave 21.04 g (94% of theory) of the title compound.

LC-MS (Method 1): $R_t$=1.07 min; m/z=517 (M+H)$^+$.

$^1$H-NMR (400 MHz, DMSO-d$_6$): δ [ppm]=1.23 (t, 3H), 2.46 (s, 3H), 3.34 (s, 3H), 3.37 (s, 3H), 4.20 (q, 2H), 5.09 (s, 2H), 7.23-7.30 (m, 2H), 7.32-7.43 (m, 3H), 7.58-7.62 (m, 1H), 8.42 (s, 1H).

Example 20A

Ethyl 3-(2,3-dichlorobenzyl)-1-(4-methoxyphenyl)-2,4-dioxo-1,2,3,4-tetrahydropyrimidine-5-carboxylate

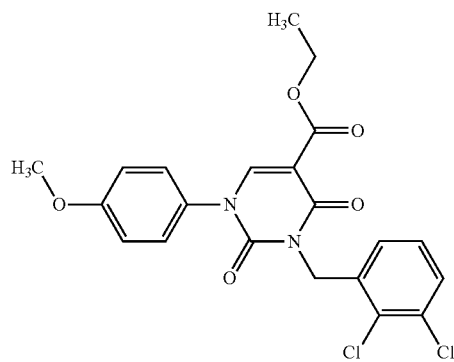 [SMILES: CCOC(=O)c1cn(-c2ccc(OC)cc2)c(=O)n(Cc2cccc(Cl)c2Cl)c1=O]

95 mg (0.69 mmol) of potassium carbonate and 91 mg (0.38 mmol) of 2,3-dichlorobenzyl bromide were added to 100 mg (0.34 mmol) of ethyl 1-(4-methoxyphenyl)-2,4-dioxo-1,2,3,4-tetrahydropyrimidine-5-carboxylate from Example 6A in acetonitrile, and the reaction mixture was stirred at 60° C. overnight. The mixture was concentrated and the residue was purified by filtration through 500 mg of silica gel using cyclohexane/ethyl acetate in a ratio of 2:1. This gave, after concentration of the eluate and drying under reduced pressure, 137 mg (88% of theory) of the target compound.

LC-MS (Method 1): $R_t$=1.19 min; m/z=449 (M+H)$^+$.

$^1$H-NMR (400 MHz, DMSO-d$_6$): δ=1.23 (t, 3H), 3.81 (s, 3H), 4.20 (q, 2H), 5.09 (s, 2H), 7.04-7.09 (m, 2H), 7.21 (dd, 1H), 7.32 (t, 1H), 7.43-7.49 (m, 2H), 7.58 (dd, 1H), 8.39 (s, 1H).

Example 21A 3-(2,3-Dichlorobenzyl)-1-(4-methoxyphenyl)-2,4-dioxo-1,2,3,4-tetrahydropyrimidine-5-carboxylic acid

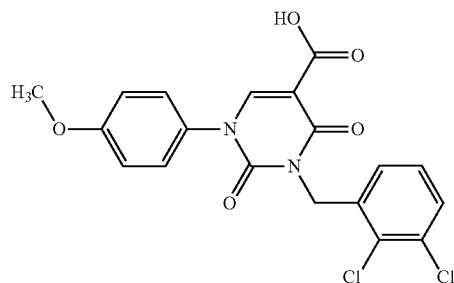 [SMILES: COc1ccc(-n2cc(C(=O)O)c(=O)n(Cc3cccc(Cl)c3Cl)c2=O)cc1]

135 mg (0.30 mmol) of ethyl 3-(2,3-dichlorobenzyl)-1-(4-methoxyphenyl)-2,4-dioxo-1,2,3,4-tetrahydropyrimidine-5-carboxylate from Example 20A in a mixture of 2.0 ml of acetic acid and 1.0 ml of concentrated hydrochloric acid were stirred at 110° C. overnight. Under reduced pressure, the reaction mixture was concentrated to about a third, and after addition of water a solid formed which was filtered off, washed with water and dried under reduced pressure. This gave 61 mg (48% of theory) of the target compound.

LC-MS (Method 2): $R_t$=1.28 min; m/z=421 (M+H)+.

$^1$H-NMR (400 MHz, DMSO-d$_6$): δ=3.81 (s, 3H), 5.12 (s, 2H), 7.03-7.09 (m, 2H), 7.24 (dd, 1H), 7.33 (t, 1H), 7.43-7.49 (m, 2H), 7.58 (dd, 1H), 8.41 (s, 1H), 12.69 (br. s., 1H).

Example 22A 1-(3-Methyl-2-oxo-2,3-dihydro-1,3-benzoxazol-6-yl)-2,4-dioxo-3-[(1R)-4-(trifluoromethyl)-2,3-dihydro-1H-inden-1-yl]-1,2,3,4-tetrahydropyrimidine-5-carboxylic acid (R Enantiomer)

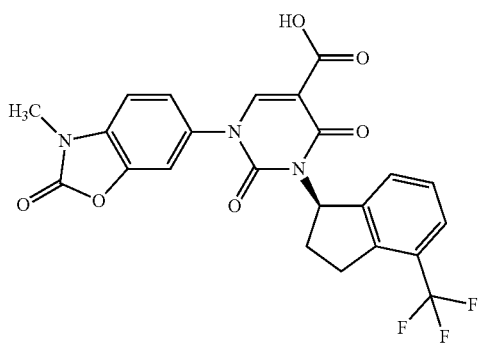 [SMILES: Cn1c(=O)oc2cc(-n3cc(C(=O)O)c(=O)n([C@@H]4CCc5c4cccc5C(F)(F)F)c3=O)ccc21]

3.40 g (6.60 mmol) of the compound from Example 14A in 44 ml of glacial acetic acid and 22 ml of concentrated hydrochloric acid were stirred at reflux temperature for 1 h. After cooling slightly (about 60° C.), the mixture was fully concentrated under reduced pressure. 50 ml of isopropanol were added to the amorphous residue and the mixture was heated to reflux for 15 min, in the course of which a solid formed. The suspension was then cooled to 10° C. and then the solid was filtered off with suction. The solid was washed twice with 15 ml each time of isopropanol, filtered off with suction and dried under HV. This gave 2.53 g (79% of theory) of the title compound.

LC-MS (Method 1): $R_t$=1.12 min; m/z=488 (M+H)+.

$^1$H-NMR (400 MHz, CD$_2$Cl$_2$): δ [ppm]=2.40-2.52 (m, 1H), 2.59-2.72 (m, 1H), 3.12-3.25 (m, 1H), 3.41 (s, 3H), 3.44-3.56 (m, 1H), 6.58-6.69 (m, 1H), 7.04-7.11 (m, 1H), 7.15-7.21 (m, 1H), 7.24 (br.s, 1H), 7.29-7.38 (m, 2H), 7.53 (s, 1H), 8.54 (s, 1H), 12.39 (br. s, 1H).

Specific rotation $β_D^{20}$=+135.3° (methanol, c=0.43).

Example 23A 1-(1,3-Dimethyl-2-oxo-2,3-dihydro-1H-benzimidazol-5-yl)-2,4-dioxo-3-[(1R)-4-(trifluoromethyl)-2,3-dihydro-1H-inden-1-yl]-1,2,3,4-tetrahydropyrimidine-5-carboxylic acid (R Enantiomer)

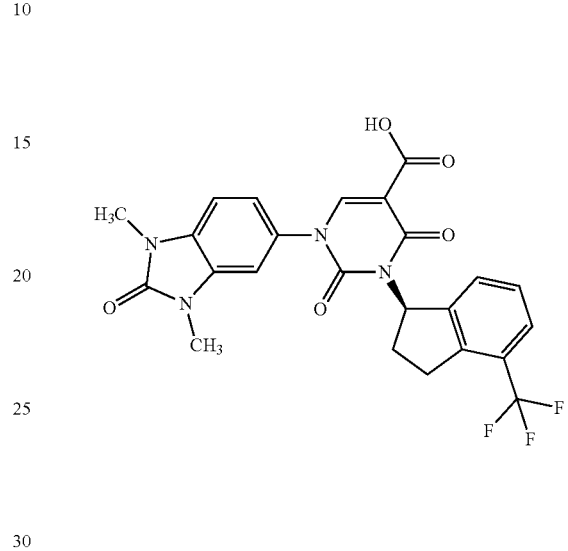

4.20 g (7.79 mmol) of ethyl 1-(1,3-dimethyl-2-oxo-2,3-dihydro-1H-benzimidazol-5-yl)-2,4-dioxo-3-[4-(trifluoromethyl)-2,3-dihydro-1H-inden-1-yl]-1,2,3,4-tetrahydropyrimidine-5-carboxylate from Example 15A were stirred with 40 ml of glacial acetic acid and 20 ml of conc. hydrochloric acid at reflux temperature for 1 h. The reaction mixture was cooled to RT, then diluted with 300 ml of water. The solid formed was filtered off with suction, washed with a little water and dried under HV. The solid thus obtained was stirred with 45 ml of toluene. At first it dissolved completely, but after a few minutes a crystalline solid formed. The mixture was cooled to 0° C. and stirred at this temperature for 30 min. Subsequently, the solid was filtered off, washed with 5 ml of toluene and dried under HV. This gave 3.17 g (81% of theory) of the title compound.

LC-MS (Method 1): $R_t$=1.06 min; m/z=501 (M+H)+.

$^1$H-NMR (400 MHz, DMSO-d$_6$): δ [ppm]=2.38-2.46 (m, 1H), 2.46-2.60 (m, 1H partially hidden under DMSO signal), 3.10 (dt, 1H), 3.23-3.35 (m, 1H partially hidden under DMSO-signal), 3.31 (s, 4H), 3.36 (s, 3H), 6.36-6.60 (m, 1H), 7.12-7.30 (m, 2H), 7.31-7.43 (m, 2H), 7.48-7.58 (m, 2H), 8.38 (s, 1H), 12.71 (br.s, 1H).

$^1$H-NMR (400 MHz, CD$_2$Cl$_2$): δ [ppm]=2.42-2.53 (m, 1H), 2.60-2.72 (m, 1H), 3.11-3.25 (m, 1H), 3.39 (s, 3H), 3.41 (s, 3H), 3.45-3.55 (m, 1H), 6.59-6.71 (m, 1H), 6.94 (br. s, 1H), 7.04 (s, 2H), 7.28-7.41 (m, 2H), 7.54 (d, 1H), 8.57 (s, 1H), 12.45 (br. S, 1H).

In an analogous experiment, it was possible to isolate a fraction with 99% purity. For this batch, the specific optical rotation measured was:

Specific optical rotation: $α_D^{20}$=+110.6°, (methanol, c=0.405 g/100 ml).

Example 24A 1-(3-Methyl-2-oxo-2,3-dihydro-1,3-benzothiazol-6-yl)-2,4-dioxo-3-[(1R)-4-(trifluoromethyl)-2,3-dihydro-1H-inden-1-yl]-1,2,3,4-tetrahydropyrimidine-5-carboxylic acid (R Enantiomer)

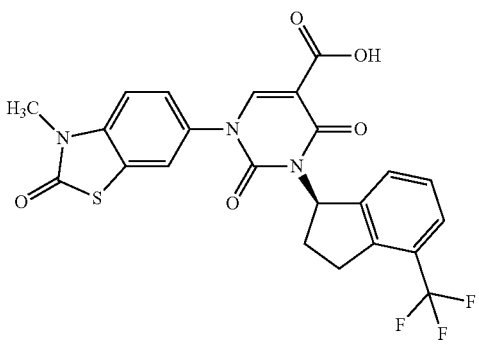 [SMILES: Cn1c(=O)sc2cc(-n3cc(C(=O)O)c(=O)n([C@@H]4CCc5c4cccc5C(F)(F)F)c3=O)ccc21]

6.20 g (11.3 mmol) of the compound from Example 16A in 150 ml of glacial acetic acid/conc. hydrochloric acid 2:1 were heated to 120° C. (bath temperature) for 1 h. After cooling to RT, the reaction mixture was poured into 1 l of ice-water. The product formed was filtered off with suction. The solid was stirred with diethyl ether, filtered off with suction again and dried under HV. This gave 5.04 g (88% of theory) of the title compound.

LC-MS (Method 1): $R_t$=1.14 min; m/z=504 (M+H)$^+$.

$^1$H-NMR (400 MHz, $CD_2Cl_2$): δ [ppm]=2.39-2.53 (m, 1H), 2.60-2.72 (m, 1H), 3.12-3.24 (m, 1H), 3.42-3.56 (m, 4H), 6.58-6.71 (m, 1H), 7.15 (d, 1H), 7.26-7.38 (m, 3H), 7.45 (s, 1H), 7.50-7.58 (m, 1H), 8.55 (s, 1H).

For further batches of the title compound, which have been prepared analogously, the following additional analytical data have been collected:

$α_D^{20}$ [chloroform, c=0.365]=+148.6°.

Example 25A

3-[2-Methyl-3-(trifluoromethyl)benzyl]-2,4-dioxo-1-[4-(2-oxoimidazolidin-1-yl)phenyl]-1,2,3,4-tetrahydropyrimidine-5-carboxylic acid

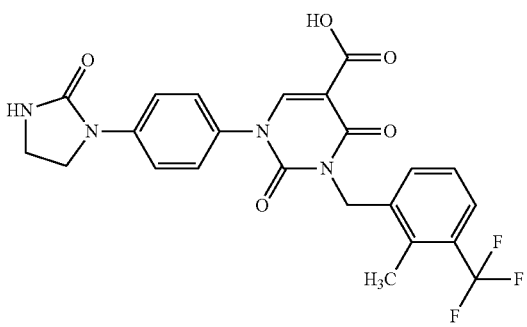 [SMILES: Cc1c(Cn2c(=O)c(C(=O)O)cn(-c3ccc(N4CCNC4=O)cc3)c2=O)cccc1C(F)(F)F]

532 mg (1.03 mmol) of ethyl 3-[2-methyl-3-(trifluoromethyl)benzyl]-2,4-dioxo-1-[4-(2-oxoimidazolidin-1-yl)phenyl]-1,2,3,4-tetrahydropyrimidine-5-carboxylate from Example 12A were dissolved in 14 ml of glacial acetic acid and 7 ml of conc. hydrochloric acid, and the mixture was stirred at 60° C. After HPLC confirmed complete conversion of the reaction (reaction time 5.5 hours), the mixture was diluted with 30 ml of water and the precipitate formed was filtered off with suction. The mixture was then purified by preparative HPLC (Method 11). This gave, after concentration of the product-containing fractions under reduced pressure, 338 mg (66% of theory) of the product.

LC-MS (Method 4): $R_t$=2.19 min; m/z=489 (M+H)$^+$.

$^1$H-NMR (400 MHz, DMSO-$d_6$): δ=2.45 (s, 3H), 3.44 (m, 2H), 3.9 (m, 2H), 5.1 (s, 2H), 7.08 (s, 1H), 7.32 (t, 1H), 7.38 (d, 1H), 7.45 (d, 2H), 7.60 (d, 1H), 7.65 (d, 2H), 8.42 (s, 1H), 12.70 (br. s, 1H).

Example 26A 1-(1,3-Dimethyl-2-oxo-2,3-dihydro-1H-benzimidazol-5-yl)-3-[2-methyl-3-(trifluoromethyl)benzyl]-2,4-dioxo-1,2,3,4-tetrahydropyrimidine-5-carboxylic acid

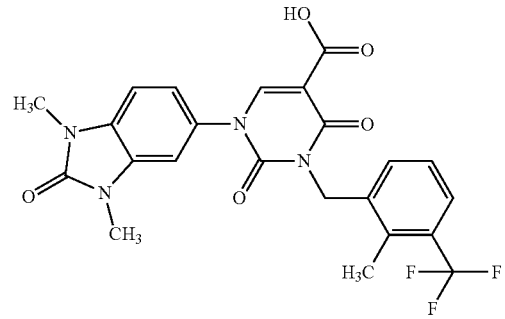 [SMILES: Cc1c(Cn2c(=O)c(C(=O)O)cn(-c3ccc4c(c3)n(C)c(=O)n4C)c2=O)cccc1C(F)(F)F]

5.60 g (10.84 mmol) of ethyl 1-(1,3-dimethyl-2-oxo-2,3-dihydro-1H-benzimidazol-5-yl)-3-[2-methyl-3-(trifluoromethyl)benzyl]-2,4-dioxo-1,2,3,4-tetrahydropyrimidine-5-carboxylate from Example 19A were initially charged in 78 ml of glacial acetic acid and 39 ml of conc. hydrochloric acid and stirred at 120° C. for 1 h. Subsequently, water was added to the mixture, which had cooled to RT, and the precipitate was filtered off with suction. The solid was washed successively with water and MTBE and then dried at 50° C. under reduced pressure. This gave 5.11 g (96% of theory) of the title compound.

LC-MS (Method 1): $R_t$=0.98 min; m/z=489 (M+H)$^+$.

$^1$H-NMR (400 MHz, DMSO-$d_6$): δ [ppm]=2.47 (s, 3H), 3.31 (s, 3H), 3.37 (s, 3H), 5.11 (s, 2H), 7.22-7.30 (m, 2H), 7.33-7.43 (m, 3H), 7.59-7.63 (m, 1H), 8.45 (s, 1H), 12.73 (br.s, 1H).

Example 27A 1-(1-Methyl-1H-benzimidazol-5-yl)-3-[2-methyl-3-(trifluoromethyl)benzyl]-2,4-dioxo-1,2,3,4-tetrahydropyrimidine-5-carboxylic acid

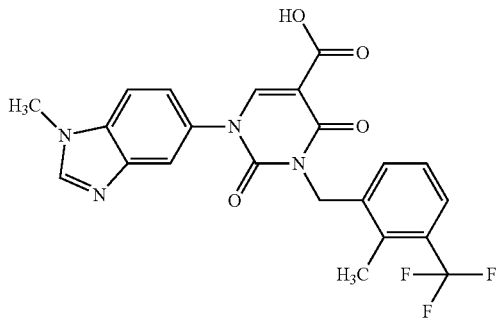 [SMILES: Cc1c(Cn2c(=O)c(C(=O)O)cn(-c3ccc4c(c3)ncn4C)c2=O)cccc1C(F)(F)F]

The preparation and purification of the title compound were in analogy to Example 26A. Starting with 170 mg (0.35 mmol) of ethyl 1-(1-methyl-1H-benzimidazol-5-yl)-3-[2-methyl-3-(trifluoromethyl)benzyl]-2,4-dioxo-1,2,3,4-tetrahydropyrimidine-5-carboxylate from Example 77, 124 mg (77% of theory) of the title compound were obtained.

LC-MS (Method 1): $R_t$=0.90 min; m/z=459 (M+H)$^+$.

$^1$H-NMR (400 MHz, DMSO-d$_6$): δ [ppm]=2.47 (s, 3H), 3.89 (s, 3H), 5.12 (s, 2H), 7.33-7.40 (m, 1H), 7.41-7.46 (m, 2H), 7.59-7.63 (m, 1H), 7.71 (d, 1H), 7.86-7.89 (m, 1H), 8.33 (s, 1H), 8.50 (s, 1H), 12.72 (br.s, 1H).

Example 28A

3-[2-methyl-3-(trifluoromethyl)benzyl]-2,4-dioxo-1-(1,3,3-trimethyl-2-oxo-2,3-dihydro-1H-indol-5-yl)-1,2,3,4-tetrahydropyrimidine-5-carboxylic acid

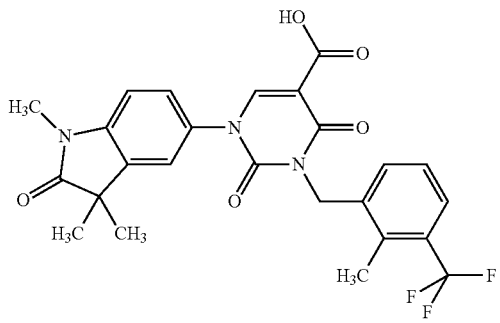 [SMILES: Cc1c(Cn2c(=O)c(C(=O)O)cn(-c3ccc4c(c3)C(C)(C)C(=O)N4C)c2=O)cccc1C(F)(F)F]

The preparation and purification of the title compound were in analogy to Example 26A. Starting with 200 mg (0.38 mmol) of ethyl 3-[2-methyl-3-(trifluoromethyl)benzyl]-2,4-dioxo-1-(1,3,3-trimethyl-2-oxo-2,3-dihydro-1H-indol-5-yl)-1,2,3,4-tetrahydropyrimidine-5-carboxylate from Example 53, 153 mg (80% of theory) of the title compound were obtained.

LC-MS (Method 1): $R_t$=1.07 min; m/z=502 (M+H)$^+$.

$^1$H-NMR (400 MHz, DMSO-d$_6$): δ [ppm]=1.29 (s, 6H), 2.47 (s, 3H), 3.17 (s, 3H), 5.11 (s, 2H), 7.15 (d, 1H), 7.32-7.42 (m, 2H), 7.46 (dd, 1H), 7.54 (d, 1H), 7.58-7.64 (m, 1H), 8.45 (s, 1H), 12.73 (br.s, 1H).

Example 29A

3-[2-Methyl-3-(trifluoromethyl)benzyl]-2,4-dioxo-1-[4-(2-oxo-1,3-oxazolidin-3-yl)phenyl]-1,2,3,4-tetrahydropyrimidine-5-carboxylic acid

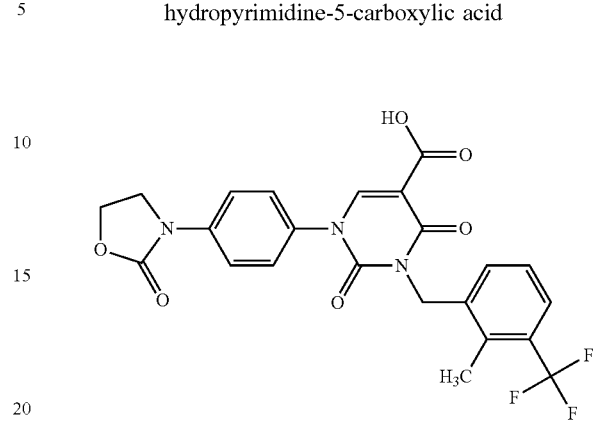

The preparation and purification were carried out analogously to Example 25A from 37 mg (0.07 mmol) of ethyl 3-[2-methyl-3-(trifluoromethyl)benzyl]-2,4-dioxo-1-[4-(2-oxo-1,3-oxazolidin-3-yl)phenyl]-1,2,3,4-tetrahydropyrimidine-5-carboxylate from Example 13A. Yield: 15 mg (42% of theory).

LC-MS (Method 1): $R_t$=1.08 min; m/z=490 (M+H)$^+$.

$^1$H-NMR (400 MHz, DMSO-d$_6$): δ=2.49 (s, 3H), 4.10 (m, 2H), 4.47 (m, 2H), 5.10 (s, 2H), 7.32 (t, 1H), 7.40 (d, 1H), 7.51-7.62 (m, 3H), 7.70 (d, 2H), 8.44 (s, 1H), 12.7 (br. s, 1H).

Example 30A 1-(1,3-Dimethyl-2-oxo-2,3-dihydro-1H-benzimidazol-5-yl)-2,4-dioxo-1,2,3,4-tetrahydropyrimidine-5-carbonitrile

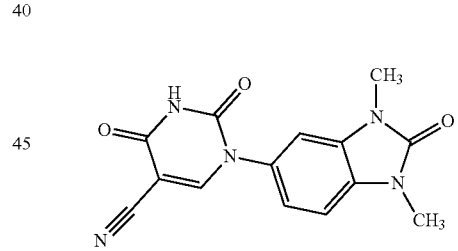

A mixture of 1.00 g (4.71 mmol) of ethyl (2-cyano-3-ethoxyprop-2-enoyl)carbamate (for preparation see: Senda, Shigeo, Hirota, Kosaku, Notani, Jiyoji; Chemical & Pharmaceutical Bulletin (1972), 20(7), 1380-8) and 835 mg (4.71 mmol) of 5-amino-1,3-dimethyl-1,3-dihydro-2H-benzimidazol-2-one in 5 ml of acetonitrile and 10 ml of DMF was stirred at reflux temperature overnight. After cooling to RT, the mixture was diluted with 150 ml of diethyl ether and the precipitate was filtered off. The filter residue was stirred with 10 ml of methanol, and the solid was filtered off, washed with a little methanol and ether and dried under high vacuum. This gave 703 mg (45% of theory) of the title compound.

LC-MS (Method 1): $R_t$=0.53 min; m/z=298 (M+H)$^+$.

$^1$H-NMR (400 MHz, DMSO-d$_6$): δ [ppm]=3.30 (br. s, 3H), 3.36 (br. s, 3H), 7.17 (dd, 1H), 7.23-7.28 (m, 1H), 7.34 (d, 1H), 8.77 (s, 1H).

Example 31A 1-(3-Methyl-2-oxo-2,3-dihydro-1,3-benzoxazol-6-yl)-2,4-dioxo-1,2,3,4-tetrahydropyrimidine-5-carbonitrile

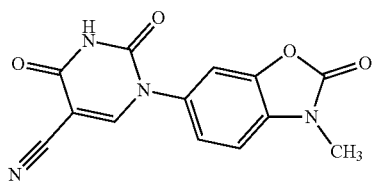 [SMILES: Cn1c(=O)oc2cc(-n3cc(C#N)c(=O)[nH]c3=O)ccc21]

A mixture of 1.00 g (4.71 mmol) of ethyl (2-cyano-3-ethoxyprop-2-enoyl)carbamate and 774 mg (4.71 mmol) of 6-amino-3-methyl-1,3-benzoxazol-2(3H)-one in 10 ml of acetonitrile and 10 ml of DMF was stirred at reflux temperature overnight. After cooling to RT, the solid was filtered off, washed with acetonitrile and dried under HV. This solid was taken up in 20 ml of DMF, 985 µl (7.07 mmol) of triethylamine were added and the solution was stirred at 80° C. for 4 h. After cooling to RT, the mixture was diluted with 200 ml of water. The solid was filtered off and washed with water. The entire filtrate was allowed to stand at 20° C. overnight, once again resulting in the precipitation of a solid. The solid was filtered off and dried under high vacuum. This gave 276 mg (19% of theory) of the title compound.

LC-MS (Method 19): $R_t$=1.21 min; m/z=285 (M+H)$^+$.
$^1$H-NMR (400 MHz, DMSO-d$_6$): δ [ppm]=3.38 (s, 3H), 7.34-7.40 (m, 2H), 7.56 (d, 1H), 8.78 (s, 1H), 12.14 (br. s, 1H).

Example 32A 1-(3-Methyl-2-oxo-2,3-dihydro-1,3-benzothiazol-6-yl)-2,4-dioxo-1,2,3,4-tetrahydropyrimidine-5-carbonitrile

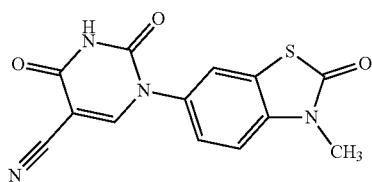

A mixture of 1.00 g (4.71 mmol) of ethyl (2-cyano-3-ethoxyprop-2-enoyl)carbamate and 849 mg (4.71 mmol) of 6-amino-3-methyl-1,3-benzothiazol-2(3H)-one (for preparation: see *J. Het. Chem.* 1992, 29 (5), 1069-1076, Example 8b) in 28 ml of acetonitrile was heated in the microwave at 180° C. for 2 h. After cooling to RT, the solvent was removed on a rotary evaporator. The residue was stirred with 10 ml of methanol for 30 min. Subsequently, the solid was filtered off, washed with a little methanol and with ether and then dried under HV. This gave 859 mg (49% of theory, purity 81%) of the title compound.

LC-MS (Method 1): $R_t$=0.62 min; ES neg: m/z=299 (M−H)$^-$.
$^1$H-NMR (400 MHz, DMSO-d$_6$): δ [ppm]=3.45 (s, 3H), 7.46 (s, 1H), 7.50 (d, 1H), 7.81 (d, 1H), 8.81 (s, 1H), 12.16 (br.s, 1H).

Example 33A 2,4-Dioxo-1-[4-(2-oxoimidazolidin-1-yl)phenyl]-1,2,3,4-tetrahydropyrimidine-5-carbonitrile

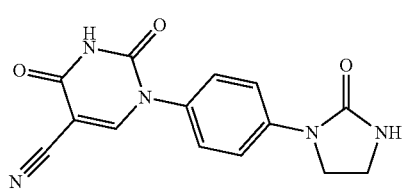 [SMILES: N#Cc1cn(-c2ccc(N3CCNC3=O)cc2)c(=O)[nH]c1=O]

A suspension of 600 mg (2.83 mmol) of ethyl (2-cyano-3-ethoxyprop-2-enoyl)carbamate and 501 mg (2.83 mmol) of 1-(4-aminophenyl)imidazolidin-2-one (for preparation see: P. Stabile et al., *Tetrahedron Letters* 2010, 51 (24), 3232-3235) in 15 ml of acetonitrile was heated in the microwave at 180° C. for 1 h. After cooling to RT, the solid was filtered off with suction, washed with acetonitrile and dried under high vacuum. The crude product thus obtained (540 mg, 55% of theory, purity about 55%) was used without any additional purification.

LC-MS (Method 1): $R_t$=0.46 min; m/z=298 (M+H)$^+$.
$^1$H-NMR (400 MHz, DMSO-d$_6$): δ [ppm]=3.40-3.48 (m, 2H), 3.84-3.93 (m, 2H), 7.10 (s, 1H), 7.39 (d, 2H), 7.66 (d, 2H), 8.76 (s, 1H), 12.09 (br. s, 1H).

Example 34A 2,4-Dioxo-1-[4-(2-oxo-1,3-oxazolidin-3-yl)phenyl]-1,2,3,4-tetrahydropyrimidine-5-carbonitrile

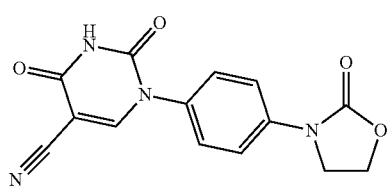 [SMILES: N#Cc1cn(-c2ccc(N3CCOC3=O)cc2)c(=O)[nH]c1=O]

A suspension of 500 mg (2.36 mmol) of ethyl (2-cyano-3-ethoxyprop-2-enoyl)carbamate and 420 mg (2.36 mmol)

of 3-(4-aminophenyl)-1,3-oxazolidin-2-one (for preparation: see WO2010/019903, p. 222, Method 38; or Farmaco Sci. Ed. (1969), 179) in 15 ml of acetonitrile was heated in the microwave at 180° C. for 1 h. After cooling to RT, about ⅔ of the solvent were removed on a rotary evaporator. The solid formed was filtered off with suction, washed with acetonitrile and ether and dried under high vacuum. The crude product thus obtained (470 mg, 51% of theory, purity about 77%) was used without any additional purification.

LC-MS (Method 1): $R_t$=0.50 min; m/z=299 (M+H)$^+$.

$^1$H-NMR (400 MHz, DMSO-d$_6$): δ [ppm]=4.07-4.15 (m, 2H), 4.44-4.52 (m, 2H), 7.49 (d, 2H), 7.68 (d, 2H), 8.78 (s, 1H), 12.12 (br. s., 1H).

Example 35A

6-Methyl-1-(3-methyl-2-oxo-2,3-dihydro-1,3-benzoxazol-6-yl)-2,4-dioxo-1,2,3,4-tetrahydropyrimidine-5-carbonitrile

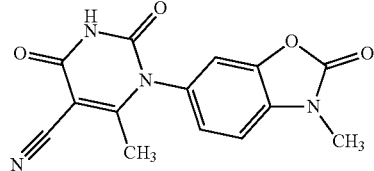 [SMILES: Cc1c(C#N)c(=O)[nH]c(=O)n1-c1ccc2c(c1)oc(=O)n2C]

145 mg (0.88 mmol) of 6-amino-3-methyl-1,3-benzoxazol-2(3H)-one were initially charged in 13 ml of ethanol, and 200 mg (0.88 mmol) ethyl (2-cyano-3-ethoxybut-2-enoyl)carbamate (for preparation see: Senda, Shigeo; Hirota, Kosaku; Notani, Jiyoji, Chemical & Pharmaceutical Bulletin (1972), 20(7), 1380-8) were added and the mixture was heated at reflux temperature for 2 h. After cooling to about 60° C., 99 mg (0.88 mmol) of potassium tert-butoxide were added and the reaction mixture was stirred further at reflux temperature for 1 h. The mixture was then cooled to about 60° C. and stirred into 50 ml of cold 0.5N aqueous hydrochloric acid. The solid was filtered off with suction, washed with water and dried under high vacuum. This gave 186 g (65% of theory) of the title compound.

LC-MS (Method 1): $R_t$=0.59 min; MS (ESIpos): m/z=299 (M+H)$^+$.

$^1$H-NMR (400 MHz, DMSO-d$_6$): δ [ppm]=2.08 (s, 3H), 3.38 (s, 3H), 7.31-7.36 (m, 1H), 7.37-7.43 (m, 1H), 7.53 (d, 1H), 12.11 (s, 1H).

Example 36A 1-(1,3-Dimethyl-2-oxo-2,3-dihydro-1H-benzimidazol-5-yl)-N'-hydroxy-2,4-dioxo-3-[(1R)-4-(trifluoromethyl)-2,3-dihydro-1H-inden-1-yl]-1,2,3,4-tetrahydropyrimidine-5-carboximidamide (R Enantiomer)

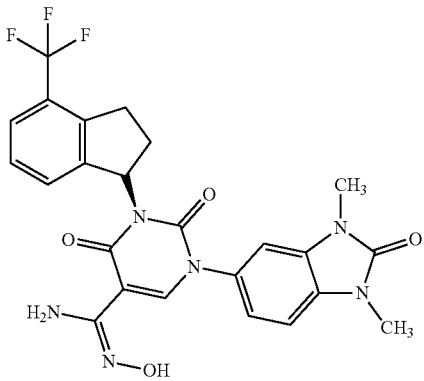

Under argon, 58 µl (415 µmol) of triethylamine were added to a solution of 29 mg (415 µmol) of hydroxylamine hydrochloride in 1.1 ml of DMSO. The mixture was stirred at RT for 10 min and then filtered. 40 mg (83 µmol) of 1-(1,3-dimethyl-2-oxo-2,3-dihydro-1H-benzimidazol-5-yl)-2,4-dioxo-3-[(1R)-4-(trifluoromethyl)-2,3-dihydro-1H-inden-1-yl]-1,2,3,4-tetrahydropyrimidine-5-carbonitrile (Example 1) were added to the filtrate, and this mixture was heated at 75° C. overnight. After cooling to RT, the reaction mixture was separated by preparative HPLC (Method 6). This gave 15 mg (35% of theory) of the title compound.

LC-MS (Method 1): $R_t$=0.90 min; MS (ESIpos): m/z=515 (M+H)$^+$.

$^1$H-NMR (400 MHz, CD$_2$Cl$_2$): δ [ppm]=2.39-2.51 (m, 1H), 2.61 (ddd, 1H), 3.10-3.22 (m, 1H), 3.35 (s, 3H), 3.37 (s, 3H), 3.42-3.54 (m, 1H), 6.56-6.67 (m, 1H), 6.98 (d, 1H), 7.11 (br. d, 1H), 7.19 (br. s., 1H), 7.28-7.39 (m, 2H), 7.52 (d, 1H), 7.57 (br. s, 2H), 8.97 (br. s, 1H).

Analogously to Example 36A, the following Examples 37A to 41A were prepared from the corresponding nitriles and 5 equivalents of hydroxylamine hydrochloride (Table 1).

TABLE 1

| Example | IUPAC name/structure (Yield) | Precursor | Analytical data |
|---|---|---|---|
| 37A | 1-(1,3-dimethyl-2-oxo-2,3-dihydro-1H-benzimidazol-5-yl)-N'-hydroxy-3-[2-methyl-3-(trifluoromethyl)benzyl]-2,4-dioxo-1,2,3,4-tetrahydropyrimidine-5-carboximidamide<br><br>yield: 285 mg (71% of theory) | Ex. 6 | LC/MS (Method 1): $R_t$ = 0.88 min; m/z = 503 (M + H)$^+$ |
| 38A | N'-hydroxy-3-[2-methyl-3-(trifluoromethyl)benzyl]-2,4-dioxo-1-[4-(2-oxoimidazolidin-1-yl)phenyl]-1,2,3,4-tetrahydropyrimidine-5-carboximidamide<br><br>yield: 298 mg (65% of theory) | Ex. 4 | LC/MS (Method 1): $R_t$ = 0.86 min; m/z = 503 (M + H)$^+$ |
| 39A | 1-(3,4-dimethoxyphenyl)-N'-hydroxy-3-[2-methyl-3-(trifluoromethyl)benzyl]-2,4-dioxo-1,2,3,4-tetrahydropyrimidine-5-carboximidamide<br><br>yield: 360 mg (74% of theory) | Ex. 9 | LC/MS (Method 1): $R_t$ = 0.89 min; m/z = 479 (M + H)$^+$ |

TABLE 1-continued

| Example | IUPAC name/structure (Yield) | Precursor | Analytical data |
|---|---|---|---|
| 40A | N'-hydroxy-1-(4-methoxyphenyl)-3-[2-methyl-3-(trifluoromethyl)benzyl]-2,4-dioxo-1,2,3,4-tetrahydropyrimidine-5-carboximidamide<br><br>yield: 92 mg (72% of theory) | Ex. 11 | LC/MS (Method 2): $R_t$ = 1.12 min; m/z = 449 (M + H)$^+$ |
| 41A | N'-hydroxy-1-(3-methyl-2-oxo-2,3-dihydro-1,3-benzoxazol-6-yl)-2,4-dioxo-3-[(1R)-4-(trifluoromethyl)-2,3-dihydro-1H-inden-1-yl]-1,2,3,4-tetrahydropyrimidine-5-carboximidamide<br><br>yield: 19 mg (42% of theory) | Ex. 2 | LC/MS (Method 1): $R_t$ = 0.93 min; m/z = 502 (M + H)$^+$<br>$^1$H-NMR (400 MHz, CD$_2$Cl$_2$): δ [ppm] = 2.37-2.50 (m, 1H), 2.55-2.69 (m, 1H), 3.09-3.22 (m, 1H), 3.38 (s, 3H), 3.41-3.53 (m, 1H), 6.53-6.68 (m, 1H), 7.03 (d, 1H), 7.17-7.44 (m, 6H), 7.51 (d, 1H), 8.82 (br. s, 1H). |

Example 42A

N'-hydroxy-3-[2-methyl-3-(trifluoromethyl)benzyl]-
2,4-dioxo-1-[4-(2-oxo-1,3-oxazolidin-3-yl)phenyl]-
1,2,3,4-tetrahydropyrimidine-5-carboximidamide

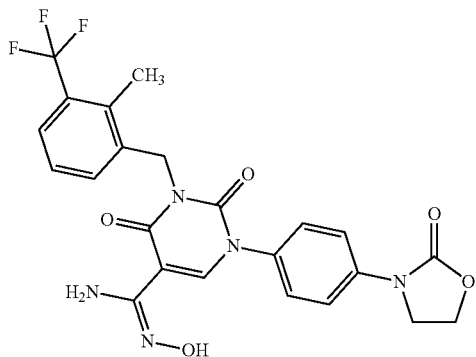 [SMILES: Cc1c(Cn2c(=O)c(/C(N)=N\O)cn(-c3ccc(N4CCOC4=O)cc3)c2=O)cccc1C(F)(F)F]

Under argon, 1.3 ml (9.35 mmol) of triethylamine were added to a solution of 650 mg (9.35 mmol) of hydroxylamine hydrochloride in 23 ml of DMSO. The mixture was stirred at RT for 10 min and then filtered. 1.00 g (1.9 mmol, purity 90%) of 3-[2-methyl-3-(trifluoromethyl)benzyl]-2,4-dioxo-1-[4-(2-oxo-1,3-oxazolidin-3-yl)phenyl]-1,2,3,4-tetrahydropyrimidine-5-carbonitrile (Example 5) was added to the filtrate, and this mixture was heated at 75° C. overnight. After cooling, the reaction mixture was poured into 100 ml of 0.1N aqueous hydrochloric acid. The precipitated solid was filtered off, washed with water and dried. This solid was stirred with 30 ml of acetonitrile, resulting in the dissolution of the product, whereas an impurity remained undissolved. The impurity was filtered off, the filtrate was concentrated and the residue was dried under HV. This gave 1.0 g (about 95% pure, quant. yield) of the title compound.

LC/MS (Method 13): $R_t$=0.87 min; m/z=504 (M+H)$^+$.

$^1$H-NMR (400 MHz, DMSO-d$_6$): δ [ppm]=2.47 (s, 3H), 4.11 (t, 2H), 4.48 (t, 2H), 5.13 (s, 2H), 7.32-7.44 (m, 2H), 7.54-7.65 (m, 3H), 7.73 (d, 2H), 8.60 (br. s, 1H).

Example 43A

Ethyl 2,4-dioxo-1-[4-(2-oxo-1,3-oxazolidin-3-yl)
phenyl]-3-[(1R)-4-(trifluoromethyl)-2,3-dihydro-1H-
inden-1-yl]-1,2,3,4-tetrahydropyrimidine-5-carboxy-
late (R Enantiomer)

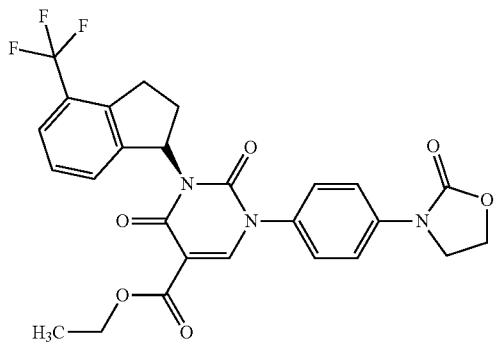

Under argon, 9.00 g (26.1 mmol) of the compound from Example 4A, 6.85 g (33.9 mmol) of (1S)-4-(trifluoromethyl)indan-1-ol and 12.31 g (46.9 mmol) of triphenylphosphine were initially charged in a mixture of 359 ml of anhydrous THF and 359 ml of anhydrous DMF and cooled to 0° C. 8.43 g (41.7 mmol) of diisopropyl azodicarboxylate were added dropwise. The reaction mixture was then allowed to warm to RT and was stirred at RT for 1 h. 100 ml of 1 N aqueous hydrochloric acid were added. The mixture was stirred for another 15 min and diluted with 1 l of ethyl acetate. The organic phase was separated off, washed three times with in each case 800 ml of 1 N aqueous hydrochloric acid, then twice with in each case 300 ml of 1 N aqueous sodium carbonate solution and once with 400 ml of saturated aqueous sodium chloride solution, dried over sodium sulfate and concentrated on a rotary evaporator. The solid that remained was stirred in a mixture of 300 ml of MTBE and 200 ml of 2-propanol, isolated by filtration, washed with 100 ml of MTBE and dried under high vacuum. This gave 8.2 g (54% of theory, purity 91%; with 6% of triphenylphosphine oxide as main impurity).

LC-MS (Method 1): $R_t$=1.11 min; MS (ESIpos): m/z=530 (M+H)$^+$.

$^1$H-NMR (400 MHz, CD$_2$Cl$_2$): δ [ppm]=1.23 (t, 3H), 2.29-2.41 (m, 1H), 2.50 (dtd, 1H), 3.00-3.12 (m, 1H), 3.33-3.45 (m, 1H), 3.93-4.02 (m, 2H), 4.20 (q, 2H), 4.35-4.45 (m, 2H), 6.53 (br. t, 1H), 7.15-7.33 (m, 4H), 7.41 (d, 1H), 7.59 (d, 2H), 8.21 (s, 1H).

Example 44A 2,4-Dioxo-1-[4-(2-oxo-1,3-oxazolidin-3-yl)phenyl]-
3-[(1R)-4-(trifluoromethyl)-2,3-dihydro-1H-inden-1-
yl]-1,2,3,4-tetrahydropyrimidine-5-carboxylic acid
(R Enantiomer)

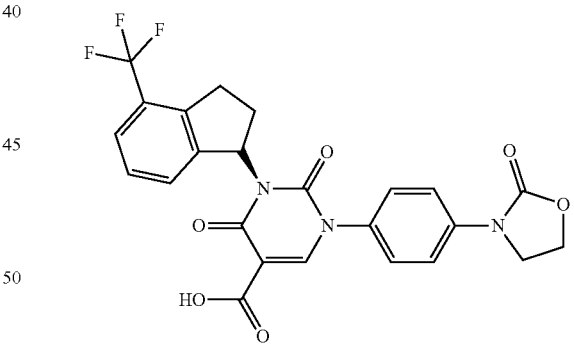

7.6 g (13.1 mmol) of the compound from Example 43A, 82.7 ml of glacial acetic acid and 41.4 ml of conc. hydrochloric acid were heated at reflux temperature for 1 h. After cooling to RT, the reaction mixture was stirred into 1500 ml of water. The solid formed was filtered off, washed with a little water and dried under high vacuum. The residue was then dissolved in a little DMSO and purified by preparative HPLC (Method 5). This gave 4.75 g (72% of theory) of the title compound.

LC-MS (Method 1): $R_t$=1.09 min; MS (ESIpos): m/z=502 (M+H)$^+$.

$^1$H-NMR (400 MHz, CD$_2$Cl$_2$): δ [ppm]=2.31-2.45 (m, 1H), 2.57 (dtd, 1H), 3.02-3.18 (m, 1H), 3.31-3.50 (m, 1H), 3.88-4.06 (m, 2H), 4.33-4.49 (m, 2H), 6.56 (br. s., 1H), 7.16-7.36 (m, 4H), 7.45 (d, 1H), 7.62 (d, 2H), 8.46 (s, 1H).

WORKING EXAMPLES

Example 1

1-(1,3-Dimethyl-2-oxo-2,3-dihydro-1H-benzimidazol-5-yl)-2,4-dioxo-3-[(1R)-4-(trifluoromethyl)-2,3-dihydro-1H-inden-1-yl]-1,2,3,4-tetrahydropyrimidine-5-carbonitrile (R Enantiomer)

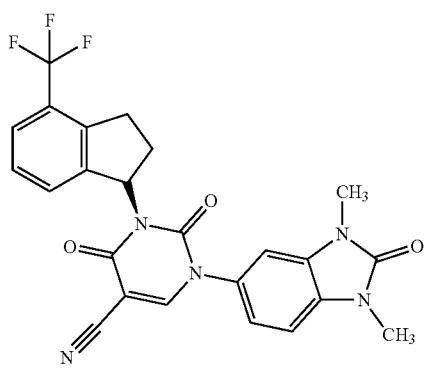

49 mg (0.17 mmol) of 1-(1,3-dimethyl-2-oxo-2,3-dihydro-1H-benzimidazol-5-yl)-2,4-dioxo-1,2,3,4-tetrahydropyrimidine-5-carbonitrile from Example 30A, 36.7 mg (0.18 mmol) of (1S)-4-(trifluoromethyl)indan-1-ol and 73.5 mg (0.28 mmol) of triphenylphosphine were initially charged in 1 ml of THF and 2 ml of DMF at RT. 53.3 mg (0.26 mmol) of diisopropyl azodicarboxylate were added and the reaction mixture was stirred at RT for 1 hour. Subsequently, 0.15 ml of 1N aqueous hydrochloric acid were added and the mixture was stirred for a further 15 min. The mixture was separated by preparative HPLC (Method 6). This gave 34 mg (43% of theory) of the title compound.

LC/MS (Method 1): $R_t$=1.06 min., m/z=482 (M+H)$^+$ $^1$H-NMR (500 MHz, CD$_2$Cl$_2$): δ [ppm]=2.24-2.41 (m, 1H), 2.49-2.59 (m, 1H), 2.98-3.15 (m, 1H), 3.30 (s, 3H), 3.32 (s, 3H), 3.36-3.47 (m, 1H), 6.39-6.59 (m, 1H), 6.82 (s, 1H), 6.88-7.03 (m, 2H), 7.18-7.33 (m, 2H), 7.44 (d, 1H), 7.90 (s, 1H).

Example 2

1-(3-Methyl-2-oxo-2,3-dihydro-1,3-benzoxazol-6-yl)-2,4-dioxo-3-[(1R)-4-(trifluoromethyl)-2,3-dihydro-1H-inden-1-yl]-1,2,3,4-tetrahydropyrimidine-5-carbonitrile (R Enantiomer)

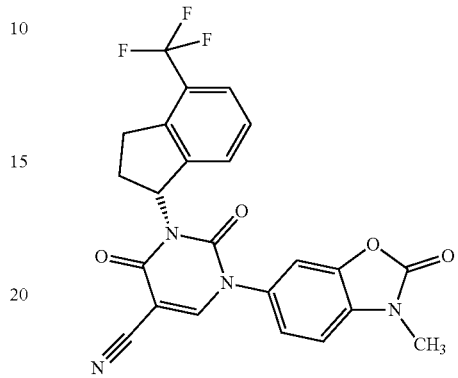

49 mg (0.17 mmol) of 1-(3-methyl-2-oxo-2,3-dihydro-1,3-benzoxazol-6-yl)-2,4-dioxo-1,2,3,4-tetrahydropyrimidine-5-carbonitrile from Example 31A, 38.3 mg (0.19 mmol) of (1S)-4-(trifluoromethyl)indan-1-ol and 76.9 mg (0.29 mmol) of triphenylphosphine were initially charged in 1 ml of THF and 2 ml of DMF at RT, 55.8 mg (0.28 mmol) of diisopropyl azodicarboxylate were added and the mixture was stirred at RT for 1 h. 0.15 ml of 1 N aqueous hydrochloric acid was added, and the mixture was stirred for 15 minutes. The mixture was separated by preparative HPLC (Method 6). This gave 38 mg (47% of theory) of the title compound.

LC/MS (Method 1): $R_t$=1.10 min; m/z=469 (M+H)$^+$ $^1$H-NMR (400 MHz, CD$_2$Cl$_2$): δ [ppm]=2.31-2.49 (m, 1H), 2.56-2.69 (m, 1H), 3.03-3.21 (m, 1H), 3.35-3.43 (s, 3H), 3.44-3.53 (m, 1H), 6.49-6.69 (m, 1H), 7.07 (s, 1H), 7.11-7.16 (m, 1H), 7.17-7.22 (m, 1H), 7.33 (s, 2H), 7.45-7.60 (m, 1H), 7.95 (s, 1H).

Example 3

1-(3-Methyl-2-oxo-2,3-dihydro-1,3-benzothiazol-6-yl)-2,4-dioxo-3-[(1R)-4-(trifluoromethyl)-2,3-dihydro-1H-inden-1-yl]-1,2,3,4-tetrahydropyrimidine-5-carbonitrile (R Enantiomer)

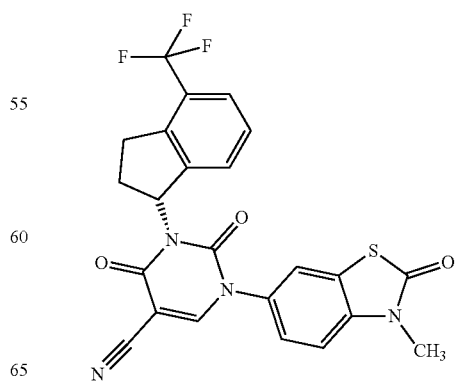

49 mg (0.16 mmol) of 1-(3-methyl-2-oxo-2,3-dihydro-1,3-benzothiazol-6-yl)-2,4-dioxo-1,2,3,4-tetrahydropyrimidine-5-carbonitrile from Example 32A, 36.3 mg (0.18 mmol) of (1S)-4-(trifluoromethyl)indan-1-ol and 72.8 mg (0.28 mmol) of triphenylphosphine were initially charged in 1 ml of THF and 2 ml of DMF at RT, 52.8 mg (0.26 mmol) of diisopropyl azodicarboxylate were added and the mixture was stirred at RT for 1 h. 0.15 ml of 1N aqueous hydrochloric acid was added. The mixture was stirred for 15 minutes and then separated by preparative HPLC (Method 6). This gave 29 mg (37% of theory) of the title compound.

LC/MS (Method 1): $R_t$=1.17 min., m/z=485 (M+H)$^+$ $^1$H-NMR (400 MHz, CD$_2$Cl$_2$): δ [ppm]=2.32-2.48 (m, 1H), 2.53-2.74 (m, 1H), 3.02-3.23 (m, 1H), 3.41-3.54 (m, 1H), 3.45 (s, 3H), 6.57 (d, 1H), 7.14 (d, 1H), 7.25 (d, 1H), 7.30-7.37 (m, 2H), 7.41 (s, 1H), 7.52 (d, 1H), 7.96 (s, 1H).

Example 4

3-[2-Methyl-3-(trifluoromethyl)benzyl]-2,4-dioxo-1-[4-(2-oxoimidazolidin-1-yl)phenyl]-1,2,3,4-tetrahydropyrimidine-5-carbonitrile

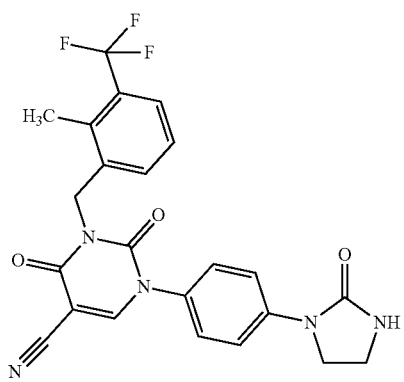 [SMILES: Cc1c(Cn2c(=O)c(C#N)cn(-c3ccc(N4CCNC4=O)cc3)c2=O)cccc1C(F)(F)F]

58 mg (0.2 mmol) of 2,4-dioxo-1-[4-(2-oxoimidazolidin-1-yl)phenyl]-1,2,3,4-tetrahydropyrimidine-5-carbonitrile from Example 33A were initially charged in 2 ml of acetonitrile at RT, 54.3 mg (0.22 mmol) of 1-(bromomethyl)-2-methyl-3-(trifluoromethyl)benzene, 53.9 mg (0.39 mmol) of potassium carbonate and 16.2 mg (0.1 mmol) of potassium iodide were added and the mixture was stirred at reflux temperature for 3 h. At RT, DMSO was added, and the reaction solution was separated by preparative HPLC (Method 6). This gave 36 mg (39% of theory) of the title compound.

LC-MS (Method 2): $R_t$=1.21 min., m/z=470 (M+H)$^+$ $^1$H-NMR (400 MHz, DMSO-d$_6$): δ [ppm]=2.46-2.55 (m, 2H), 2.88-3.02 (m, 2H), 4.14 (s, 2H), 6.19 (s, 1H), 6.35-6.55 (m, 4H), 6.62-6.82 (m, 3H), 8.02 (s, 1H).

Example 5

3-[2-Methyl-3-(trifluoromethyl)benzyl]-2,4-dioxo-1-[4-(2-oxo-1,3-oxazolidin-3-yl)phenyl]-1,2,3,4-tetrahydropyrimidine-5-carbonitrile

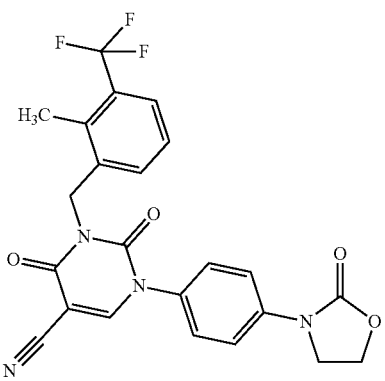 [SMILES: Cc1c(Cn2c(=O)c(C#N)cn(-c3ccc(N4CCOC4=O)cc3)c2=O)cccc1C(F)(F)F]

150 mg (0.38 mmol) of 2,4-dioxo-1-[4-(2-oxo-1,3-oxazolidin-3-yl)phenyl]-1,2,3,4-tetrahydropyrimidine-5-carbonitrile from Example 34A were initially charged in 5 ml of acetonitrile at RT, 145 mg (0.57 mmol) of 1-(bromomethyl)-2-methyl-3-(trifluoromethyl)benzene, 158.5 mg (1.15 mmol) of potassium carbonate and 31.7 mg (0.19 mmol) of potassium iodide were added and the mixture was stirred at reflux temperature for 3 h. At RT, the reaction solution was diluted with ethyl acetate and extracted with 1N aqueous hydrochloric acid. The organic phase was washed first with saturated aqueous sodium carbonate solution, then with saturated aqueous sodium chloride solution, then dried over sodium sulfate and concentrated. The residue was stirred with 4 ml of methanol, and the solid was filtered off with suction, washed with methanol and diethyl ether and dried. This gave 126 mg (69% of theory) of the title compound.

LC-MS (Method 2): $R_t$=1.26 min., m/z=471 (M+H)$^+$ $^1$H-NMR (400 MHz, DMSO-d$_6$): δ [ppm]=2.45 (s, 3H), 4.10 (t, 2H), 4.47 (t, 2H), 4.97-5.24 (m, 2H), 7.31-7.39 (m, 1H), 7.42-7.47 (m, 1H), 7.53 (d, 2H), 7.61 (d, 1H), 7.71 (d, 2H), 8.98 (s, 1H).

Example 6

1-(1,3-Dimethyl-2-oxo-2,3-dihydro-1H-benzimidazol-5-yl)-3-[2-methyl-3-(trifluoromethyl)benzyl]-2,4-dioxo-1,2,3,4-tetrahydropyrimidine-5-carbonitrile

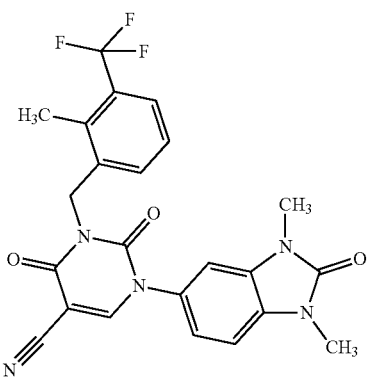 [SMILES: Cc1c(Cn2c(=O)c(C#N)cn(-c3ccc4c(c3)n(C)c(=O)n4C)c2=O)cccc1C(F)(F)F]

150 mg (0.45 mmol) of 1-(1,3-dimethyl-2-oxo-2,3-dihydro-1H-benzimidazol-5-yl)-2,4-dioxo-1,2,3,4-tetrahydropyrimidine-5-carbonitrile from Example 30A were initially charged in 5 ml of acetonitrile at RT, 171 mg (0.67 mmol) of 1-(bromomethyl)-2-methyl-3-(trifluoromethyl)benzene, 186 mg (1.35 mmol) of potassium carbonate and 37.3 mg (0.23 mmol) of potassium iodide were added and the mixture was stirred at reflux temperature for 3 h. At RT, the reaction solution was diluted with ethyl acetate and extracted with 1N aqueous hydrochloric acid. The organic phase was washed with saturated aqueous sodium carbonate solution and with saturated aqueous sodium chloride solution, dried over sodium sulfate and concentrated. The residue was stirred with 3 ml of methanol, and the solid was filtered off with suction, washed with methanol and diethyl ether and dried. This gave 160 mg (76% of theory) of the title compound.

LC/MS (Method 1): $R_t$=1.26 min., m/z=470 (M+H)$^+$ $^1$H-NMR (400 MHz, DMSO-d$_6$): δ [ppm]=2.45 (s, 3H), 3.34 (s, 3H), 3.37 (s, 3H), 5.04-5.15 (m, 2H), 7.17-7.24 (m, 1H), 7.25-7.30 (m, 1H), 7.31-7.40 (m, 2H), 7.41-7.49 (m, 1H), 7.61 (d, 1H), 8.96 (s, 1H).

Example 7

3-[4-Chloro-2,3-dihydro-1H-inden-1-yl]-1-(1,3-dimethyl-2-oxo-2,3-dihydro-1H-benzimidazol-5-yl)-2,4-dioxo-1,2,3,4-tetrahydropyrimidine-5-carbonitrile (Racemate)

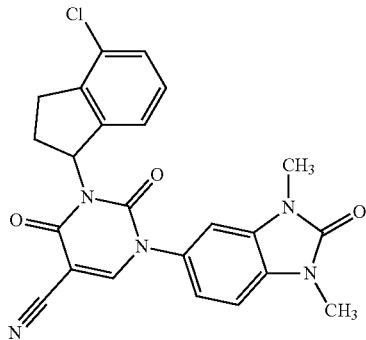 [SMILES: Cn1c(=O)n(C)c2cc(-n3cc(C#N)c(=O)n(C4CCc5c(Cl)cccc54)c3=O)ccc21]

60 mg (0.19 mmol) of 1-(1,3-dimethyl-2-oxo-2,3-dihydro-1H-benzimidazol-5-yl)-2,4-dioxo-1,2,3,4-tetrahydropyrimidine-5-carbonitrile from Example 30A, 34.8 mg (0.21 mmol) of 4-chloroindan-1-ol (racemate) and 83.7 mg (0.32 mmol) of triphenylphosphine were initially charged in 1.1 ml of THF and 2.2 ml of DMF at RT, 60.7 mg (0.30 mmol) of diisopropyl azodicarboxylate were added and the reaction mixture was stirred at RT for 1 h. Subsequently, 0.15 ml of 1N aqueous hydrochloric acid was added and the mixture was stirred for a further 15 min. The mixture was separated by preparative HPLC (Method 6). This gave 26 mg (31% of theory) of the title compound.

LC/MS (Method 1): $R_t$=1.05 min., m/z=448 (M+H)$^+$ $^1$H-NMR (400 MHz, CD$_2$Cl$_2$): δ [ppm]=2.34-2.45 (m, 1H), 2.52-2.66 (m, 1H), 2.95-3.07 (m, 1H), 3.26-3.37 (m, 1H), 3.38 (s, 3H), 3.40 (s, 3H), 6.52-6.66 (m, 1H), 6.90 (s, 1H), 6.94-7.09 (m, 3H), 7.15 (t, 1H), 7.21-7.32 (m, 1H), 7.97 (s, 1H).

Example 8

3-[4-Chloro-2,3-dihydro-1H-inden-1-yl]-1-(3-methyl-2-oxo-2,3-dihydro-1,3-benzothiazol-6-yl)-2,4-dioxo-1,2,3,4-tetrahydropyrimidine-5-carbonitrile (Racemate)

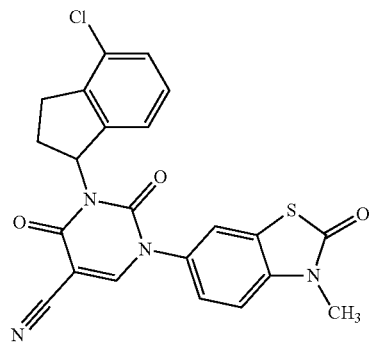 [SMILES: Cn1c(=O)sc2cc(-n3cc(C#N)c(=O)n(C4CCc5c(Cl)cccc54)c3=O)ccc21]

60 mg (0.20 mmol) of 1-(3-methyl-2-oxo-2,3-dihydro-1,3-benzothiazol-6-yl)-2,4-dioxo-1,2,3,4-tetrahydropyrimidine-5-carbonitrile from Example 32A, 37.1 mg (0.22 mmol) of 4-chloroindan-1-ol (racemate) and 89.1 mg (0.34 mmol) of triphenylphosphine were initially charged in 1.2 ml of THF and 2.3 ml of DMF at RT, 64.6 mg (0.32 mmol) of diisopropyl azodicarboxylate were added and the reaction mixture was stirred at RT for 1 h. Subsequently, 0.15 ml of 1N aqueous hydrochloric acid was added and the mixture was stirred for 15 min. The mixture was separated by preparative HPLC (Method 6). This gave 26 mg (28% of theory) of the title compound.

LC/MS (Method 3): $R_t$=2.54 min, m/z=451 (M+H)$^+$ $^1$H-NMR (400 MHz, CD$_2$Cl$_2$): δ [ppm]=2.29-2.44 (m, 1H), 2.59 (m, 1H), 2.91-3.11 (m, 1H), 3.23-3.37 (m, 1H), 3.45 (s, 3H), 6.59 (br. s, 1H), 7.04 (d, 1H), 7.11-7.19 (m, 2H), 7.20-7.30 (m, 2H), 7.41 (s, 1H), 7.95 (s, 1H).

Example 9

1-(3,4-Dimethoxyphenyl)-3-[2-methyl-3-(trifluoromethyl)benzyl]-2,4-dioxo-1,2,3,4-tetrahydropyrimidine-5-carbonitrile

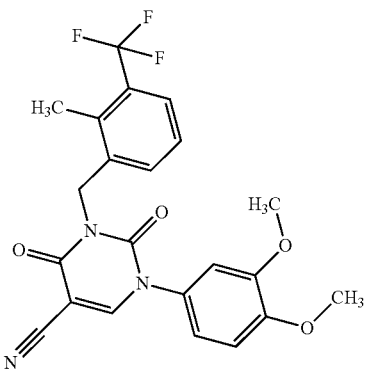 [SMILES: COc1ccc(-n2cc(C#N)c(=O)n(Cc3cccc(C(F)(F)F)c3C)c2=O)cc1OC]

150 mg (0.45 mmol) of 1-(3,4-dimethoxyphenyl)-2,4-dioxo-1,2,3,4-tetrahydropyrimidine-5-carbonitrile (preparation: see U.S. Pat. No. 4,266,056, example 13, column 11) were initially charged in 5 ml of acetonitrile at RT, 168.8 mg (0.67 mmol) of 1-(bromomethyl)-2-methyl-3-(trifluoromethyl)benzene, 184.4 mg (1.33 mmol) of potassium carbonate and 36.9 mg (0.22 mmol) of potassium iodide were added and the mixture was stirred at reflux temperature for 3 h. At RT, the reaction solution was diluted with ethyl acetate and extracted with 1N aqueous hydrochloric acid. The organic phase was washed with saturated aqueous sodium carbonate solution and with saturated aqueous sodium chloride solution, dried over sodium sulfate and concentrated. The residue was stirred with 2 ml of methanol, and the solid was filtered off with suction, washed with a little methanol and then with diethyl ether and dried. This gave 126 mg (59% of theory) of the title compound.

LC/MS (Method 1): $R_t$=1.12 min, m/z=446 (M+H)$^+$ $^1$H-NMR (400 MHz, DMSO-d$_6$): δ [ppm]=2.45 (s, 3H), 3.76 (s, 3H), 3.80 (s, 3H), 5.07 (s, 2H), 6.99-7.09 (m, 2H), 7.17 (d, 1H), 7.30-7.46 (m, 2H), 7.61 (d, 1H), 8.93 (s, 1H).

Example 10

3-(2,3-Dichlorobenzyl)-1-(4-methoxyphenyl)-2,4-dioxo-1,2,3,4-tetrahydropyrimidine-5-carbonitrile

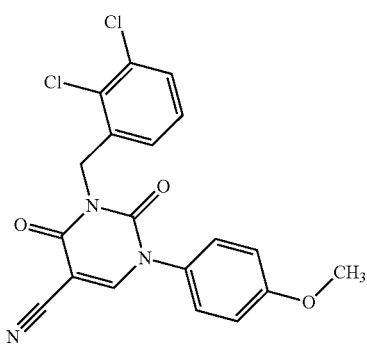 [SMILES: COc1ccc(-n2cc(C#N)c(=O)n(Cc3cccc(Cl)c3Cl)c2=O)cc1]

300 mg (1.23 mmol) of 1-(4-methoxyphenyl)-2,4-dioxo-1,2,3,4-tetrahydropyrimidine-5-carbonitrile were initially charged in 12 ml of acetonitrile at RT, 325.5 mg (1.36 mmol) of 1-(bromomethyl)-2,3-dichlorobenzene, 340.9 mg (2.47 mmol) of potassium carbonate and 102.4 mg (0.62 mmol) of potassium iodide were added and the mixture was stirred at reflux temperature for 5 h. The reaction mixture was cooled to RT, filtered and concentrated under reduced pressure. The residue was stirred with 2 ml of boiling methanol. After cooling to RT, the precipitate was filtered off with suction, washed with a little isopropanol and dried. This gave 423 mg (81% of theory) of the title compound.

LC/MS (Method 1): $R_t$=1.15 min., m/z=402 (M+H)$^+$ $^1$H-NMR (400 MHz, DMSO-d$_6$): δ [ppm]=3.80 (s, 3H), 5.08 (s, 2H), 6.97-7.13 (m, 2H), 7.23-7.35 (m., 2H), 7.38-7.48 (m, 2H), 7.54-7.64 (m, 1H), 8.87-9.09 (m, 1H).

Example 11

3-[2-Chloro-3-(trifluoromethyl)benzyl]-1-(4-methoxyphenyl)-2,4-dioxo-1,2,3,4-tetrahydropyrimidine-5-carbonitrile

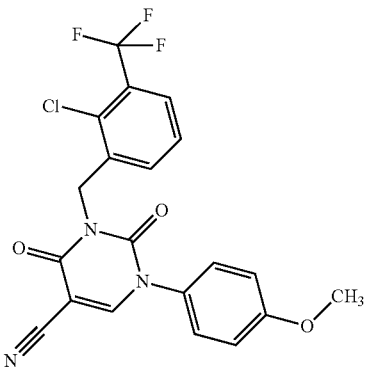 [SMILES: COc1ccc(-n2cc(C#N)c(=O)n(Cc3cccc(C(F)(F)F)c3Cl)c2=O)cc1]

300 mg (1.23 mmol) of 1-(4-methoxyphenyl)-2,4-dioxo-1,2,3,4-tetrahydropyrimidine-5-carbonitrile were initially charged in 12 ml of acetonitrile at RT, 371.1 mg (1.36 mmol) of 1-(bromomethyl)-2-chloro-3-(trifluoromethyl)benzene, 340.9 mg (2.47 mmol) of potassium carbonate and 102.4 mg (0.62 mmol) of potassium iodide were added and the mixture was stirred at reflux temperature for 5 h. Water was added, and the reaction solution was extracted with ethyl acetate. The organic phase was dried over sodium sulfate and concentrated. The residue was stirred with 2 ml of isopropanol, and the solid was filtered off with suction, washed with a little isopropanol and dried. This gave 295.4 mg (54% of theory) of the title compound.

LC/MS (Method 1): $R_t$=1.16 min; m/z=436 (M+H)$^+$ $^1$H-NMR (400 MHz, DMSO-d$_6$): δ [ppm]=3.75-3.88 (m, 3H), 5.06-5.24 (m, 2H), 7.00-7.15 (m, 2H), 7.39-7.45 (m, 2H), 7.47-7.56 (m, 1H), 7.65 (d, 1H), 7.81 (d, 1H), 8.74-9.13 (m, 1H).

Example 12

6-Methyl-1-(3-methyl-2-oxo-2,3-dihydro-1,3-benzoxazol-6-yl)-2,4-dioxo-3-[(1R)-4-(trifluoromethyl)-2,3-dihydro-1H-inden-1-yl]-1,2,3,4-tetrahydropyrimidine-5-carbonitrile (R Enantiomer)

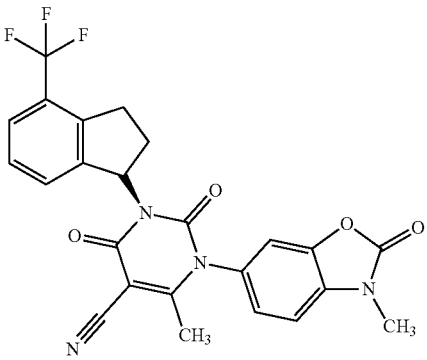

186 mg (0.62 mmol) of 6-methyl-1-(3-methyl-2-oxo-2,3-dihydro-1,3-benzoxazol-6-yl)-2,4-dioxo-1,2,3,4-tetrahydropyrimidine-5-carbonitrile from Example 35A, 151.3 mg (0.75 mmol) of (1S)-4-(trifluoromethyl)indan-1-ol and 278.1 mg (1.06 mmol) of triphenylphosphine were initially charged in 3.3 ml of THF and 6.6 ml of DMF at RT, 201.8 mg (1.0 mmol) of diisopropyl azodicarboxylate were added and the reaction mixture was stirred at RT overnight. 5 ml of 1 N aqueous hydrochloric acid were then added, and the mixture was stirred at RT for 15 min and diluted with ethyl acetate, and the phases were separated. The organic phase was washed successively with water, 0.5 M aqueous sodium carbonate solution and saturated aqueous sodium chloride solution, dried over sodium sulfate and concentrated. The crude product was purified by preparative HPLC (Method 6). This gave 50 mg (15% of theory) of the title compound.

LC/MS (Method 1): $R_t$=1.10 min., m/z=483 (M+H)$^+$ $^1$H-NMR (400 MHz, CD$_2$Cl$_2$): δ [ppm]=2.21 (s, 3H), 2.31-2.44 (m, 1H), 2.52-2.66 (m, 1H), 3.05-3.18 (m, 1H), 3.37-3.50 (m, 1H), 3.41 (s, 3H), 6.54 (br. s., 1H), 6.94-7.16 (m, 3H), 7.26-7.37 (m, 2H), 7.46-7.58 (m, 1H).

Example 13

1-(1,3-Dimethyl-2-oxo-2,3-dihydro-1H-benzimidazol-5-yl)-5-(1H-tetrazol-5-yl)-3-[(1R)-4-(trifluoromethyl)-2,3-dihydro-1H-inden-1-yl]pyrimidine-2,4(1H,3H)-dione (R Enantiomer)

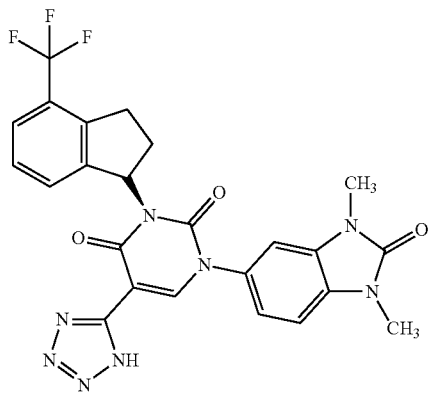

15 mg (0.03 mmol) of 1-(1,3-dimethyl-2-oxo-2,3-dihydro-1H-benzimidazol-5-yl)-2,4-dioxo-3-[(1R)-4-(trifluoromethyl)-2,3-dihydro-1H-inden-1-yl]-1,2,3,4-tetrahydropyrimidine-5-carbonitrile (R enantiomer) (Example 1) were initially charged in 2 ml of toluene at RT. 0.78 mg (0.003 mmol) of di-n-butyltin oxide and 28.7 mg (0.25 mmol) of trimethylsilyl azide were added, and the mixture was stirred at reflux temperature for 5 h. After cooling to RT, 2 ml of ethanol were added and the mixture was stirred at RT for 1 h and concentrated. The residue was dissolved in a little DMSO/acetonitrile 1:1 (v/v) and purified by preparative HPLC (Method 6). This gave 10 mg (61% of theory) of the title compound.

LC/MS (Method 1): $R_t$=1.0 min., m/z=525 (M+H)$^+$ $^1$H-NMR (400 MHz, CD$_2$Cl$_2$): δ [ppm]=2.45-2.58 (m, 1H), 2.60-2.74 (m, 2H), 3.09-3.29 (m, 1H), 3.40 (s, 3H), 3.43 (s, 3H), 3.46-3.58 (m, 1H), 6.61-6.76 (m, 1H), 7.00 (br. s., 1H), 7.07 (br. s, 2H), 7.26-7.42 (m, 3H), 7.53 (d, 1H), 8.77 (s, 1H).

Example 14

1-(3-Methyl-2-oxo-2,3-dihydro-1,3-benzoxazol-6-yl)-5-(1H-tetrazol-5-yl)-3-[(1R)-4-(trifluoromethyl)-2,3-dihydro-1H-inden-1-yl]pyrimidine-2,4(1H,3H)-dione (R Enantiomer)

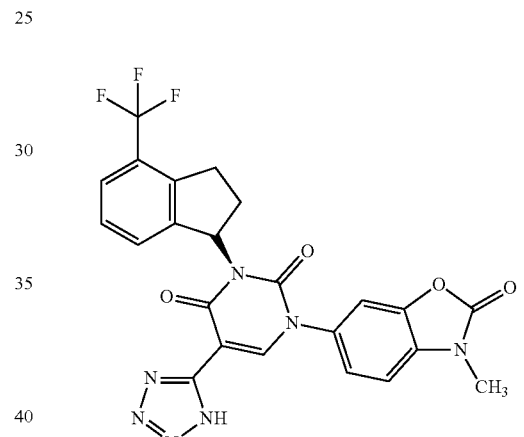

18 mg (0.04 mmol) of 1-(3-methyl-2-oxo-2,3-dihydro-1,3-benzoxazol-6-yl)-2,4-dioxo-3-[(1R)-4-(trifluoromethyl)-2,3-dihydro-1H-inden-1-yl]-1,2,3,4-tetrahydropyrimidine-5-carbonitrile (R enantiomer) (Example 2) were initially charged in 2 ml of toluene at RT. 1 mg (0.004 mmol) of di-n-butyltin oxide and 35.4 mg (0.31 mmol) of trimethylsilyl azide were added, and the mixture was stirred at reflux temperature for 5 h. After cooling to RT, 2 ml of ethanol were added and the mixture was stirred at RT for 1 h and concentrated. The residue was dissolved in a little DMSO/acetonitrile 1:1 (v/v) and purified by preparative HPLC (Method 6). This gave 11 mg (56% of theory) of the title compound.

LC/MS (Method 1): $R_t$=1.04 min., m/z=512 (M+H)$^+$ $^1$H-NMR (400 MHz, CD$_2$Cl$_2$): δ [ppm]=2.42-2.55 (m, 1H), 2.65 (d, 1H), 3.11-3.25 (m, 1H), 3.43 (s, 3H), 3.45-3.60 (m, 1H), 6.59-6.81 (m, 1H), 7.10 (d, 1H), 7.19-7.41 (m, 4H), 7.53 (d, 1H), 8.74 (s, 1H), 13.17-13.67 (m, 1H).

Example 15

1-(3-Methyl-2-oxo-2,3-dihydro-1,3-benzothiazol-6-yl)-5-(1H-tetrazol-5-yl)-3-[(1R)-4-(trifluoromethyl)-2,3-dihydro-1H-inden-1-yl]pyrimidine-2,4(1H,3H)-dione (R Enantiomer)

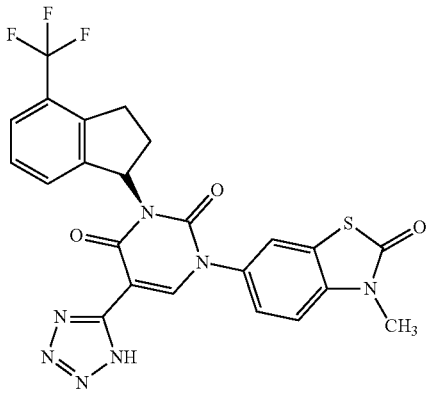

14 mg (0.03 mmol) of 1-(3-methyl-2-oxo-2,3-dihydro-1,3-benzothiazol-6-yl)-2,4-dioxo-3-[(1R)-4-(trifluoromethyl)-2,3-dihydro-1H-inden-1-yl]-1,2,3,4-tetrahydropyrimidine-5-carbonitrile (R enantiomer) (Example 3) were initially charged in 1.5 ml of toluene at RT. 0.72 mg (0.003 mmol) of di-n-butyltin oxide and 26.6 mg (0.23 mmol) of trimethylsilyl azide were added, and the mixture was stirred at reflux temperature for 5 h. After cooling to RT, 1.5 ml of ethanol were added and the mixture was stirred at RT for 1 h and concentrated. The residue was dissolved in a little DMSO/acetonitrile 1:1 (v/v) and purified by preparative HPLC (Method 6). This gave 10 mg (62% of theory) of the title compound.

LC/MS (Method 1): $R_t$=1.08 min., m/z=528 (M+H)$^+$ $^1$H-NMR (400 MHz, CD$_2$Cl$_2$): δ [ppm]=2.42-2.57 (m, 1H), 2.59-2.77 (m, 1H), 3.10-3.28 (m, 1H), 3.47 (s, 3H), 6.69 (br. s, 1H), 7.17 (d, 1H), 7.27-7.41 (m, 3H), 7.45-7.61 (m, 2H), 8.74 (s, 1H), 13.42 (br. s, 1H).

Example 16

3-(4-Chloro-2,3-dihydro-1H-inden-1-yl)-1-(1,3-dimethyl-2-oxo-2,3-dihydro-1H-benzimidazol-5-yl)-5-(1H-tetrazol-5-yl)pyrimidine-2,4(1H,3H)-dione (Racemate)

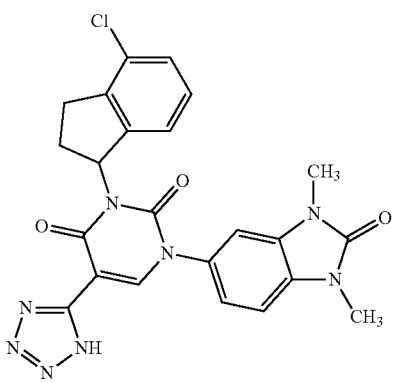 [SMILES: Cn1c(=O)n(C)c2cc(-n3cc(-c4nnn[nH]4)c(=O)n(C4CCc5c(Cl)cccc54)c3=O)ccc21]

26 mg (0.06 mmol) of 3-[4-chloro-2,3-dihydro-1H-inden-1-yl]-1-(1,3-dimethyl-2-oxo-2,3-dihydro-1H-benzimidazol-5-yl)-2,4-dioxo-1,2,3,4-tetrahydropyrimidine-5-carbonitrile from Example 7 were initially charged in 3 ml of toluene at RT. 1.45 mg (0.006 mmol) of di-n-butyltin oxide and 53.5 mg (0.46 mmol) of trimethylsilyl azide were added, and the mixture was stirred at reflux temperature for 5 h. After cooling to RT, 3 ml of ethanol were added and the mixture was stirred at RT for 1 h and concentrated. The residue was dissolved in a little DMSO/acetonitrile 1:1 (v/v) and purified by preparative HPLC (Method 6). This gave 20 mg (70% of theory) of the title compound.

LC/MS (Method 1): $R_t$=0.96 min; m/z=491 (M+H)$^+$ $^1$H-NMR (400 MHz, CD$_2$Cl$_2$): δ [ppm]=2.37-2.56 (m, 1H), 2.64 (m, 1H), 2.95-3.15 (m, 1H), 3.32-3.37 (m, 1H), 3.40 (s, 3H), 3.43 (s, 3H), 6.64-6.80 (m, 1H), 6.95-7.19 (m, 5H), 7.25 (d, 1H), 8.76 (s, 1H), 13.19-13.66 (m, 1H).

Example 17

3-(4-Chloro-2,3-dihydro-1H-inden-1-yl)-1-(1,3-dimethyl-2-oxo-2,3-dihydro-1H-benzimidazol-5-yl)-5-(1H-tetrazol-5-yl)pyrimidine-2,4(1H,3H)-dione (Enantiomer 1)

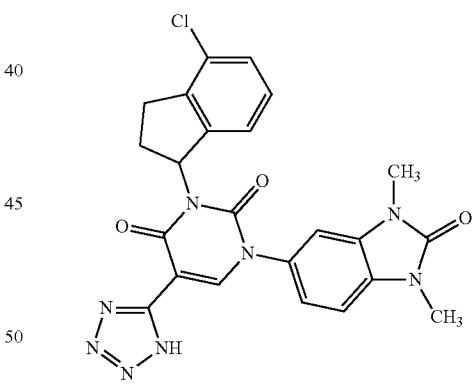

Enantiomer eluting first from the chromatographic separation of 13 mg of the compound from Example 16 on a chiral phase (Method 14). 2.6 mg of enantiomer 1 were obtained.

Chiral analytical HPLC (Method 15) $R_t$=5.84 min. 100% ee

LC/MS (Method 1): $R_t$=0.96 min., m/z=491 (M+H)$^+$

Example 18

3-(4-Chloro-2,3-dihydro-1H-inden-1-yl)-1-(1,3-dimethyl-2-oxo-2,3-dihydro-1H-benzimidazol-5-yl)-5-(1H-tetrazol-5-yl)pyrimidine-2,4(1H,3H)-dione (Enantiomer 2)

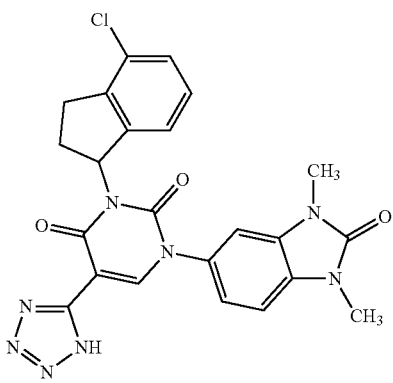

Enantiomer eluting last from the chromatographic separation of 13 mg of the compound from Example 16 on a chiral phase (Method 14). 1.9 mg of enantiomer 2 were obtained.

Chiral analytical HPLC (Method 15) $R_t$=6.42 min. 100% ee

LC/MS (Method 1): $R_t$=0.96 min; m/z=491 (M+H)$^+$.

Example 19

1-(1,3-Dimethyl-2-oxo-2,3-dihydro-1H-benzimidazol-5-yl)-3-[2-methyl-3-(trifluoromethyl)benzyl]-5-(1H-tetrazol-5-yl)pyrimidine-2,4(1H,3H)-dione

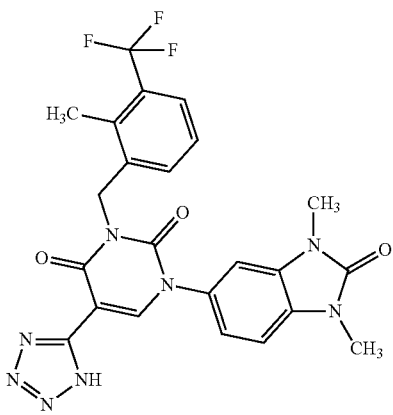 [SMILES: Cc1c(Cn2c(=O)c(-c3nnn[nH]3)cn(-c3ccc4c(c3)n(C)c(=O)n4C)c2=O)cccc1C(F)(F)F]

50 mg (0.11 mmol) of 1-(1,3-dimethyl-2-oxo-2,3-dihydro-1H-benzimidazol-5-yl)-3-[2-methyl-3-(trifluoromethyl)benzyl]-2,4-dioxo-1,2,3,4-tetrahydropyrimidine-5-carbonitrile (Example 6) were initially charged in 1.5 ml of toluene at RT. 2.65 mg (0.011 mmol) of di-n-butyltin oxide and 36.8 mg (0.32 mmol) of trimethylsilyl azide were added and the mixture was stirred at reflux temperature for 4 h. 73.6 mg (0.64 mmol) of trimethylsilyl azide were added in two portions, and the mixture stirred at reflux temperature for a total of 24 h. After cooling to RT, 0.9 ml of ethanol were added and the mixture was stirred at RT for 1 h and concentrated. The residue was dissolved in a little DMSO/acetonitrile 1:1 (v/v) and purified by preparative HPLC (Method 6). This gave 26 mg (48% of theory) of the title compound.

LC/MS (Method 1): $R_t$=0.96 min; m/z=513 (M+H)$^+$ $^1$H-NMR (400 MHz, DMSO-d$_6$): δ [ppm]=3.35 (s, 3H), 3.38 (s, 3H), 4.95-5.45 (m, 2H), 7.30 (d, 2H), 7.33-7.40 (m, 1H), 7.42-7.52 (m, 2H), 7.61 (d, 1H), 8.64 (s, 1H), 15.97-16.58 (m, 1H).

Example 20

1-(3,4-Dimethoxyphenyl)-3-[2-methyl-3-(trifluoromethyl)benzyl]-5-(1H-tetrazol-5-yl)pyrimidine-2,4(1H,3H)-dione

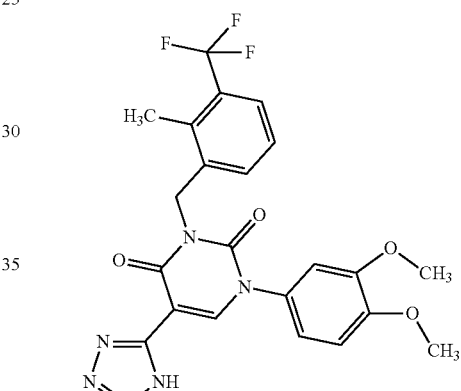

47.2 mg (0.11 mmol) of 1-(3,4-dimethoxyphenyl)-3-[2-methyl-3-(trifluoromethyl)benzyl]-2,4-dioxo-1,2,3,4-tetrahydropyrimidine-5-carbonitrile (Example 9) were initially charged in 1.5 ml of toluene at RT. 2.64 mg (0.011 mmol) of di-n-butyltin oxide and 36.6 mg (0.32 mmol) of trimethylsilyl azide were added, and the mixture was stirred at reflux temperature for 4 h. Additionally, 73.2 mg (0.64 mmol) of trimethylsilyl azide were added in two portions, and the mixture was stirred at reflux temperature for a total of 24 h. After cooling to RT, 0.9 ml of ethanol were added and the mixture was stirred at RT for 1 h and concentrated. The residue was dissolved in a little DMSO/acetonitrile 1:1 (v/v) and purified by preparative HPLC (Method 6). This gave 41 mg (78% of theory) of the title compound.

LC/MS (Method 1): $R_t$=1.0 min., m/z=489 (M+H)$^+$ $^1$H-NMR (400 MHz, DMSO-d$_6$): δ [ppm]=3.78 (s, 3H), 3.82 (s, 3H), 5.20 (s, 2H), 7.07-7.16 (m, 2H), 7.24 (d, 1H), 7.32-7.39 (m, 1H), 7.47 (d, 1H), 7.61 (d, 1H), 8.59 (s, 1H), 16.12-16.49 (m, 1H).

Example 21

3-[2-Methyl-3-(trifluoromethyl)benzyl]-1-[4-(2-ox-oimidazolidin-1-yl)phenyl]-5-(1H-tetrazol-5-yl)pyrimidine-2,4(1H,3H)-dione

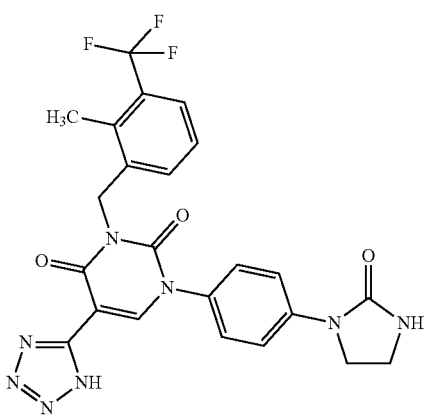 [SMILES: Cc1c(Cn2c(=O)c(-c3nnn[nH]3)cn(-c3ccc(N4CCNC4=O)cc3)c2=O)cccc1C(F)(F)F]

32 mg (0.07 mmol) of 3-[2-methyl-3-(trifluoromethyl)benzyl]-2,4-dioxo-1-[4-(2-oxoimidazolidin-1-yl)phenyl]-1,2,3,4-tetrahydropyrimidine-5-carbonitrile (Example 4) were initially charged in 1 ml of toluene at RT. 1.7 mg (0.007 mmol) of di-n-butyltin oxide and 23.6 mg (0.21 mmol) of trimethylsilyl azide were added, and the mixture was stirred at reflux temperature overnight. 47.2 mg (0.42 mmol) of trimethylsilyl azide were added in two portions, and the mixture was stirred at reflux temperature for a total of 48 hours. After cooling to RT, 0.6 ml of ethanol were added and the mixture was stirred at RT for 1 h and concentrated. The residue was dissolved in a little DMSO/acetonitrile 1:1 (v/v) and purified by preparative HPLC (Method 6). This gave 23 mg (65% of theory) of the title compound.

LC/MS (Method 2): $R_t$=1.11 min; m/z=513 (M+H)$^+$ $^1$H-NMR (400 MHz, DMSO-d$_6$): δ [ppm]=3.44 (t, 2H), 3.81-4.02 (m, 2H), 5.20 (s, 2H), 7.11 (s, 1H), 7.31-7.40 (m, 1H), 7.45-7.55 (m, 3H), 7.61 (d, 1H), 7.67-7.76 (m, 2H), 8.37-8.80 (m, 1H), 16.04-16.39 (m, 1H).

Example 22

3-(4-Chloro-2,3-dihydro-1H-inden-1-yl)-1-(3-methyl-2-oxo-2,3-dihydro-1,3-benzothiazol-6-yl)-5-(1H-tetrazol-5-yl)pyrimidine-2,4(1H,3H)-dione (Racemate)

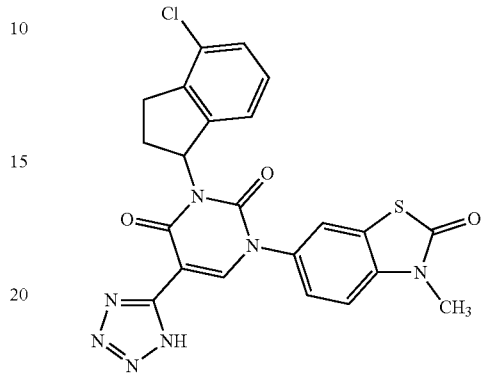

26 mg (0.06 mmol) of 3-[4-chloro-2,3-dihydro-1H-inden-1-yl]-1-(3-methyl-2-oxo-2,3-dihydro-1,3-benzothiazol-6-yl)-2,4-dioxo-1,2,3,4-tetrahydropyrimidine-5-carbonitrile (racemate) (Example 8) were initially charged in 3 ml of toluene at RT. 1.39 mg (0.006 mmol) of di-n-butyltin oxide and 51.6 mg (0.45 mmol) of trimethylsilyl azide were added, and the mixture was stirred at reflux temperature for 5 h. After cooling to RT, 3 ml of ethanol were added and the mixture was stirred at RT for 1 h and concentrated. The residue was dissolved in a little DMSO/acetonitrile 1:1 (v/v) and purified by preparative HPLC (Method 6). This gave 22 mg (80% of theory) of the title compound.

LC/MS (Method 1): $R_t$=1.04 min., m/z=494 (M+H)$^+$ $^1$H-NMR (400 MHz, CD$_2$Cl$_2$): δ [ppm]=2.39-2.53 (m, 1H), 2.57-2.72 (m, 1H), 2.98-3.11 (m, 1H), 3.24-3.41 (m, 1H), 3.47 (s, 3H), 6.71 (br. s., 1H), 7.03-7.10 (m, 1H), 7.11-7.20 (m, 2H), 7.25 (d, 1H), 7.36 (d, 1H), 7.51 (br. s., 1H), 8.69-8.80 (m, 1H), 13.27-13.63 (m, 1H).

Example 23

3-(4-Chloro-2,3-dihydro-1H-inden-1-yl)-1-(3-methyl-2-oxo-2,3-dihydro-1,3-benzothiazol-6-yl)-5-(1H-tetrazol-5-yl)pyrimidine-2,4(1H,3H)-dione (Enantiomer 1)

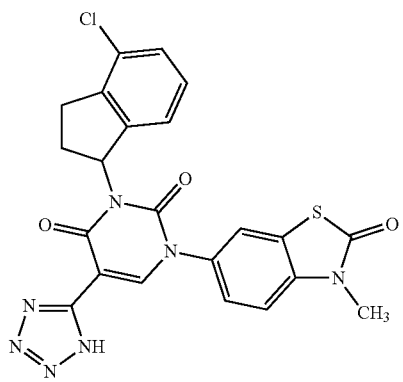 [SMILES: Cn1c(=O)sc2cc(-n3cc(-c4nnn[nH]4)c(=O)n(C4CCc5c(Cl)cccc54)c3=O)ccc21]

Enantiomer eluting first from the chromatographic separation of 17 mg of the compound from Example 22 on a chiral phase (Method 16). 7.2 mg of enantiomer 1 were obtained.

Chiral analytical HPLC (Method 17) $R_t$=9.25 min; 100% ee

LC/MS (Method 1): $R_t$=1.05 min; m/z=494 (M+H)$^+$.

Example 24

3-(4-Chloro-2,3-dihydro-1H-inden-1-yl)-1-(3-methyl-2-oxo-2,3-dihydro-1,3-benzothiazol-6-yl)-5-(1H-tetrazol-5-yl)pyrimidine-2,4(1H,3H)-dione (Enantiomer 2)

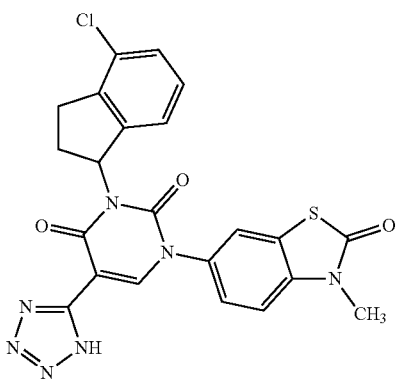 [SMILES: Cn1c(=O)sc2cc(-n3cc(-c4nnn[nH]4)c(=O)n(C4CCc5c(Cl)cccc54)c3=O)ccc21]

Enantiomer eluting last from the chromatographic separation of 17 mg of the compound from Example 22 on a chiral phase (Method 16). 8.7 mg of enantiomer 2 were obtained.

Chiral analytical HPLC (Method 17) $R_t$=10.38 min; 94% ee

LC/MS (Method 1): $R_t$=1.05 min; m/z=494 (M+H)$^+$.

Example 25

3-[2-Methyl-3-(trifluoromethyl)benzyl]-1-[4-(2-oxo-1,3-oxazolidin-3-yl)phenyl]-5-(1H-tetrazol-5-yl)pyrimidine-2,4(1H,3H)-dione

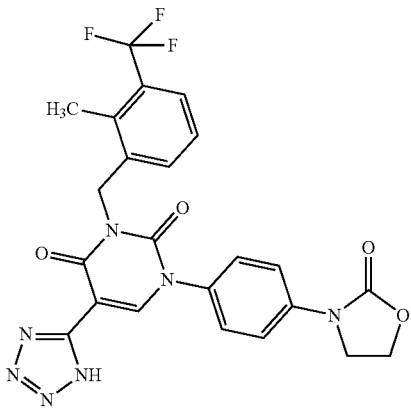 [SMILES: Cc1c(Cn2c(=O)c(-c3nnn[nH]3)cn(-c3ccc(N4CCOC4=O)cc3)c2=O)cccc1C(F)(F)F]

50 mg (0.11 mmol) of 3-[2-methyl-3-(trifluoromethyl)benzyl]-2,4-dioxo-1-[4-(2-oxo-1,3-oxazolidin-3-yl)phenyl]-1,2,3,4-tetrahydropyrimidine-5-carbonitrile (Example 5) were initially charged in 1.5 ml of toluene at RT. 2.65 mg (0.011 mmol) of di-n-butyltin oxide and 36.7 mg (0.32 mmol) of trimethylsilyl azide were added and the mixture was stirred at reflux temperature overnight. 73.4 mg (0.64 mmol) of trimethylsilyl azide were added in two portions, and the mixture was stirred at reflux temperature for a total of 30 h. After cooling to RT, 0.9 ml of ethanol were added and the mixture was stirred at RT for 1 h and concentrated. The residue was dissolved in a little DMSO/acetonitrile 1:1 (v/v) and purified by preparative HPLC (Method 6). This gave 31 mg (57% of theory) of the title compound.

LC/MS (Method 1): $R_t$=0.99 min; m/z=514 (M+H)$^+$ $^1$H-NMR (400 MHz, DMSO-d$_6$): δ [ppm]=4.12 (t, 2H), 4.40-4.61 (m, 2H), 5.20 (s, 2H), 7.31-7.39 (m, 1H), 7.49 (d, 1H), 7.58-7.65 (m, 3H), 7.73 (d, 2H), 8.64 (s, 1H), 16.04-16.53 (m, 1H).

Example 26

3-[2-Chloro-3-(trifluoromethyl)benzyl]-1-(4-methoxyphenyl)-5-(1H-tetrazol-5-yl)pyrimidine-2,4(1H,3H)-dione

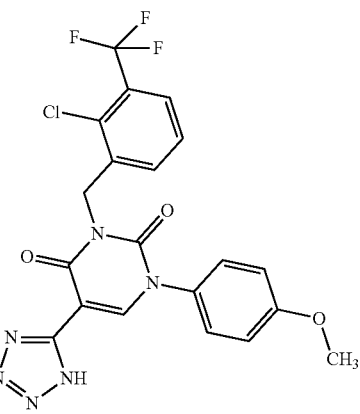

100 mg (0.23 mmol) of 3-[2-chloro-3-(trifluoromethyl)benzyl]-1-(4-methoxyphenyl)-2,4-dioxo-1,2,3,4-tetrahydropyrimidine-5-carbonitrile (Example 11) were initially charged in 2 ml of toluene at RT. 5.7 mg (0.023 mmol) of di-n-butyltin oxide and 79.31 mg (0.69 mmol) of trimethylsilyl azide were added, and the mixture was stirred at reflux temperature overnight. After cooling to RT, 2 ml of ethanol were added at RT and the mixture was stirred for 1 h and concentrated. The residue was dissolved in a little DMSO/acetonitrile 1:1 (v/v) and purified by preparative HPLC (Method 6). This gave 69 mg (59% of theory) of the title compound.

LC/MS (Method 1): $R_t$=1.08 min; m/z=479 (M+H)$^+$ $^1$H-NMR (400 MHz, DMSO-d$_6$): δ [ppm]=3.32 (s, 3H), 5.26 (s, 2H), 6.93-7.16 (m, 2H), 7.41-7.58 (m, 3H), 7.69 (d, 1H), 7.81 (d, 1H), 8.62 (s, 1H), 16.12-16.54 (m, 1H).

Example 27

3-(2,3-Dichlorobenzyl)-1-(4-methoxyphenyl)-5-(1H-tetrazol-5-yl)pyrimidine-2,4(1H,3H)-dione

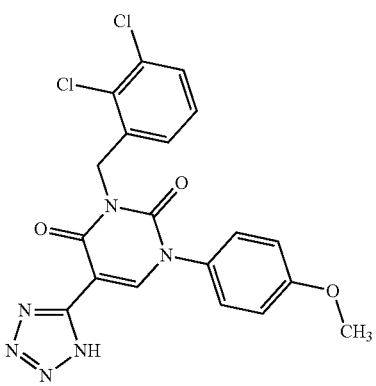 [SMILES: COc1ccc(-n2cc(-c3nnn[nH]3)c(=O)n(Cc3cccc(Cl)c3Cl)c2=O)cc1]

100 mg (0.25 mmol) of 3-(2,3-dichlorobenzyl)-1-(4-methoxyphenyl)-2,4-dioxo-1,2,3,4-tetrahydropyrimidine-5-carbonitrile (Example 10) were initially charged in 2 ml of toluene at RT. 6.19 mg (0.025 mmol) of di-n-butyltin oxide and 85.93 mg (0.75 mmol) of trimethylsilyl azide were added, and the mixture was stirred at reflux temperature overnight. After cooling to RT, 2 ml of ethanol were added and the mixture was stirred for 1 h and concentrated. The residue was dissolved in a little DMSO/acetonitrile 1:1 (v/v) and purified by preparative HPLC (Method 6). This gave 75 mg (68% of theory) of the title compound.

LC/MS (Method 1): $R_t$=1.02 min; m/z=445 (M+H)$^+$ $^1$H-NMR (400 MHz, DMSO-d$_6$): δ [ppm]=3.32 (br. s, 3H), 5.22 (s, 2H), 6.96-7.19 (m, 2H), 7.29-7.37 (m, 2H), 7.48-7.54 (m, 2H), 7.56-7.63 (m, 1H), 8.60 (s, 1H), 16.21-16.43 (m, 1H).

Example 28

3-(5-Chloro-1,2,3,4-tetrahydronaphthalen-1-yl)-1-(3-methyl-2-oxo-2,3-dihydro-1,3-benzoxazol-6-yl)-2,4-dioxo-1,2,3,4-tetrahydropyrimidine-5-carbonitrile (Racemate)

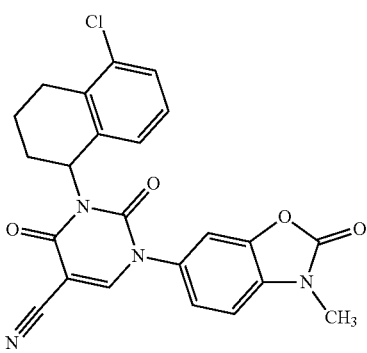 [SMILES: Cn1c(=O)oc2cc(-n3cc(C#N)c(=O)n(C4CCCc5c(Cl)cccc54)c3=O)ccc21]

The title compound was prepared analogously to Example 2 from 230.0 mg (0.81 mmol) of 1-(3-methyl-2-oxo-2,3-dihydro-1,3-benzoxazol-6-yl)-2,4-dioxo-1,2,3,4-tetrahydropyrimidine-5-carbonitrile from Example 31A and 162.6 (0.89 mmol) of 5-chloro-1,2,3,4-tetrahydronaphthalen-1-ol. This gave 180 mg (32% of theory, purity about 64%) of the title compound which was used without additional purification for the preparation of Example 29.

MS (DCI-NH$_3$, Method 12): m/z=466 [M+NH$_3$+H]$^+$ $^1$H-NMR (400 MHz, CD$_2$Cl$_2$): δ [ppm]=1.71-1.88 (m, 1H), 2.04-2.20 (m, 2H), 2.29-2.45 (m, 1H), 2.62-2.78 (m, 1H), 3.02 (d, 1H), 3.40 (s, 3H), 6.20 (br. s, 1H), 6.90 (d, 2H), 7.07 (m, 1H), 7.24 (d, 2H, 7.98 (s, 1H).

Example 29

3-(5-Chloro-1,2,3,4-tetrahydronaphthalen-1-yl)-1-(3-methyl-2-oxo-2,3-dihydro-1,3-benzoxazol-6-yl)-5-(1H-tetrazol-5-yl)pyrimidine-2,4(1H,3H)-dione (Racemate)

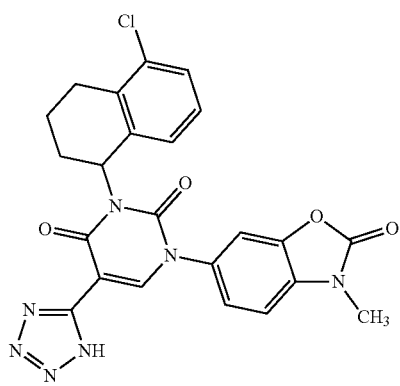 [SMILES: Cn1c(=O)oc2cc(-n3cc(-c4nnn[nH]4)c(=O)n(C4CCCc5c(Cl)cccc54)c3=O)ccc21]

90 mg (0.13 mmol) of 3-(5-chloro-1,2,3,4-tetrahydronaphthalen-1-yl)-1-(3-methyl-2-oxo-2,3-dihydro-1,3-benzoxazol-6-yl)-2,4-dioxo-1,2,3,4-tetrahydropyrimidine-5-carbonitrile (Example 28) were initially charged in 6.7 ml of toluene at RT. 3.19 mg (0.013 mmol) of di-n-butyltin oxide and 118.27 mg (1.03 mmol) of trimethylsilyl azide were added, and the mixture was stirred at reflux temperature for 5 h. After cooling to RT, 6.7 ml of ethanol were added and the mixture was stirred for 1 h and concentrated. The residue was dissolved in a little DMSO/acetonitrile 1:1 (v/v) and purified by preparative HPLC (Method 6). This gave 42 mg (67% of theory) of the title compound.

LC/MS (Method 1): $R_t$=1.03 min; m/z=492 (M+H)$^+$ $^1$H-NMR (400 MHz, CD$_2$Cl$_2$): δ [ppm]=1.81-1.96 (m, 1H), 2.12-2.31 (m, 2H), 2.42-2.60 (m, 1H), 2.80 (d, 1H), 3.11 (d, 1H), 3.48 (s, 3H), 6.17-6.52 (m, 1H), 6.98 (d, 1H), 7.06-7.21 (m, 2H), 7.29 (d, 3H), 8.81 (s, 1H), 13.26-13.64 (m, 1H).

Example 30

3-(5-Chloro-1,2,3,4-tetrahydronaphthalen-1-yl)-1-(3-methyl-2-oxo-2,3-dihydro-1,3-benzoxazol-6-yl)-5-(1H-tetrazol-5-yl)pyrimidine-2,4(1H,3H)-dione (Enantiomer 1)

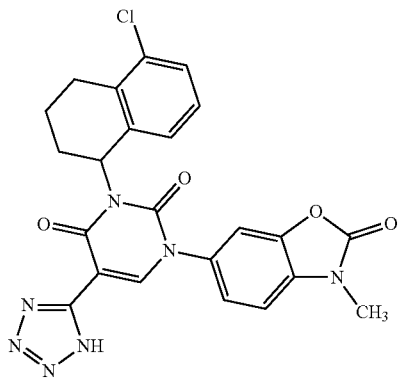 [SMILES: Cn1c(=O)oc2cc(-n3cc(-c4nnn[nH]4)c(=O)n(C4CCCc5c(Cl)cccc54)c3=O)ccc21]

Enantiomer eluting first from the chromatographic separation of 31 mg of the compound from Example 29 on a chiral phase (Method 18). Owing to solvent impurities, the resulting product was purified by means of preparative HPLC (Method 5). 7.0 mg of enantiomer 1 were obtained.

Chiral analytical HPLC (Method 17) $R_t$=7.31 min; 100% ee

LC/MS (Method 1): $R_t$=1.04 min; m/z=492 (M+H)$^+$.

Example 31

3-(5-Chloro-1,2,3,4-tetrahydronaphthalen-1-yl)-1-(3-methyl-2-oxo-2,3-dihydro-1,3-benzoxazol-6-yl)-5-(1H-tetrazol-5-yl)pyrimidine-2,4(1H,3H)-dione (Enantiomer 2)

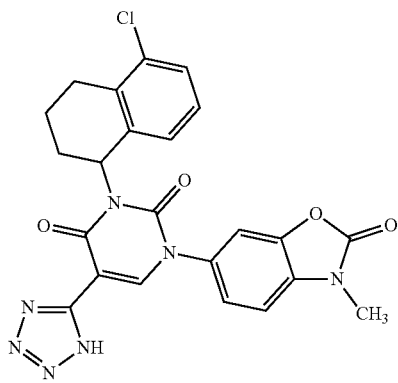

Enantiomer eluting last from the chromatographic separation of 31 mg of the compound from Example 29 on a chiral phase (Method 18). Owing to solvent impurities, the resulting product was purified by means of preparative HPLC (Method 5). 7.0 mg of enantiomer 2 were obtained.

Chiral analytical HPLC (Method 17) $R_t$=11.8 min; 99% ee

LC/MS (Method 1): $R_t$=1.04 min; m/z=492 (M+H)$^+$.

Example 32

1-(1,3-Dimethyl-2-oxo-2,3-dihydro-1H-benzimidazol-5-yl)-5-(5-oxo-4,5-dihydro-1,2,4-oxadiazol-3-yl)-3-[(1R)-4-(trifluoromethyl)-2,3-dihydro-1H-inden-1-yl]pyrimidine-2,4(1H,3H)-dione (R Enantiomer)

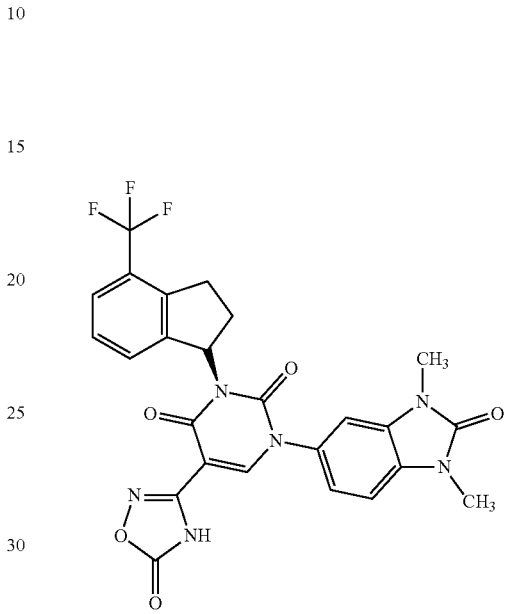

10 mg (0.025 mmol) of 1-(1,3-dimethyl-2-oxo-2,3-dihydro-1H-benzimidazol-5-yl)-N'-hydroxy-2,4-dioxo-3-[(1R)-4-(trifluoromethyl)-2,3-dihydro-1H-inden-1-yl]-1,2,3,4-tetrahydropyrimidine-5-carboximidamide from Example 36A were initially charged in 0.5 ml of DMF at RT. 2.2 mg (0.028 mmol) of pyridine were added, 3.5 mg (0.025 mmol) of isobutyl chloroformate were added dropwise and the mixture was stirred at RT for 1 h. HPLC control showed complete conversion into the intermediate. Ethyl acetate and 1 N aqueous hydrochloric acid were added to the mixture. The organic phase was separated off, washed with saturated aqueous sodium chloride solution, dried over sodium sulfate and concentrated on a rotary evaporator. The residue was dried under high vacuum. The resulting intermediate was taken up in 2 ml of xylene, 1.3 mg (0.005 mmol) of 1-ethyl-3-methyl-1H-imidazol-3-ium hexafluorophosphate were added and the mixture was reacted in a microwave at 200° C. for 1 h. The reaction mixture was concentrated and the residue was dissolved in a little DMSO/acetonitrile 1:1 (v/v) and purified by preparative HPLC (Method 6). This gave 7 mg (51% of theory) of the title compound.

LC/MS (Method 1): $R_t$=1.02 min., m/z=539 (MS/ES$^-$)

$^1$H-NMR (400 MHz, CD$_2$Cl$_2$): δ [ppm]=2.41-2.52 (m, 1H), 2.58-2.71 (m, 1H), 3.10-3.23 (m, 1H), 3.39 (s, 3H), 3.41 (s, 3H), 3.47 (d, 1H), 6.63 (br. s., 1H), 6.91-6.99 (m, 1H), 7.04 (s, 2H), 7.28-7.40 (m, 2H), 7.53 (d, 1H), 8.39 (s, 1H), 9.43-9.74 (m, 1H).

Example 33

1-(1,3-Dimethyl-2-oxo-2,3-dihydro-1H-benzimidazol-5-yl)-3-[2-methyl-3-(trifluoromethyl)benzyl]-5-(5-oxo-4,5-dihydro-1,2,4-oxadiazol-3-yl)pyrimidine-2,4(1H,3H)-dione

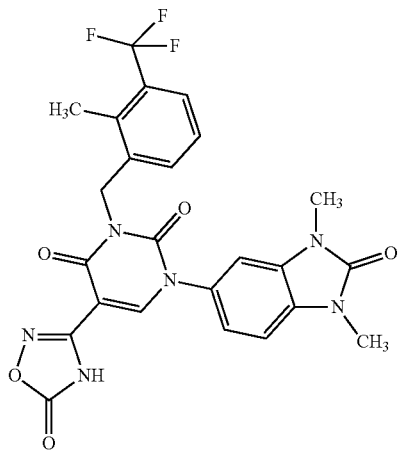 [SMILES: Cc1c(Cn2c(=O)c(-c3noc(=O)[nH]3)cn(-c3ccc4c(c3)n(C)c(=O)n4C)c2=O)cccc1C(F)(F)F]

285 mg (0.576 mmol) of 1-(1,3-dimethyl-2-oxo-2,3-dihydro-1H-benzimidazol-5-yl)-N'-hydroxy-3-[2-methyl-3-(trifluoromethyl)benzyl]-2,4-dioxo-1,2,3,4-tetrahydropyrimidine-5-carboximidamide from Example 37A were initially charged in 10 ml of DMF at RT. 49.4 mg (0.624 mmol) of pyridine were added, 77.5 mg (0.576 mmol) of isobutyl chloroformate were added dropwise and the mixture was stirred at RT for 1 h. HPLC control showed complete conversion into the intermediate. The mixture was diluted with 100 ml of water, and the solid formed was filtered off with suction, washed with water and dried in a vacuum cabinet at 60° C. The intermediate in 18 ml of acetonitrile was stirred in a microwave at 190° C. for 20 min, and the reaction mixture was subsequently concentrated. The residue was stirred with 20 ml of ethyl acetate, and the solid formed was filtered off with suction and dried. This gave 205 mg (66% of theory) of the title compound.

LC/MS (Method 1): $R_t$=0.94 min, m/z=527 (MS/ES⁻)

$^1$H-NMR (400 MHz, DMSO-$d_6$): δ [ppm]=4.95-5.31 (m, 2H), 7.23-7.31 (m, 2H), 7.34-7.39 (m, 1H), 7.41-7.46 (m, 2H), 7.61 (d, 1H), 8.41 (s, 1H), 12.36-12.70 (m, 1H).

Example 34

3-[2-Methyl-3-(trifluoromethyl)benzyl]-5-(5-oxo-4,5-dihydro-1,2,4-oxadiazol-3-yl)-1-[4-(2-oxoimidazolidin-1-yl)phenyl]pyrimidine-2,4(1H,3H)-dione

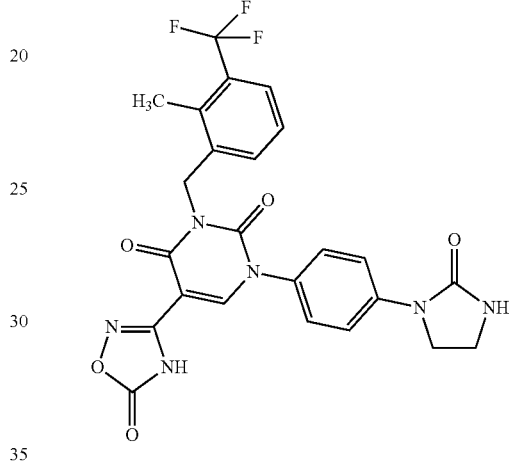

At RT, 51.6 mg (0.652 mmol) of pyridine were added to 298 mg (0.593 mmol) of N'-hydroxy-3-[2-methyl-3-(trifluoromethyl)benzyl]-2,4-dioxo-1-[4-(2-oxoimidazolidin-1-yl)phenyl]-1,2,3,4-tetrahydropyrimidine-5-carboximidamide from Example 38A in 10 ml of DMF, 81.0 mg (0.593 mmol) of isobutyl chloroformate were added dropwise and the mixture was stirred at RT for 1 h. HPLC control showed complete conversion into the intermediate. The mixture was diluted with 100 ml of water, and the solid formed was filtered off with suction, washed with water and dried in a vacuum cabinet at 60° C. The intermediate in 18 ml of acetonitrile was stirred in a microwave at 180° C. for 20 min. The reaction mixture was concentrated, the residue was stirred with 20 ml of ethyl acetate and the solid formed was filtered off with suction and dried. This gave 285 mg (84% of theory) of the title compound.

LC/MS (Method 1): $R_t$=0.92 min, m/z=527 (MS/ES⁻)

$^1$H-NMR (400 MHz, DMSO-$d_6$): δ [ppm]=3.43 (t, 2H), 3.89 (t, 2H), 5.12 (s, 2H), 7.11 (s, 1H), 7.35 (s, 1H), 7.40-7.52 (m, 3H), 7.60 (s, 1H), 7.69 (d, 2H), 8.29-8.51 (m, 1H), 12.50 (br. s., 1H).

Example 35

3-[2-Methyl-3-(trifluoromethyl)benzyl]-5-(5-oxo-4,5-dihydro-1,2,4-oxadiazol-3-yl)-1-[4-(2-oxo-1,3-oxazolidin-3-yl)phenyl]pyrimidine-2,4(1H,3H)-dione

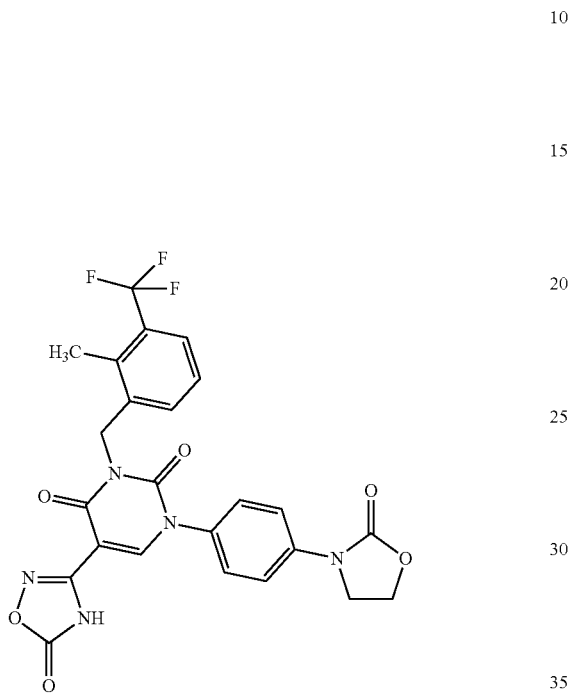

36 mg (0.072 mmol) of N'-hydroxy-3-[2-methyl-3-(trifluoromethyl)benzyl]-2,4-dioxo-1-[4-(2-oxo-1,3-oxazolidin-3-yl)phenyl]-1,2,3,4-tetrahydropyrimidine-5-carboximidamide from Example 42A were initially charged in 1.4 ml of DMF at RT, 6.2 mg (0.08 mmol) of pyridine were added, 9.8 mg (0.072 mmol) of isobutyl chloroformate were added dropwise and the mixture was stirred at RT for 1 h. HPLC control showed complete conversion into the intermediate. The mixture was diluted with 20 ml of water, and the solid formed was filtered off with suction, washed with water and dried in a vacuum cabinet at 60° C. The resulting intermediate was stirred with 2 ml of xylene in a microwave at 200° C. for 1 hour. The reaction mixture was concentrated and the residue was dissolved in a little DMSO and purified by preparative HPLC (Method 5). This gave 11 mg (29% of theory) of the title compound.

LC/MS (Method 1): $R_t$=1.0 min, m/z=528 (MS/ES$^-$)

$^1$H-NMR (400 MHz, DMSO-d$_6$): δ [ppm]=4.11 (t, 2H), 4.39-4.57 (m, 2H), 5.13 (s, 2H), 7.30-7.39 (m, 1H), 7.41-7.47 (m, 1H), 7.55-7.65 (m, 3H), 7.72 (d, 2H), 8.41 (s, 1H), 12.38-12.66 (m, 1H).

Example 36

1-(3,4-Dimethoxyphenyl)-3-[2-methyl-3-(trifluoromethyl)benzyl]-5-(5-oxo-4,5-dihydro-1,2,4-oxadiazol-3-yl)pyrimidine-2,4(1H,3H)-dione

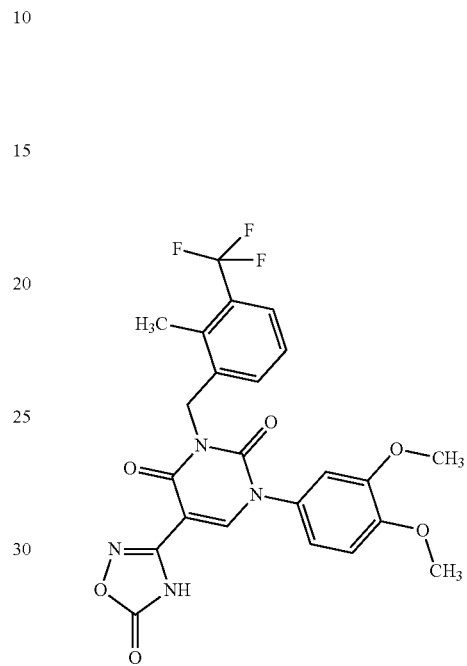

36 mg (0.075 mmol) of 1-(3,4-dimethoxyphenyl)-N'-hydroxy-3-[2-methyl-3-(trifluoromethyl)benzyl]-2,4-dioxo-1,2,3,4-tetrahydropyrimidine-5-carboximidamide from Example 39A were initially charged in 1.45 ml of DMF at RT, 6.6 mg (0.08 mmol) of pyridine were added, 10.3 mg (0.075 mmol) of isobutyl chloroformate were added dropwise and the mixture was stirred at RT for 1 h. HPLC control showed complete conversion into the intermediate. The mixture was diluted with 20 ml of water. The solid formed was filtered off with suction, washed with water and dried in a vacuum cabinet at 60° C. The resulting intermediate was stirred with 2 ml of xylene and 100 μl of 1-n-butyl-3-methylimidazolium hexafluorophosphate in a microwave at 200° C. for 1 h. The reaction mixture was concentrated and the residue was dissolved in a little DMSO and purified by preparative HPLC (Method 5). This gave 20 mg (53% of theory) of the title compound.

LC/MS (Method 1): $R_t$=1.05 min, m/z=505 (M+H)$^+$ $^1$H-NMR (400 MHz, DMSO-d$_6$): δ [ppm]=3.77 (s, 3H), 3.81 (s, 3H), 5.12 (s, 2H), 7.03-7.13 (m, 2H), 7.21 (s, 1H), 7.32-7.39 (m, 1H), 7.40-7.46 (m, 1H), 7.61 (d, 1H), 8.38 (s, 1H), 12.50 (br. s, 1H).

Example 37

1-(4-Methoxyphenyl)-3-[2-methyl-3-(trifluoromethyl)benzyl]-5-(5-oxo-4,5-dihydro-1,2,4-oxadiazol-3-yl)pyrimidine-2,4(1H,3H)-dione

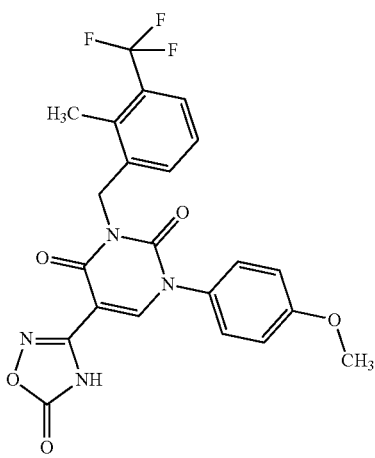 [SMILES: COc1ccc(-n2cc(-c3noc(=O)[nH]3)c(=O)n(Cc3cccc(C(F)(F)F)c3C)c2=O)cc1]

92 mg (0.168 mmol) of N'-hydroxy-1-(4-methoxyphenyl)-3-[2-methyl-3-(trifluoromethyl)benzyl]-2,4-dioxo-1,2,3,4-tetrahydropyrimidine-5-carboximidamide from Example 40A were initially charged in 2.8 ml of DMF at RT. 14.6 mg (0.185 mmol) of pyridine were added, 23.0 mg (0.168 mmol) of isobutyl chloroformate were then added dropwise at 0° C. and the mixture was stirred at RT for 40 min. HPLC control showed complete conversion into the intermediate. 56.6 mg (0.59 mmol) of sodium tert-butoxide were then added, and the mixture was stirred at RT for 30 min. 15 ml of 1N aqueous hydrochloric acid were added. The solid formed was filtered off with suction, washed with water, stirred with 10 ml of diethyl ether, once more filtered off with suction, washed with diethyl ether and dried. This gave 20 mg (23% of theory) of the title compound.

LC/MS (Method 2): $R_t$=1.28 min; m/z=475 (M+H)$^+$ $^1$H-NMR (400 MHz, DMSO-d$_6$): δ [ppm]=3.81 (br. s, 3H), 5.12 (br. s, 2H), 7.07 (d, 2H), 7.36 (d, 1H), 7.41-7.52 (m, 3H), 7.61 (d, 1H), 8.27-8.54 (m, 1H), 12.35-12.62 (m, 1H).

Example 38

1-(3-Methyl-2-oxo-2,3-dihydro-1,3-benzoxazol-6-yl)-5-(5-oxo-4,5-dihydro-1,2,4-oxadiazol-3-yl)-3-[(1R)-4-(trifluoromethyl)-2,3-dihydro-1H-inden-1-yl]pyrimidine-2,4(1H,3H)-dione (R Enantiomer)

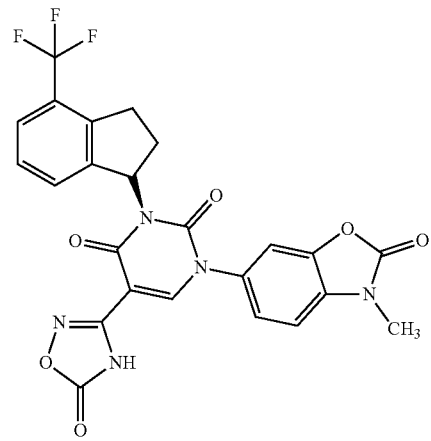

17 mg (0.03 mmol) of N'-hydroxy-1-(3-methyl-2-oxo-2,3-dihydro-1,3-benzoxazol-6-yl)-2,4-dioxo-3-[(1R)-4-(trifluoromethyl)-2,3-dihydro-1H-inden-1-yl]-1,2,3,4-tetrahydropyrimidine-5-carboximidamide from Example 41A were initially charged in 0.7 ml of DMF at RT. 2.95 mg (0.04 mmol) of pyridine were added, 4.4 mg (0.03 mmol) of isobutyl chloroformate were added dropwise and the mixture was stirred at RT for 1 h. HPLC control showed complete conversion into the intermediate. Ethyl acetate and 1 N aqueous hydrochloric acid were added to the mixture. The organic phase was separated off, washed with saturated aqueous sodium chloride solution, dried over sodium sulfate and concentrated on a rotary evaporator. The residue was dried under high vacuum. The resulting intermediate was taken up in 2 ml of xylene, 1.74 mg (0.01 mmol) of 1-ethyl-3-methyl-1H-imidazol-3-ium hexafluorophosphate were added and the mixture was reacted in a microwave at 200° C. for 1 h. The reaction mixture was concentrated and the residue was dissolved in a little DMSO/acetonitrile 1:1 (v/v) and purified by preparative HPLC (Method 6). This gave 10 mg (56% of theory) of the title compound.

LC/MS (Method 1): $R_t$=1.06 min., m/z=526 (MS/ES$^-$)

$^1$H-NMR (400 MHz, CD$_2$Cl$_2$): δ [ppm]=2.30-2.50 (m, 1H), 2.54-2.74 (m, 1H), 3.17 (m, 1H), 3.41 (s, 3H), 3.46 (d, 1H), 6.62 (br. s, 1H), 7.08 (d, 1H), 7.19 (d, 1H), 7.23-7.28 (m, 1H), 7.28-7.38 (m, 2H), 7.53 (d, 1H), 8.36 (s, 1H), 9.36-9.66 (m, 1H).

Example 39

3-[2-Methyl-3-(trifluoromethyl)benzyl]-5-(5-oxo-4,5-dihydro-1,2,4-thiadiazol-3-yl)-1-[4-(2-oxo-1,3-oxazolidin-3-yl)phenyl]pyrimidine-2,4(1H,3H)-dione

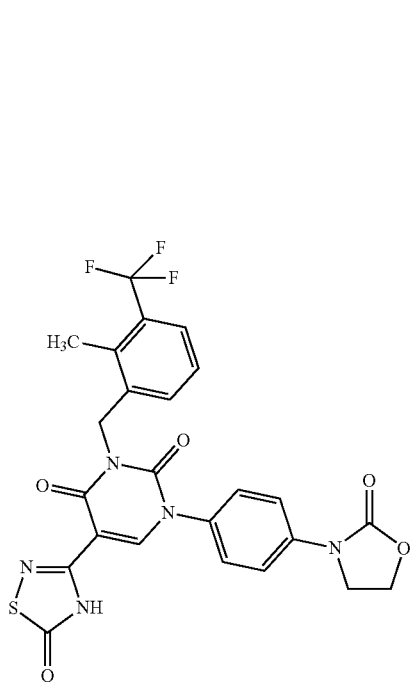 [SMILES: Cc1c(Cn2c(=O)c(-c3nsc(=O)[nH]3)cn(-c3ccc(N4CCOC4=O)cc3)c2=O)cccc1C(F)(F)F]

531 mg (2.98 mmol) of thiocarbonyldiimidazole were added to a solution of 1.00 g (1.99 mmol) of N'-hydroxy-3-[2-methyl-3-(trifluoromethyl)benzyl]-2,4-dioxo-1-[4-(2-oxo-1,3-oxazolidin-3-yl)phenyl]-1,2,3,4-tetrahydropyrimidine-5-carboximidamide from Example 42A in 40 ml of anhydrous THF, and the resulting mixture was stirred at RT for 30 min. The resulting suspension was diluted with 100 ml of water. The solid was filtered off with suction, washed with water and then dissolved in dichloromethane/methanol 10:1. The solution was dried over sodium sulfate and concentrated on a rotary evaporator. The residue was dried under high vacuum (810 mg). 730 mg of this solid were taken up in 29 ml of anhydrous THF, and 905 µl (7.1 mmol) of boron trifluoride/diethyl ether complex were added. The reaction mixture was stirred at RT overnight and then poured into 200 ml of 0.1 N aqueous hydrochloric acid. The solid formed was filtered off, dissolved in a little DMSO and purified by preparative HPLC (Method 5). This gave 96 mg (15% of theory) of the title compound.

LC/MS (Method 1): $R_t$=1.04 min, m/z=546 (M+H)$^+$ $^1$H-NMR (400 MHz, DMSO-d$_6$): δ [ppm]=2.48 (s, 3H), 4.11 (dd, 2H), 4.47 (dd, 2H), 5.13 (s, 2H), 7.36 (t, 1H), 7.44 (d, 1H), 7.55-7.64 (m, 3H), 7.71 (d, 2H), 8.41 (s, 1H), 12.76 (s, 1H).

Example 40

1-(3,4-Dimethoxyphenyl)-3-[2-methyl-3-(trifluoromethyl)benzyl]-5-(5-oxo-4,5-dihydro-1,2,4-thiadiazol-3-yl)pyrimidine-2,4(1H,3H)-dione

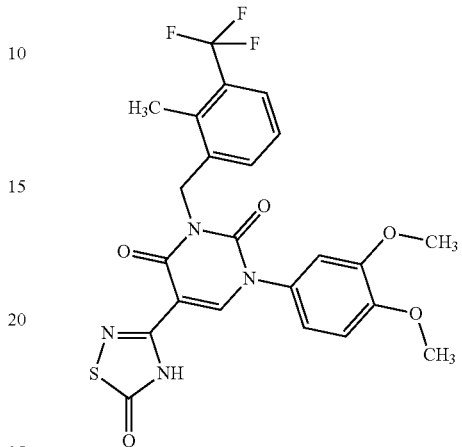

Under argon, 60 mg (0.125 mmol) of 1-(3,4-dimethoxyphenyl)-N'-hydroxy-3-[2-methyl-3-(trifluoromethyl)benzyl]-2,4-dioxo-1,2,3,4-tetrahydropyrimidine-5-carboximidamide from Example 39A were dissolved in 2.3 ml of THF. 33.5 mg (0.188 mmol) of thiocarbonyldiimidazole were added and the mixture was stirred at RT for 30 min. 53.4 mg (0.378 mmol) of boron trifluoride/diethyl ether complex was added. The mixture was stirred at RT for 1 h and at reflux temperature for 2 h, allowed to cool to RT, diluted with DMSO and separated completely by preparative HPLC (Method 5). This gave 6 mg (9% of theory) of the title compound.

LC/MS (Method 2): $R_t$=1.34 min., m/z=521 (M+H)$^+$ $^1$H-NMR (400 MHz, DMSO-d$_6$): δ [ppm]=3.77 (s, 3H), 3.80 (s, 3H), 4.96-5.28 (m, 2H), 7.04-7.11 (m, 2H), 7.21 (d, 1H), 7.32-7.39 (m, 1H), 7.40-7.45 (m, 1H), 7.61 (d, 1H), 8.37 (s, 1H), 12.76 (br. s, 1H).

Example 41

1-(3-Methyl-2-oxo-2,3-dihydro-1,3-benzoxazol-6-yl)-2,4-dioxo-3-[(1R)-4-(trifluoromethyl)-2,3-dihydro-1H-inden-1-yl]-1,2,3,4-tetrahydropyrimidine-5-carboxamide (R Enantiomer)

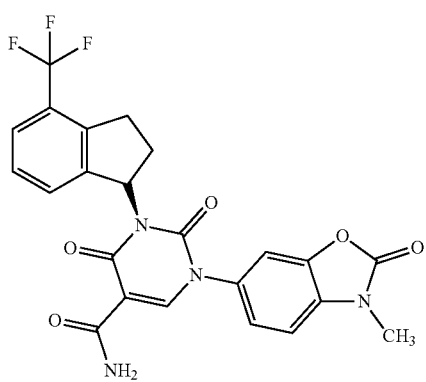

200 mg (0.41 mmol) of 1-(3-methyl-2-oxo-2,3-dihydro-1,3-benzoxazol-6-yl)-2,4-dioxo-3-[(1R)-4-(trifluoromethyl)-2,3-dihydro-1H-inden-1-yl]-1,2,3,4-tetrahydropyrimidine-5-carboxylic acid from Example 22A and 99.8 mg (0.74 mmol) of HOBt were initially charged in 10 ml of DMF. 142 mg (0.74 mmol) of EDC were added and the mixture was stirred at RT for 20 min. 2.1 ml of ammonia (35% in water) were then added and the mixture was stirred at RT for two hours. With vigorous stirring, 50 ml of water were added, and the resulting precipitate was filtered off with suction and dried under high vacuum. This gave 196 mg (94% of theory) of the title compound.

LC/MS (Method 1): $R_t$=1.03 min; m/z=487 (M+H)$^+$ $^1$H-NMR (400 MHz, CD$_2$Cl$_2$): δ [ppm]=2.39-2.53 (m, 1H), 2.61 (dtd, 1H), 3.07-3.22 (m, 1H), 3.41 (s, 3H), 3.41-3.53 (m, 1H), 5.70 (br. s, 1H), 6.51-6.71 (m, 1H), 7.06 (d, 1H), 7.18 (d, 1H), 7.24 (br. s, 1H), 7.27-7.36 (m, 2H), 7.51 (d, 1H), 7.97 (s, 1H), 8.46 (br. s, 1H).

Example 42

1-(3-Methyl-2-oxo-2,3-dihydro-1,3-benzothiazol-6-yl)-2,4-dioxo-3-[(1R)-4-(trifluoromethyl)-2,3-dihydro-1H-inden-1-yl]-1,2,3,4-tetrahydropyrimidine-5-carboxamide (R Enantiomer)

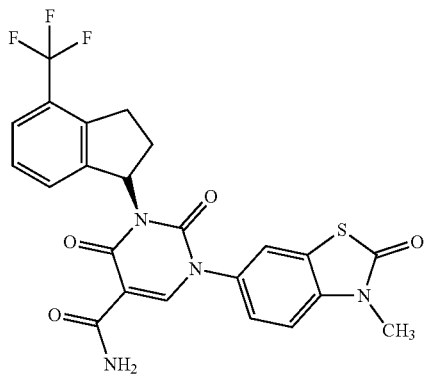

The title compound was prepared analogously to Example 41 from 220 mg (0.41 mmol; purity 94%) of the compound from Example 24A and aqueous ammonia. Yield: 190 mg (89% of theory).

LC/MS (Method 1): $R_t$: 1.07 min; m/z=503 (M+H)$^+$ $^1$H-NMR (400 MHz, CD$_2$Cl$_2$): δ [ppm]=2.40-2.53 (m, 1H), 2.56-2.68 (m, 1H), 3.10-3.22 (m, 1H), 3.42-3.53 (m, 1H), 3.45 (s, 3H), 5.70 (br. s, 1H), 6.64 (br. s, 1H), 7.13 (d, 1H), 7.26-7.37 (m, 3H), 7.45 (br. s, 1H), 7.51 (d, 1H), 8.48 (br. s, 1H), 8.52 (s, 1H).

Example 43

1-(1,3-Dimethyl-2-oxo-2,3-dihydro-1H-benzimidazol-5-yl)-2,4-dioxo-3-[(1R)-4-(trifluoromethyl)-2,3-dihydro-1H-inden-1-yl]-1,2,3,4-tetrahydropyrimidine-5-carboxamide (R Enantiomer)

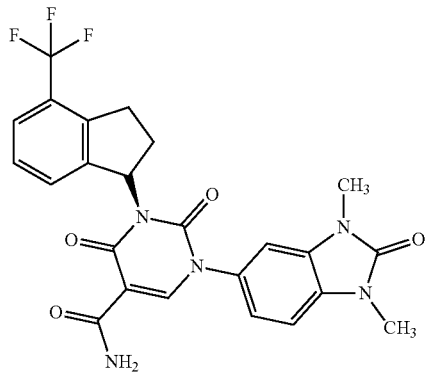

100 mg (0.2 mmol) of 1-(1,3-dimethyl-2-oxo-2,3-dihydro-1H-benzimidazol-5-yl)-2,4-dioxo-3-[(1R)-4-(trifluoromethyl)-2,3-dihydro-1H-inden-1-yl]-1,2,3,4-tetrahydropyrimidine-5-carboxylic acid from Example 23A and 37.8 mg (0.28 mmol) of HOBt were initially charged in 5 ml of DMF. 53.6 mg (0.28 mmol) of EDC were added and the mixture was stirred at RT for 20 min. 1 ml of ammonia (35% in water) was then added. The reaction mixture was stirred at RT for 4 h and then concentrated. The residue was dissolved in a little DMSO and separated by preparative HPLC (Method 6). This gave 40 mg (40% of theory) of the title compound.

LC/MS (Method 1): $R_t$=0.95 min; m/z=500 (M+H)$^+$ $^1$H-NMR (400 MHz, CD$_2$Cl$_2$): δ [ppm]=2.37-2.54 (m, 1H), 2.61 (m, 1H), 3.06-3.25 (m, 1H), 3.38 (s, 3H), 3.40 (s, 3H), 3.46 (d, 1H), 5.66-5.80 (m, 1H), 6.64 (br. s, 1H), 6.90-7.06 (m, 3H), 7.25-7.36 (m, 2H), 7.51 (d, 1H), 8.54 (s, 1H).

Example 44

Methyl N-({3-[2-methyl-3-(trifluoromethyl)benzyl]-2,4-dioxo-1-[4-(2-oxoimidazolidin-1-yl)phenyl]-1,2,3,4-tetrahydropyrimidin-5-yl}carbonyl)alaninate (Racemate)

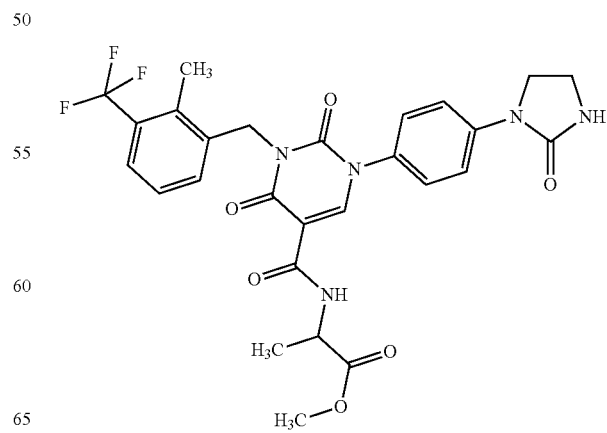

43 mg (0.31 mmol) of methyl alaninate hydrochloride (racemate), 98.6 mg (0.31 mmol) of TBTU and 169 µl (1.54 mmol) of N-methylmorpholine were added to 150 mg (0.31 mmol) of 3-[2-methyl-3-(trifluoromethyl)benzyl]-2,4-dioxo-1-[4-(2-oxoimidazolidin-1-yl)phenyl]-1,2,3,4-tetrahydropyrimidine-5-carboxylic acid (Example 25A) in 3.75 ml of dichloromethane, and the mixture was stirred at RT for 22 h. The mixture was concentrated to dryness on a rotary evaporator and the residue was taken up in 1 ml of DMF and 5 ml of acetonitrile. The suspension formed was diluted with 50 ml of water and stirred for 5 min. The solid was filtered off, washed with water and dried under high vacuum. This gave 154 mg (83% of theory) of the title compound.

LC/MS (Method 1): $R_t$=1.09 min; m/z=574 (M+H)$^+$ $^1$H-NMR (400 MHz, DMSO-d$_6$): δ [ppm]=1.38 (d, 3H), 2.47 (s, 3H), 3.43 (t, 2H), 3.65 (s, 3H), 3.85-3.92 (m, 2H), 4.52 (quin, 1H), 5.14 (s, 2H), 7.11 (s, 1H), 7.31-7.38 (m, 1H), 7.39-7.43 (m, 1H), 7.45-7.51 (m, 2H), 7.61 (d, 1H), 7.66-7.72 (m, 2H), 8.34 (s, 1H), 9.10 (d, 1H).

Example 45

N-({3-[2-Methyl-3-(trifluoromethyl)benzyl]-2,4-dioxo-1-[4-(2-oxoimidazolidin-1-yl)phenyl]-1,2,3,4-tetrahydropyrimidin-5-yl}carbonyl)alanine (Racemate)

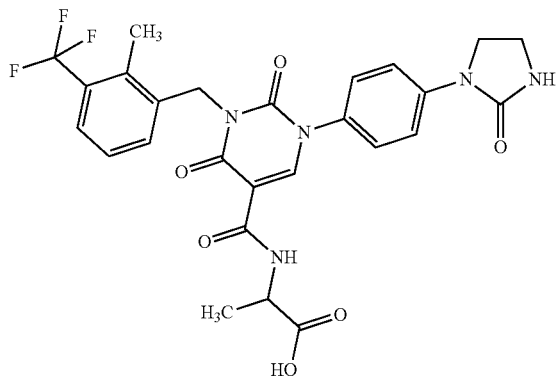 [SMILES: Cc1c(Cn2c(=O)c(C(=O)NC(C)C(=O)O)cn(-c3ccc(N4CCNC4=O)cc3)c2=O)cccc1C(F)(F)F]

116 mg (0.2 mmol) of methyl N-({3-[2-methyl-3-(trifluoromethyl)benzyl]-2,4-dioxo-1-[4-(2-oxoimidazolidin-1-yl)phenyl]-1,2,3,4-tetrahydropyrimidin-5-yl}carbonyl)alaninate (racemate) from Example 44 were dissolved in 2 ml of acetic acid, 1 ml of conc. hydrochloric acid and 1 ml of water, and the mixture was stirred at 60° C. for 28 hours. The mixture was diluted with 50 ml of water and the precipitate formed was filtered off with suction. The product was dissolved and separated by preparative HPLC (Method 8). This gave 62 mg (53% of theory) of the title compound.

LC/MS (Method 4): $R_t$=2.14 min m/z=560 (M+H)$^+$ $^1$H-NMR (400 MHz, DMSO-d$_6$): δ [ppm]=1.37 (d, 3H), 3.43 (t, 2H), 3.83-3.96 (m, 2H), 4.43 (s, 1H), 5.02-5.23 (m, 2H), 7.11 (s, 1H), 7.32-7.42 (m, 2H), 7.48 (d, 2H), 7.61 (d, 1H), 7.70 (d, 2H), 8.27-8.40 (m, 1H), 9.13 (d, 1H), 12.93 (br. s., 1H).

Example 46

Methyl N-({3-[2-methyl-3-(trifluoromethyl)benzyl]-2,4-dioxo-1-(1,3,3-trimethyl-2-oxo-2,3-dihydro-1H-indol-5-yl)-1,2,3,4-tetrahydropyrimidin-5-yl}carbonyl)alaninate (Racemate)

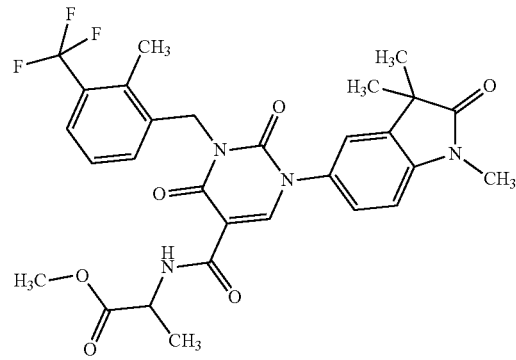 [SMILES: COC(=O)C(C)NC(=O)c1cn(-c2ccc3c(c2)C(C)(C)C(=O)N3C)c(=O)n(Cc2cccc(C(F)(F)F)c2C)c1=O]

92 mg (0.48 mmol) of EDC and 73 mg (0.48 mmol) of HOBt were added to 200 mg (0.40 mmol) of 3-[2-methyl-3-(trifluoromethyl)benzyl]-2,4-dioxo-1-(1,3,3-trimethyl-2-oxo-2,3-dihydro-1H-indol-5-yl)-1,2,3,4-tetrahydropyrimidine-5-carboxylic acid from Example 28A in 2.2 ml of DMF, and the reaction mixture was stirred at RT for 10 min. 62 mg (0.60 mmol) of DL-methyl alaninate (racemate) and 0.10 ml (0.60 mmol) of N,N-diisopropylethylamine were then added, and the reaction mixture was stirred further at RT overnight. Water was then added, and the mixture was filtered. The filter residue was washed with water and dried under high vacuum at 50° C. The resulting residue was purified by Versaflash® silica gel chromatography (dichloromethane/methanol gradient 120:1 to 20:1). This gave, after concentration of the appropriate fractions and drying under reduced pressure, 172 mg (73% of theory) of the target compound.

LC-MS (Method 1): $R_t$=1.14 min; MS (ESIpos): m/z=587 (M+H)$^+$.

$^1$H-NMR (400 MHz, DMSO-d$_6$): δ=1.30 (s, 6H), 1.38 (d, 3H), 2.47 (s, 3H), 3.18 (s, 3H), 3.65 (s, 3H), 4.43-4.57 (m, 1H), 5.14 (s, 2H), 7.16 (d, 1H), 7.33-7.43 (m, 2H), 7.45-7.50 (m, 1H), 7.56 (d, 1H), 7.59-7.64 (m, 1H), 8.36 (s, 1H), 8.96-9.28 (m, 1H).

Example 47

N-({3-[2-Methyl-3-(trifluoromethyl)benzyl]-2,4-dioxo-1-(1,3,3-trimethyl-2-oxo-2,3-dihydro-1H-indol-5-yl)-1,2,3,4-tetrahydropyrimidin-5-yl}carbonyl)alanine (Racemate)

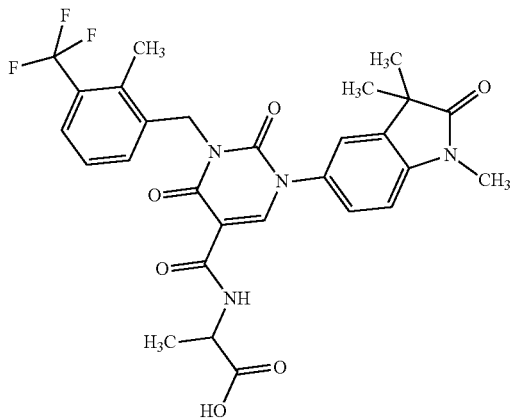 [SMILES: Cc1c(Cn2c(=O)c(C(=O)NC(C)C(=O)O)cn(-c3ccc4c(c3)C(C)(C)C(=O)N4C)c2=O)cccc1C(F)(F)F]

171 mg (0.29 mmol) of methyl N-({3-[2-methyl-3-(trifluoromethyl)benzyl]-2,4-dioxo-1-(1,3,3-trimethyl-2-oxo-2,3-dihydro-1H-indol-5-yl)-1,2,3,4-tetrahydropyrimidin-5-yl}carbonyl)alaninate from Example 46 were stirred in 2 ml of acetic acid and 1 ml of conc. hydrochloric acid at 120° C. for 1 hour. After cooling to RT, the reaction mixture was diluted with water and the precipitate formed was filtered off with suction, washed with a little MTBE and dried under reduced pressure. This gave 145 mg (85% of theory) of the title compound.

LC/MS (Method 1): $R_t$=1.02 min m/z=573 (M+H)$^+$ $^1$H-NMR (400 MHz, DMSO-d$_6$): δ=1.30 (s, 6H), 1.37 (d, 3H), 2.47 (s, 3H), 3.18 (s, 3H), 4.39-4.48 (m, 1H), 5.14 (s, 2H), 7.16 (d, 1H), 7.33-7.42 (m, 2H), 7.45-7.50 (m, 1H), 7.54-7.57 (m, 1H), 7.59-7.64 (m, 1H), 8.36 (s, 1H), 9.13 (d, 1H), 12.83-13.01 (m, 1H).

Example 48

Ethyl N-({1-(1,3-dimethyl-2-oxo-2,3-dihydro-1H-benzimidazol-5-yl)-3-[2-methyl-3-(trifluoromethyl)benzyl]-2,4-dioxo-1,2,3,4-tetrahydropyrimidin-5-yl}carbonyl)-2-methylalaninate

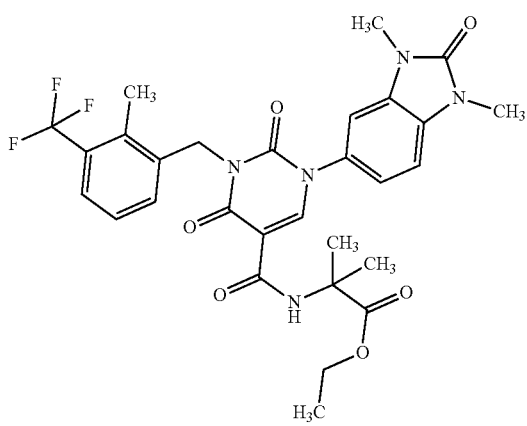 [SMILES: CCOC(=O)C(C)(C)NC(=O)c1cn(-c2ccc3c(c2)n(C)c(=O)n3C)c(=O)n(Cc2cccc(C(F)(F)F)c2C)c1=O]

118 mg (0.61 mmol) of EDC and 94 mg (0.61 mmol) of HOBt were added to 250 mg (0.51 mmol) of 1-(1,3-dimethyl-2-oxo-2,3-dihydro-1H-benzimidazol-5-yl)-3-[2-methyl-3-(trifluoromethyl)benzyl]-2,4-dioxo-1,2,3,4-tetrahydropyrimidine-5-carboxylic acid from Example 26A in 2.8 ml of DMF, and the reaction mixture was stirred at RT for 10 min. 129 mg (0.77 mmol) of ethyl 2-methylalaninate hydrochloride and 0.22 ml (1.28 mmol) of N,N-diisopropylethylamine were then added, and the reaction mixture was stirred at RT for a further 3 days. Water was then added, and the mixture was filtered. The filter residue was washed with water and dried under high vacuum at 50° C. This gave 268 mg (85% of theory) of the target compound.

LC-MS (Method 1): $R_t$=1.20 min; MS (ESIpos): m/z=602 (M+H)$^+$.

$^1$H-NMR (400 MHz, DMSO-d$_6$): δ=1.15 (t, 3H), 1.47 (s, 6H), 2.47 (s, 3H), 3.31 (s, 3H), 3.37 (s, 3H), 4.07 (q, 2H), 5.14 (s, 2H), 7.24-7.30 (m, 2H), 7.33-7.39 (m, 1H), 7.40-7.46 (m, 2H), 7.61 (d, 1H), 8.35 (s, 1H), 9.11 (br. s, 1H).

Example 49

N-({1-(1,3-Dimethyl-2-oxo-2,3-dihydro-1H-benzimidazol-5-yl)-3-[2-methyl-3-(trifluoromethyl)benzyl]-2,4-dioxo-1,2,3,4-tetrahydropyrimidin-5-yl}carbonyl)-2-methylalanine

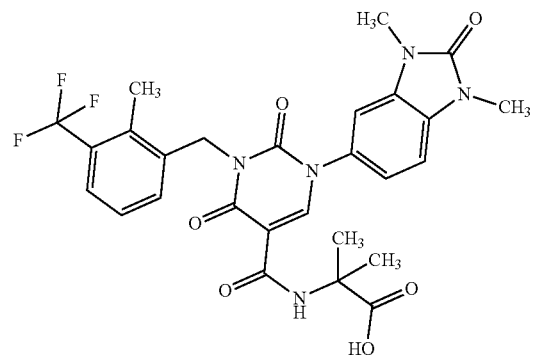 [SMILES: Cc1c(Cn2c(=O)c(C(=O)NC(C)(C)C(=O)O)cn(-c3ccc4c(c3)n(C)c(=O)n4C)c2=O)cccc1C(F)(F)F]

211 mg (0.35 mmol) of ethyl N-({1-(1,3-dimethyl-2-oxo-2,3-dihydro-1H-benzimidazol-5-yl)-3-[2-methyl-3-(trifluoromethyl)benzyl]-2,4-dioxo-1,2,3,4-tetrahydropyrimidin-5-yl}carbonyl)-2-methylalaninate from Example 48 in 2 ml of acetic acid and 1 ml of conc. hydrochloric acid were heated at 120° C. for 45 min. After cooling to RT, the reaction mixture was diluted with water and the precipitate formed was filtered off with suction and dried under high vacuum. This gave 180 mg (87% of theory) of the target compound.

LC/MS (Method 1): $R_t$=1.00 min; m/z=574 (M+H)$^+$ $^1$H-NMR (400 MHz, DMSO-d$_6$): δ [ppm]=1.49 (s, 6H), 2.47 (s, 3H), 3.31 (s, 3H), 3.37 (s, 3H), 5.14 (s, 2H), 7.24-7.31 (m, 2H), 7.33-7.44 (m, 3H), 7.54-7.65 (m, 1H), 8.35 (s, 1H), 9.07-9.33 (m, 1H), 12.68 (br. s, 1H).

Example 50

Ethyl 1-[({1-(1,3-dimethyl-2-oxo-2,3-dihydro-1H-benzimidazol-5-yl)-3-[2-methyl-3-(trifluoromethyl)benzyl]-2,4-dioxo-1,2,3,4-tetrahydropyrimidin-5-yl}carbonyl)amino]cyclobutanecarboxylate

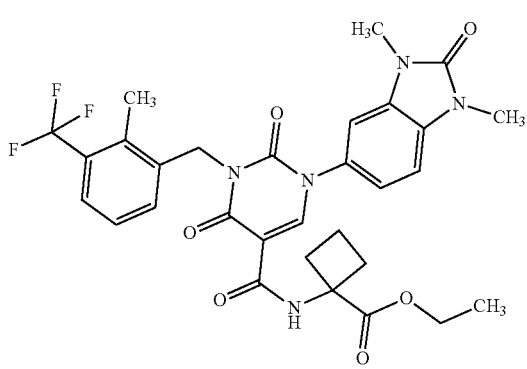 [SMILES: CCOC(=O)C1(NC(=O)c2cn(-c3ccc4c(c3)n(C)c(=O)n4C)c(=O)n(Cc3cccc(C(F)(F)F)c3C)c2=O)CCC1]

118 mg (0.61 mmol) of EDC and 94 mg (0.61 mmol) of HOBt were added to 250 mg (0.51 mmol) of 1-(1,3-dimethyl-2-oxo-2,3-dihydro-1H-benzimidazol-5-yl)-3-[2-methyl-3-(trifluoromethyl)benzyl]-2,4-dioxo-1,2,3,4-tetrahydropyrimidine-5-carboxylic acid from Example 26A in 2.8 ml of DMF, and the reaction mixture was stirred at RT for 10 min. 138 mg (0.77 mmol) of ethyl 1-aminocyclobutanecarboxylate hydrochloride and 0.22 ml (1.28 mmol) of N,N-diisopropylethylamine were then added, and the reaction mixture was stirred at RT for 3 days. Water was then added, and the mixture was filtered. The filter residue was washed with water and dried under high vacuum at 50° C. This gave 306 mg (95% of theory) of the target compound.

LC-MS (Method 1): $R_t$=1.21 min; MS (ESIpos): m/z=614 (M+H)$^+$.

$^1$H-NMR (400 MHz, DMSO-d$_6$): δ=1.17 (t, 3H), 1.86-1.99 (m, 2H), 2.21-2.34 (m, 2H), 2.48 (s, 3H), 2.50-2.60 (m, 2H, partially obscured by DMSO signal), 3.31 (s, 3H), 3.37 (s, 3H), 4.10 (q, 2H), 5.15 (s, 2H), 7.23-7.30 (m, 2H), 7.32-7.40 (m, 1H), 7.41-7.46 (m, 2H), 7.62 (d, 1H), 8.34 (s, 1H), 9.23 (s, 1H).

Example 51

1-[({1-(1,3-Dimethyl-2-oxo-2,3-dihydro-1H-benzimidazol-5-yl)-3-[2-methyl-3-trifluoromethyl)benzyl]-2,4-dioxo-1,2,3,4-tetrahydropyrimidin-5-yl}carbonyl)amino]cyclobutanecarboxylic acid

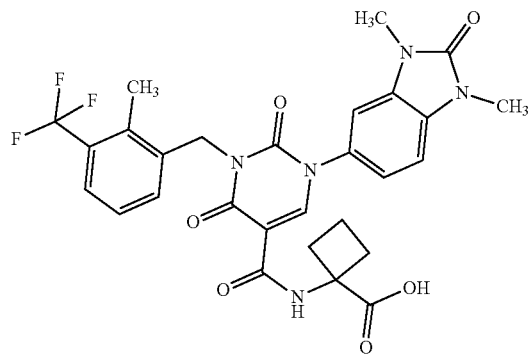 [SMILES: Cc1c(Cn2c(=O)c(C(=O)NC3(C(=O)O)CCC3)cn(-c3ccc4c(c3)n(C)c(=O)n4C)c2=O)cccc1C(F)(F)F]

50 mg (0.08 mmol) of ethyl 1-[({1-(1,3-dimethyl-2-oxo-2,3-dihydro-1H-benzimidazol-5-yl)-3-[2-methyl-3-(trifluoromethyl)benzyl]-2,4-dioxo-1,2,3,4-tetrahydropyrimidin-5-yl}carbonyl)amino]cyclobutanecarboxylate from Example 50 were stirred in 0.5 ml of acetic acid and 0.25 ml of conc. hydrochloric acid at 120° C. for 30 min. After cooling to RT, the reaction mixture was diluted with water and the solid formed was filtered off with suction and dried under vacuum. This gave 32 mg (66% of theory) of the title compound.

LC/MS (Method 1): $R_t$: 1.02 min m/z=586 (M+H)$^+$ $^1$H-NMR (400 MHz, DMSO-d$_6$): δ=1.87-2.00 (m, 2H), 2.26-2.37 (m, 2H), 2.47 (s, 3H), 2.50-2.60 (m, 2H, partially obscured by DMSO signal), 3.31 (s, 3H), 3.37 (s, 3H), 5.15 (s, 2H), 7.28 (s, 2H), 7.33-7.40 (m, 1H), 7.40-7.45 (m, 2H), 7.62 (d, 1H), 8.35 (s, 1H), 9.22 (s, 1H), 12.64 (br. s, 1H).

Example 52

3-[2-Methyl-3-(trifluoromethyl)benzyl]-2,4-dioxo-1-[4-(2-oxoimidazolidin-1-yl)phenyl]-1,2,3,4-tetrahydropyrimidine-5-carboxamide

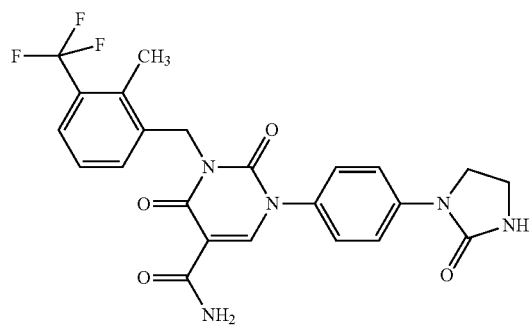 [SMILES: Cc1c(Cn2c(=O)c(C(N)=O)cn(-c3ccc(N4CCNC4=O)cc3)c2=O)cccc1C(F)(F)F]

300 mg (0.61 mmol) of the compound from Example 25A and 149.4 mg (1.11 mmol) of HOBt were initially charged in 11 ml of DMF. 212 mg (1.11 mmol) of EDC were added and the mixture was stirred at RT for 20 min. 2.3 ml of ammonia solution (35% in water) were then added. The reaction solution was stirred at RT for 3 h and then concentrated, and 100 ml of 1N aqueous hydrochloric acid were added. The solid formed was filtered off with suction and dried under high vacuum. Since, according to LC-MS, the reaction was incomplete, the product obtained was once more dissolved in 11 ml of DMF, and 109 mg (0.81 mmol) of HOBt and 154.7 mg (0.81 mmol) of EDC were added. After 20 min at RT, 2 ml of ammonia solution (35% in water) were added and the mixture was stirred at RT for 2 hours. The mixture was concentrated again and diluted with 100 ml of 1N aqueous hydrochloric acid, and the solid formed was filtered off with suction and dried under high vacuum. This gave 274 mg (92% of theory) of the title compound.

LC/MS (Method 1): R$_t$: 0.98 min m/z=488 (M+H)$^+$ $^1$H-NMR (400 MHz, DMSO-d$_6$): δ [ppm]=3.43 (t, 2H), 3.80-4.01 (m, 2H), 4.96-5.28 (m, 2H), 7.11 (s, 1H), 7.31-7.41 (m, 2H), 7.45-7.50 (m, 2H), 7.60 (d, 1H), 7.67-7.72 (m, 3H), 8.12 (d, 1H), 8.33 (s, 1H).

Example 53

Methyl N-({3-[2-methyl-3-(trifluoromethyl)benzyl]-2,4-dioxo-1-[4-(2-oxoimidazolidin-1-yl)phenyl]-1,2,3,4-tetrahydropyrimidin-5-yl}carbonyl)-beta-alaninate

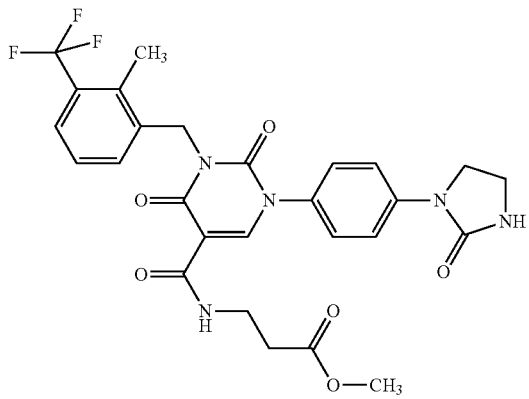 [SMILES: COC(=O)CCNC(=O)c1cn(-c2ccc(N3CCNC3=O)cc2)c(=O)n(Cc2cccc(C(F)(F)F)c2C)c1=O]

Under argon, 150 mg (0.31 mmol) of 3-[2-methyl-3-(trifluoromethyl)benzyl]-2,4-dioxo-1-[4-(2-oxoimidazolidin-1-yl)phenyl]-1,2,3,4-tetrahydropyrimidine-5-carboxylic acid from Example 25A were initially charged in 3.75 ml of dichloromethane. 42.9 mg (0.31 mmol) of beta-alanine methyl ester hydrochloride, 98.6 mg (0.31 mmol) of (benzotriazol-1-yloxy)bisdimethylaminomethylium fluoroborate and 155.3 mg (1.54 mmol) of 4-methylmorpholine were added, and the mixture was stirred at RT for 22 h. The mixture was concentrated and separated by preparative HPLC (Method 8). This gave 92 mg (49% of theory) of the title compound.

LC/MS (Method 1): R$_t$: 1.05 min m/z=574 (M+H)$^+$ $^1$H-NMR (400 MHz, DMSO-d$_6$): δ [ppm]=2.47 (s, 3H), 2.56 (t, 2H, partially under the solvent signal), 3.43 (t, 2H), 3.51 (q, 2H), 3.59 (s, 3H), 3.76-3.96 (m, 2H), 5.12 (s, 2H), 7.11 (s, 1H), 7.31-7.41 (m, 2H), 7.47 (d, 2H), 7.60 (d, 1H), 7.67-7.72 (m, 2H), 8.22-8.42 (m, 1H), 8.90 (t, 1H).

Example 54

N-({3-[2-Methyl-3-(trifluoromethyl)benzyl]-2,4-dioxo-1-[4-(2-oxoimidazolidin-1-yl)phenyl]-1,2,3,4-tetrahydropyrimidin-5-yl}carbonyl)-beta-alanine

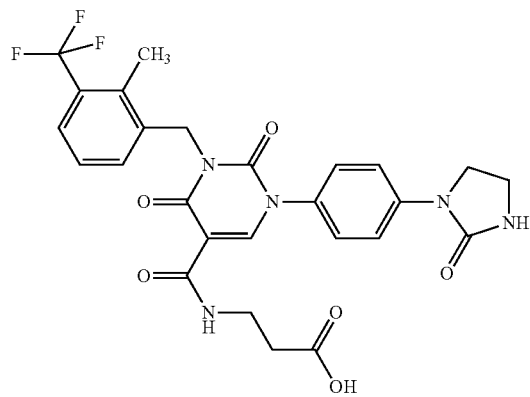 [SMILES: Cc1c(Cn2c(=O)c(C(=O)NCCC(=O)O)cn(-c3ccc(N4CCNC4=O)cc3)c2=O)cccc1C(F)(F)F]

58 mg (0.10 mmol) of methyl N-({3-[2-methyl-3-(trifluoromethyl)benzyl]-2,4-dioxo-1-[4-(2-oxoimidazolidin-1-yl)phenyl]-1,2,3,4-tetrahydropyrimidin-5-yl}carbonyl)-beta-alaninate from Example 53 were dissolved in a mixture of 1 ml of glacial acetic acid, 0.5 ml of conc. hydrochloric acid and 0.5 ml of water, and the mixture was then stirred at 60° C. for 4 h. After cooling to RT, the mixture was diluted with 50 ml of water. After a few minutes, the precipitate was filtered off with suction, washed with water and dried under high vacuum. The crude product was purified by preparative HPLC (Method 10). This gave 11 mg (19% of theory) of the title compound.

LC-MS (Method 4): R$_t$=2.05 min, MS (ESIpos): m/z=560 (M+H)$^+$.

$^1$H-NMR (400 MHz, DMSO-d$_6$): δ=2.4-2.6 (partially obscured by DMSO signal), 3.39-3.50 (m, 4H), 3.82-3.92 (m, 2H), 4.41-4.45 (m, 1H), 5.12 (s, 2H), 7.10 (s, 1H), 7.31-7.41 (m, 2H), 7.45 (d, 2H), 7.59 (d, 1H), 7.68 (d, 2H), 8.32 (s, 1H) 8.90 (t, 1H), 12.30 (br. s, 1H).

Example 55

N-Cyanomethyl-3-[2-methyl-3-(trifluoromethyl)benzyl]-2,4-dioxo-1-[4-(2-oxoimidazolidin-1-yl)phenyl]-1,2,3,4-tetrahydropyrimidine-5-carboxamide

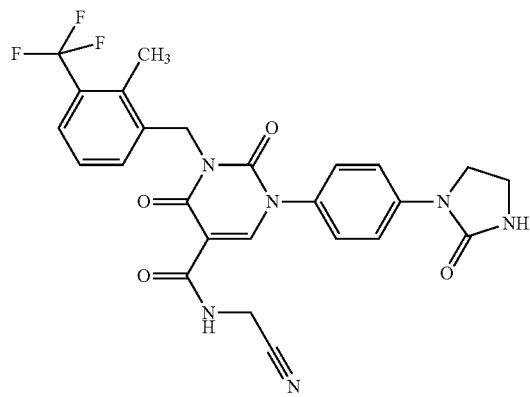 [SMILES: Cc1c(Cn2c(=O)c(C(=O)NCC#N)cn(-c3ccc(N4CCNC4=O)cc3)c2=O)cccc1C(F)(F)F]

Under argon, 150 mg (0.31 mmol) of 3-[2-methyl-3-(trifluoromethyl)benzyl]-2,4-dioxo-1-[4-(2-oxoimidazolidin-1-yl)phenyl]-1,2,3,4-tetrahydropyrimidine-5-carboxylic acid (Example 25A) were initially charged in 3.75 ml of dichloromethane. 34.4 mg (0.61 mmol) of aminoacetonitrile, 98.6 mg (0.31 mmol) of (benzotriazol-1-yloxy)bisdimethylaminomethylium fluoroborate and 155.3 mg (1.54 mmol) of 4-methylmorpholine were added, and the mixture was stirred at RT for 22 h. The mixture was diluted with 1 ml of DMF and 5 ml of acetonitrile and added to 50 ml of water. The precipitate formed was filtered off with suction, washed with water and dried under high vacuum. This gave 132 mg (76% of theory) of the title compound.

LC/MS (Method 1): $R_t$: 1.01 min m/z=527 (M+H)$^+$ $^1$H-NMR (400 MHz, DMSO-d$_6$): δ [ppm]=2.48 (s, 3H), 3.43 (t, 2H), 3.86-3.93 (m, 2H), 4.29 (d, 2H), 5.02-5.23 (m, 2H), 7.11 (s, 1H), 7.31-7.37 (m, 1H), 7.40-7.44 (m, 1H), 7.49 (d, 2H), 7.60 (d, 1H), 7.67-7.73 (m, 2H), 8.34-8.46 (m, 1H), 9.15 (t, 1H).

Example 56

Methyl N-({1-(1-methyl-1H-benzimidazol-5-yl)-3-[2-methyl-3-(trifluoromethyl)benzyl]-2,4-dioxo-1,2,3,4-tetrahydropyrimidin-5-yl}carbonyl)alaninate (Racemate)

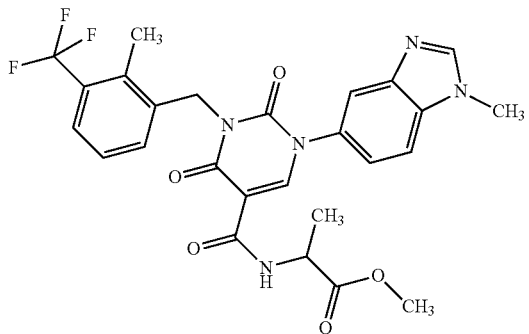 [SMILES: COC(=O)C(C)NC(=O)c1cn(-c2ccc3c(c2)ncn3C)c(=O)n(Cc2cccc(C(F)(F)F)c2C)c1=O]

100 mg (0.52 mmol) of EDC and 80 mg (0.52 mmol) of HOBt were added to 200 mg (0.44 mmol) of 1-(1-methyl-1H-benzimidazol-5-yl)-3-[2-methyl-3-(trifluoromethyl)benzyl]-2,4-dioxo-1,2,3,4-tetrahydropyrimidine-5-carboxylic acid from Example 27A in 2.4 ml of DMF, and the reaction mixture was stirred at RT for 10 min. 67 mg (0.65 mmol) of DL-methyl alaninate (racemate) and 0.11 ml (0.65 mmol) of N,N-diisopropylethylamine were then added, and the reaction mixture was stirred at RT overnight. Water was then added, and the mixture was filtered. The filter residue was washed with water and dried under high vacuum at 50° C. The resulting residue was purified by Versaflash® silica gel chromatography (dichloromethane/methanol 70:1). This gave, after concentration of the appropriate fractions and drying under reduced pressure, 117 mg (49% of theory) of the target compound.

LC-MS (Method 2): $R_t$=1.22 min; MS (ESIpos): m/z=544 (M+H)$^+$.

$^1$H-NMR (400 MHz, DMSO-d$_6$): δ=1.38 (d, 3H), 2.48 (s, 3H), 3.65 (s, 3H), 3.89 (s, 3H), 4.46-4.59 (m, 1H), 5.16 (s, 2H), 7.32-7.40 (m, 1H), 7.41-7.49 (m, 2H), 7.61 (d, 1H), 7.72 (d, 1H), 7.86-7.94 (m, 1H), 8.33 (s, 1H), 8.41 (s, 1H), 9.13 (d, 1H).

Example 57

N-({1-(1-Methyl-1H-benzimidazol-5-yl)-3-[2-methyl-3-(trifluoromethyl)benzyl]-2,4-dioxo-1,2,3,4-tetrahydropyrimidin-5-yl}carbonyl)alanine (Racemate)

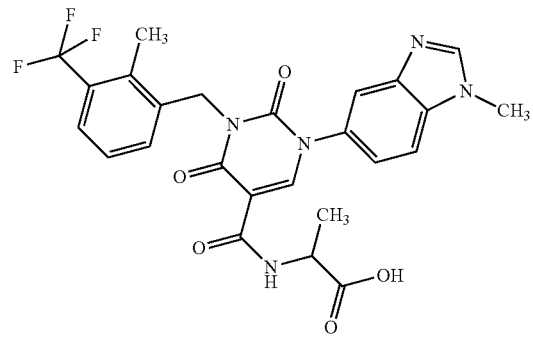 [SMILES: Cc1c(Cn2c(=O)c(C(=O)NC(C)C(=O)O)cn(-c3ccc4c(c3)ncn4C)c2=O)cccc1C(F)(F)F]

117 mg (0.22 mmol) of methyl N-({1-(1-methyl-1H-benzimidazol-5-yl)-3-[2-methyl-3-(trifluoromethyl)benzyl]-2,4-dioxo-1,2,3,4-tetrahydropyrimidin-5-yl}carbonyl)-DL-alaninate (racemate) from Example 56 were initially charged in 2.4 ml of an acetic acid/hydrochloric acid mixture (2:1 v/v), and the mixture was stirred at 120° C. for 1 h. Water was then added at RT, and the mixture was filtered. The filter residue was washed with water and MTBE and dried under high vacuum at 50° C. This gave 75 mg (64% of theory) of the target compound.

LC-MS (Method 1): $R_t$=0.85 min; MS (ESIpos): m/z=530 (M+H)$^+$.

$^1$H-NMR (400 MHz, DMSO-d$_6$): δ=1.37 (d, 3H), 2.48 (s, 3H), 3.95 (s, 3H), 4.39-4.49 (m, 1H), 5.16 (s, 2H), 7.33-7.40 (m, 1H), 7.42-7.47 (m, 1H), 7.53-7.59 (m, 1H), 7.59-7.65 (m, 1H), 7.84 (d, 1H), 7.97 (s, 1H), 8.43 (s, 1H), 8.70 (br. s, 1H), 9.15 (d, 1H), 12.64-13.18 (m, 1H).

Example 58

Methyl N-{[3-(2,3-dichlorobenzyl)-1-(4-methoxyphenyl)-2,4-dioxo-1,2,3,4-tetrahydropyrimidin-5-yl]carbonyl}-beta-alaninate

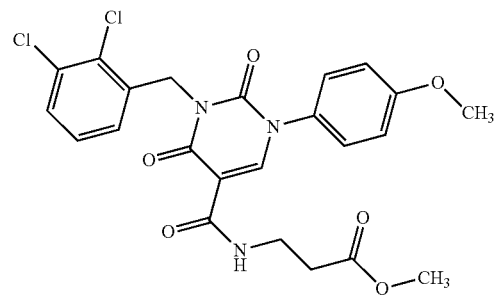 [SMILES: COC(=O)CCNC(=O)c1cn(-c2ccc(OC)cc2)c(=O)n(Cc2cccc(Cl)c2Cl)c1=O]

Analogously to Example 44, 300 mg (0.71 mmol) of 3-(2,3-dichlorobenzyl)-1-(4-methoxyphenyl)-2,4-dioxo-1,2,3,4-tetrahydropyrimidine-5-carboxylic acid from Example 21A were reacted with 99.4 mg (0.71 mmol) of beta-alanine methyl ester hydrochloride using TBTU and N-methylmorpholine, and the product was isolated. This gave 261 mg (72% of theory) of the title compound.

LC/MS (Method 1): $R_t$=1.18 min; m/z=506 (M+H)$^+$ $^1$H-NMR (400 MHz, DMSO-d$_6$): δ [ppm]=2.56-2.60 (m, 2H, partially under the DMSO signal), 3.51 (q, 2H), 3.59 (s, 3H), 3.81 (s, 3H), 5.14 (s, 2H), 7.07 (d, 2H), 7.21-7.26 (m, 1H), 7.28-7.36 (m, 1H), 7.46 (d, 2H), 7.58 (d, 1H), 8.31 (s, 1H), 8.86 (t, 1H).

Example 59

N-{[3-(2,3-Dichlorobenzyl)-1-(4-methoxyphenyl)-2,4-dioxo-1,2,3,4-tetrahydropyrimidin-5-yl]carbonyl}-beta-alanine

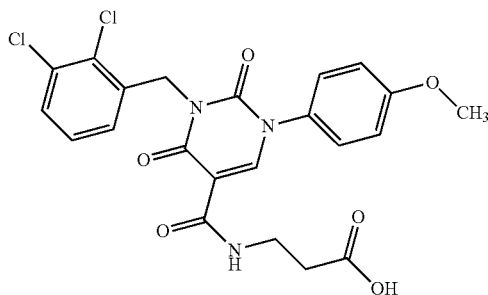 [SMILES: COc1ccc(-n2cc(C(=O)NCCC(=O)O)c(=O)n(Cc3cccc(Cl)c3Cl)c2=O)cc1]

227 mg (0.45 mmol) of the compound from Example 58 were hydrolyzed analogously to Example 49. The product was filtered off and additionally purified by preparative HPLC (Method 7). This gave 149 mg (68% of theory) of the title compound.

LC/MS (Method 1): $R_t$=1.04 min; m/z=492 (M+H)$^+$ $^1$H-NMR (400 MHz, DMSO-d$_6$): δ [ppm]=2.46 (t, 2H), 3.47 (q, 2H), 3.81 (s, 3H), 5.13 (s, 2H), 7.04-7.10 (m, 2H), 7.20-7.26 (m, 1H), 7.28-7.35 (m, 1H), 7.43-7.49 (m, 2H), 7.56-7.60 (m, 1H), 8.31 (s, 1H), 8.86 (t, 1H), 12.29 (br. s, 1H).

Example 60

Methyl O-tert-butyl-N-({3-[2-methyl-3-(trifluoromethyl)benzyl]-2,4-dioxo-1-[4-(2-oxoimidazolidin-1-yl)phenyl]-1,2,3,4-tetrahydropyrimidin-5-yl}carbonyl)serinate

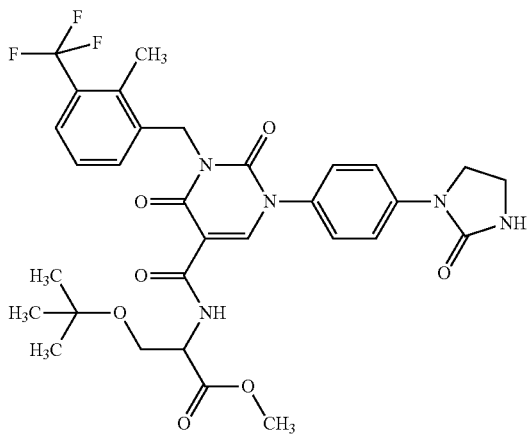 [SMILES: COC(=O)C(COC(C)(C)C)NC(=O)c1cn(-c2ccc(N3CCNC3=O)cc2)c(=O)n(Cc2cccc(C(F)(F)F)c2C)c1=O]

150 mg (0.31 mmol) of 3-[2-methyl-3-(trifluoromethyl)benzyl]-2,4-dioxo-1-[4-(2-oxoimidazolidin-1-yl)phenyl]-1,2,3,4-tetrahydropyrimidine-5-carboxylic acid from Example 25A were initially charged in 3.75 ml of dichloromethane. 53.8 mg (0.31 mmol) of methyl O-tert-butyl-L-serinate, 98.6 mg (0.31 mmol) of TBTU and 155 mg (1.54 mmol) of 4-methylmorpholine were added and the mixture was stirred at RT for 22 h. The reaction mixture was then concentrated on a rotary evaporator and the residue was purified by preparative HPLC (Method 9). This gave 151 mg (75% of theory) of the title compound.

LC-MS (Method 1): $R_t$=1.22 min; MS (ESIpos): m/z=646 (M+H)$^+$.

$^1$H-NMR (400 MHz, DMSO-d$_6$): δ=1.09 (s, 9H), 2.55 (s, 3H), 3.40-3.48 (m, 2H), 3.52-3.60 (m, 1H), 3.62 (s, 3H), 3.73-3.80 (m, 1H), 3.85-3.92 (m, 2H), 4.65-4.72 (m, 1H), 5.12 (s, 2H), 7.10 (s, 1H), 7.35 (t, 1H), 7.42 (d, 1H), 7.48 (d, 2H), 7.60 (d, 1H), 7.70 (d, 2H), 8.32 (s, 1H) 9.30 (d, 1H).

Example 61

N-({3-[2-Methyl-3-(trifluoromethyl)benzyl]-2,4-dioxo-1-[4-(2-oxoimidazolidin-1-yl)phenyl]-1,2,3,4-tetrahydropyrimidin-5-yl}carbonyl)serine

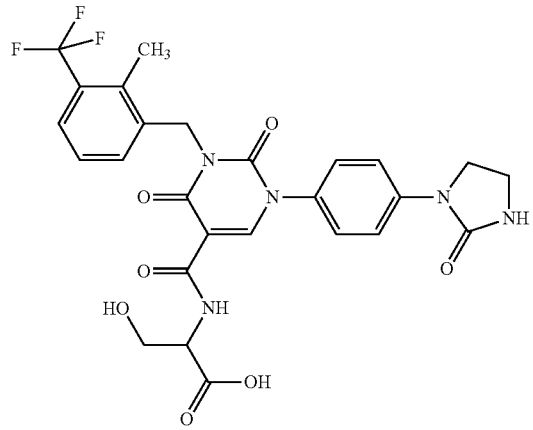 [SMILES: Cc1c(Cn2c(=O)c(C(=O)NC(CO)C(=O)O)cn(-c3ccc(N4CCNC4=O)cc3)c2=O)cccc1C(F)(F)F]

117 mg (0.181 mmol) of methyl O-tert-butyl-N-({3-[2-methyl-3-(trifluoromethyl)benzyl]-2,4-dioxo-1-[4-(2-oxoimidazolidin-1-yl)phenyl]-1,2,3,4-tetrahydropyrimidin-5-yl}carbonyl)-L-serinate from Example 60 were dissolved in a mixture of 2 ml of glacial acetic acid, 1 ml of conc. hydrochloric acid and 1 ml of water, and the mixture was then stirred at 60° C. for 4 h. After cooling to RT, the mixture was diluted with 50 ml of water. After a few minutes, the precipitate was filtered off with suction, washed with water and dried under high vacuum. The crude product was purified by preparative HPLC (Method 10). This gave 39 mg (37% of theory) of the title compound.

LC-MS (Method 4): $R_t$=1.96 min; MS (ESIpos): m/z=576 (M+H)$^+$.

$^1$H-NMR (400 MHz, DMSO-d$_6$): δ=2.55 (s, 3H), 3.38-3.48 (m, 2H), 3.62-3.69 (m, 1H), 3.80-3.85 (m, 1H), 3.85-3.92 (m, 2H), 4.41-4.45 (m, 1H), 5.12 (s, 2H), 7.10 (s, 1H), 7.31-7.41 (m, 2H), 7.45 (d, 2H), 7.60 (d, 1H), 7.70 (d, 2H), 8.32 (s, 1H) 12.30 (br. s, 1H).

Example 62

N-Cyano-1-(1,3-dimethyl-2-oxo-2,3-dihydro-1H-benzimidazol-5-yl)-2,4-dioxo-3-[(1R)-4-(trifluoromethyl)-2,3-dihydro-1H-inden-1-yl]-1,2,3,4-tetrahydropyrimidine-5-carboxamide (R Enantiomer)

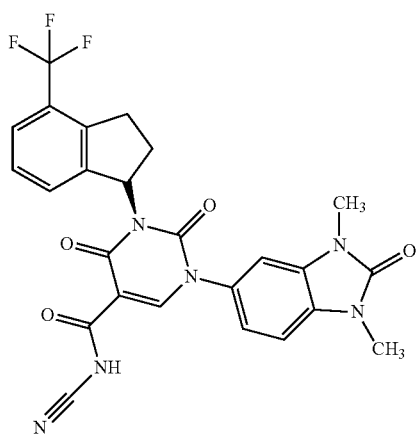

100 mg (0.2 mmol) of 1-(1,3-dimethyl-2-oxo-2,3-dihydro-1H-benzimidazol-5-yl)-2,4-dioxo-3-[(1R)-4-(trifluoromethyl)-2,3-dihydro-1H-inden-1-yl]-1,2,3,4-tetrahydropyrimidine-5-carboxylic acid (R enantiomer) from Example 23A, 9.2 mg (0.22 mmol) of cyanamide, 45.4 mg (0.22 mmol) of 1,3-dicyclohexylcarbodiimide and 26.9 mg (0.22 mmol) of 4-dimethylaminopyridine in 4 ml of dichloromethane were stirred at RT overnight. The reaction solution was diluted with 20 ml of dichloromethane and washed successively twice with 10 ml of 1N aqueous hydrochloric acid, then with 10 ml of water and a saturated aqueous sodium bicarbonate solution. The organic phase was concentrated, dissolved in a acetonitrile/DMSO and separated by preparative HPLC (Method 7).

This gave 26.4 mg (25% of theory) of the title compound.

LC/MS (Method 1): $R_t$=1.03 min, m/z=425 (M+H)$^+$ $^1$H-NMR (400 MHz, CD$_2$Cl$_2$): δ [ppm]=1.41-1.66 (m, 1H), 2.36-2.52 (m, 1H), 2.65 (dtd, 1H), 3.10-3.23 (m, 1H), 3.39 (s, 3H), 3.41 (s, 3H), 3.47 (dd, 1H), 6.63 (br. s, 1H), 6.88-7.17 (m, 3H), 7.27-7.39 (m, 2H), 7.43-7.64 (m, 1H), 8.46-8.83 (m, 1H).

Example 63

N-Cyano-1-(3-methyl-2-oxo-2,3-dihydro-1,3-benzoxazol-6-yl)-2,4-dioxo-3-[(1R)-4-(trifluoromethyl)-2,3-dihydro-1H-inden-1-yl]-1,2,3,4-tetrahydropyrimidine-5-carboxamide (R Enantiomer)

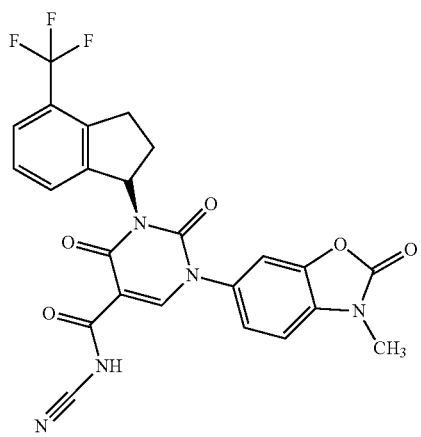

100 mg (0.21 mmol) of 1-(3-methyl-2-oxo-2,3-dihydro-1,3-benzoxazol-6-yl)-2,4-dioxo-3-[(1R)-4-(trifluoromethyl)-2,3-dihydro-1H-inden-1-yl]-1,2,3,4-tetrahydropyrimidine-5-carboxylic acid (R enantiomer) from Example 22A, 9.5 mg (0.23 mmol) of cyanamide, 46.6 mg (0.23 mmol) of 1,3-dicyclohexylcarbodiimide and 27.6 mg (0.23 mmol) of 4-dimethylaminopyridine in 4 ml of dichloromethane were stirred at RT overnight. The reaction mixture was concentrated and the residue was dissolved in DMSO and separated by preparative HPLC (Method 6). This gave 54 mg (51% of theory) of the title compound.

LC/MS (Method 1): $R_t$=1.1 min., m/z=512 (M+H)$^+$ $^1$H-NMR (400 MHz, CD$_2$Cl$_2$): δ [ppm]=2.23-2.41 (m, 1H), 2.49-2.67 (m, 1H), 3.00-3.18 (m, 1H), 3.34 (s, 3H), 3.35-3.45 (m, 1H), 6.40-6.64 (m, 1H), 6.97-7.04 (m, 1H), 7.08-7.19 (m, 2H), 7.21-7.29 (m, 2H), 7.45 (t, 1H), 8.54 (s, 1H), 10.67-10.99 (m, 1H).

Example 64

1-(3-Methyl-2-oxo-2,3-dihydro-1,3-benzoxazol-6-yl)-2,4-dioxo-3-[(1R)-4-(trifluoromethyl)-2,3-dihydro-1H-inden-1-yl]-N-[(trifluoromethyl)sulfonyl]-1,2,3,4-tetrahydropyrimidine-5-carboxamide (R Enantiomer)

Example 65

2,4-Dioxo-1-[4-(2-oxo-1,3-oxazolidin-3-yl)phenyl]-3-[(1R)-4-(trifluoromethyl)-2,3-dihydro-1H-inden-1-yl]-N-[(trifluoromethyl)sulfonyl]-1,2,3,4-tetrahydropyrimidine-5-carboxamide (R Enantiomer)

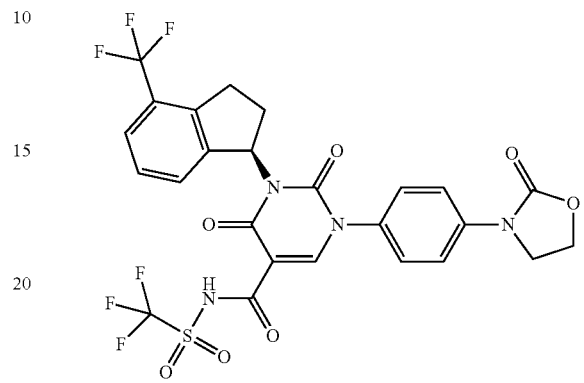

Analogously to Example 64, the title compound was prepared from 160 mg (0.32 mmol) of the compound from Example 44A and 57 mg (0.38 mmol) of trifluoromethanesulfonamide. This gave 42 mg (20% of theory).

LC-MS (Method 1): $R_t$=1.06 min; ES(neg): m/z=631 (M−H)⁻.

$^1$H-NMR (400 MHz, $CD_2Cl_2$): δ [ppm]=2.37-2.53 (m, 1H), 2.65 (dtd, 1H), 3.11-3.24 (m, 1H), 3.42-3.57 (m, 1H), 4.06 (t, 2H), 4.49 (t, 2H), 6.58-6.70 (m, 1H), 7.28-7.41 (m, 4H), 7.50-7.58 (m, 1H), 7.71 (d, 2H), 8.61 (s, 1H), 12.10 (br. s., 1H).

B. ASSESSMENT OF PHARMACOLOGICAL EFFICACY

The pharmacological activity of the compounds according to the invention can be shown in the assays described below:

Abbreviations:

| | |
|---|---|
| Abz-HPFHL-Lys(Dnp)-$NH_2$ | 1-[N-(3-aminobenzoyl)histidylprolylphenylalanylhistidylleucyl-$N^6$-(2,4-dinitrophenyl)lysine |
| AMC | 7-amido-4-methylcoumarin |
| BNP | brain natriuretic peptide |
| BSA | bovine serum albumin |
| CHAPS | 3-[(3-cholamidopropyl)dimethylammonio]-1-propanesulfonate |
| HEPES | N-(2-hydroxyethyl)piperazin-N'-2-ethanesulfonic acid |
| IC | inhibition concentration |
| MeOSuc | methoxysuccinyl |
| NADP | nicotinamide adenine dinucleotide phosphate |
| PBS | phosphate-buffered saline solution |
| PEG | polyethylene glycol |
| v/v | volume to volume ratio (of a solution) |
| w/v | weight to volume ratio (of a solution) |

B-1. Enzymatic Chymase Assay

The enzyme source used is recombinant human chymase (expressed in HEK293 cells) or chymase purified from hamsters' tongues. The substrate used for chymase is Abz-HPFHL-Lys(Dnp)-$NH_2$. For the assay, 1 μl of a 50-fold concentrated solution of test substance in DMSO, 24 μl of enzyme solution (dilution 1:80 000 human or 1:4000 ham-

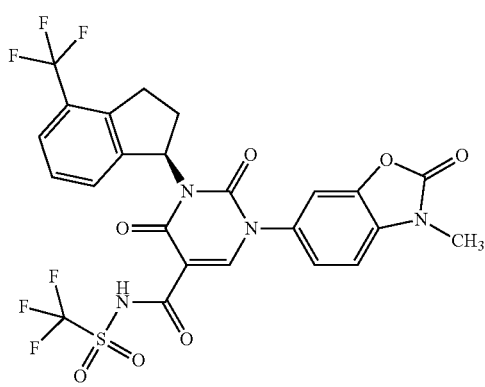 [SMILES: Cn1c(=O)oc2cc(-n3cc(C(=O)NS(=O)(=O)C(F)(F)F)c(=O)n([C@@H]4CCc5c4cccc5C(F)(F)F)c3=O)ccc21]

At RT, 59 mg (0.39 mmol) of trifluoromethanesulfonamide were added to a mixture of 160 mg (0.33 mmol) of the compound from Example 22A, 102 mg (049 mmol) of 1,3-dicyclohexylcarbodiimide and 44 mg (0.36 mmol) of 4-dimethylaminopyridine in 10.3 ml of dichloromethane. The reaction mixture was stirred at RT overnight. The mixture was diluted with ethyl acetate and washed twice with 1M aqueous hydrochloric acid and once with a saturated aqueous sodium chloride solution. The organic phase was dried over sodium sulfate and concentrated on a rotary evaporator. The crude product obtained was purified by preparative HPLC (Method 20). This gave 52 mg (24% of theory) of the title compound.

LC-MS (Method 1): $R_t$=1.15 min; m/z=619 (M+H)⁺.

$^1$H-NMR (400 MHz, $CD_2Cl_2$): δ [ppm]=2.38-2.52 (m, 1H), 2.65 (dtd, 1H), 3.11-3.25 (m, 1H), 3.41 (s, 3H), 3.44-3.56 (m, 1H), 6.58-6.70 (m, 1H), 7.05-7.12 (m, 1H), 7.17 (d, 1H), 7.23 (br. s., 1H), 7.29-7.38 (m, 2H), 7.51-7.58 (m, 1H), 8.61 (s, 1H), 12.07 (br. s., 1H).

ster) and 25 μl of substrate solution (final concentration 10 μM) in assay buffer (Tris 50 mM (pH 7.5), sodium chloride 150 mM, BSA 0.10%, Chaps 0.10%, glutathione 1 mM, EDTA 1 mM) are combined in a white 384-hole microtitre plate (Greiner Bio-One, Frickenhausen, Germany). The reaction is incubated at 32 degrees for 60 min and the fluorescence emission at 465 nm after excitation at 340 nm is measured in a fluorescence reader, for example Tecan Ultra (Tecan, Mainnedorf, Switzerland).

One test compound is tested on the same microtitre plate in 10 different concentrations from 30 μM to 1 nM in a double determination. The data are normalized (enzyme reaction without inhibitor=0% inhibition, all assay components without enzyme=100% inhibition) and $IC_{50}$ values are calculated using in-house software. Compounds in the context of the invention which were tested in this assay inhibited chymase activity with an $IC_{50}$ of less than 10 μM.

$IC_{50}$ values representative of the compounds of the invention are shown in Table 1 below:

| Example No.: | hamster chymase $IC_{50}$ [nM] |
|---|---|
| 1 | 4.7 |
| 2 | 18 |
| 3 | 8.7 |
| 4 | 48 |
| 5 | 29 |
| 6 | 6.6 |
| 7 | 37 |
| 8 | 53 |
| 9 | 35 |
| 12 | 7.6 |
| 13 | 1.8 |
| 14 | 3.5 |
| 15 | 2.8 |
| 16 | 4.6 |
| 17 | 2.8 |
| 18 | 42 |
| 19 | 5.8 |
| 20 | 22 |
| 21 | 32 |
| 22 | 7.3 |
| 23 | 5.5 |
| 24 | 85 |
| 25 | 30 |
| 26 | 44 |
| 27 | 130 |
| 29 | 13 |
| 30 | 3.5 |
| 31 | 520 |
| 32 | 3.1 |
| 33 | 4.9 |
| 34 | 55 |
| 35 | 36 |
| 36 | 19 |
| 37 | 76 |
| 38 | 8.1 |
| 39 | 16 |
| 40 | 12 |
| 41 | 12 |
| 42 | 9.8 |
| 43 | 8.1 |
| 45 | 25 |
| 47 | 4.2 |
| 48 | 54 |
| 49 | 3.6 |
| 50 | 39 |
| 51 | 3 |
| 52 | 94 |
| 53 | 180 |
| 54 | 63.5 |
| 55 | 238 |
| 57 | 19 |
| 59 | 914 |
| 60 | 1590 |

-continued

| Example No.: | hamster chymase $IC_{50}$ [nM] |
|---|---|
| 61 | 17 |
| 62 | 5.6 |
| 63 | 2.6 |

B-2. Measurement of Contraction on Isolated Aorta Rings from Hamsters

Male Syrian hamsters (120-150 g) were euthanized with carbon dioxide. The aorta was prepared and placed into ice-cold Krebs-Henseleit buffer. (Composition in mmol/l: sodium chloride 112, potassium chloride 5.9, calcium chloride 2.0, magnesium chloride 1.2, sodium dihydrogenphosphate 1.2, sodium hydrogencarbonate 25, glucose 11.5). The aorta was cut into rings of length 2 mm, transferred to an organ bath filled with 5 ml of Krebs-Henseleit buffer and connected to a myograph (DMT, Denmark). The buffer was warmed to 37° C. and sparged with 95% oxygen, 5% carbon dioxide. In order to measure the isometric muscle contraction, the aorta rings were mounted between two hooks. One of the hooks was connected to a pressure transducer. The second hook was movable and allowed precise setting of the initial load by a protocol described by Mulvany and Halpern (Circulation Research 1977; 41:19-26).

Before each experiment, the responsiveness of the preparation was tested by adding potassium-containing Krebs-Henseleit solution (50 mmol/l KCl). A synthetic peptide, angiotensin 1-18, was used to induce contraction of the aorta rings. The angiotensin 1-18 is converted to angiotensin II independently of ACE. Subsequently, the aorta rings were incubated with the test substance for 20 min and the contraction measurement was repeated. Chymase inhibition is shown as a reduction in the contraction induced by angiotensin 1-18.

B-3. Isoprenaline-Induced Cardiac Fibrosis Model in Hamsters

For the experiments, male Syrian hamsters having a body weight of 130-160 g were used. Cardiac hypertrophy and cardiac fibrosis were induced by a daily subcutaneous injection of 20 mg/kg isoprenaline over 7 days. The test substance was administered orally to the animals 2 hours before the injection of the isoprenaline. Control groups were treated subcutaneously and orally with solvents in a corresponding manner. At the end of the experiment, the hearts were removed, weighed and fixed. The fibrotic tissue on the histological sections from the hearts was marked with the aid of Sirius Red staining. Subsequently, the fibrotic area was determined by planimetry.

C. WORKING EXAMPLES FOR PHARMACEUTICAL COMPOSITIONS

The compounds of the invention can be converted to pharmaceutical formulations as follows:

Tablet:

Composition:

100 mg of the compound of the invention, 50 mg of lactose (monohydrate), 50 mg of corn starch (native), 10 mg of polyvinylpyrrolidone (PVP 25) (BASF, Ludwigshafen, Germany) and 2 mg of magnesium stearate.

Tablet weight 212 mg. Diameter 8 mm, radius of curvature 12 mm.

Production:

The mixture of compound of the invention, lactose and starch is granulated with a 5% solution (w/w) of the PVP in water. The granules are dried and then mixed with the magnesium stearate for 5 minutes. This mixture is compressed in a conventional tabletting press (see above for format of the tablet). The guide value used for the pressing is a pressing force of 15 kN.

Suspension for Oral Administration:
Composition:
1000 mg of the compound of the invention, 1000 mg of ethanol (96%), 400 mg of Rhodigel® (xanthan gum from FMC, Pennsylvania, USA) and 99 g of water.
10 ml of oral suspension correspond to a single dose of 100 mg of the compound of the invention.

Production:
The Rhodigel is suspended in ethanol; the compound of the invention is added to the suspension. The water is added while stirring. The mixture is stirred for about 6 h before swelling of the Rhodigel is complete.

Solution for Oral Administration:
Composition:
500 mg of the compound of the invention, 2.5 g of polysorbate and 97 g of polyethylene glycol 400. 20 g of oral solution correspond to a single dose of 100 mg of the compound of the invention.

Production:
The compound of the invention is suspended in the mixture of polyethylene glycol and polysorbate with stirring. The stirring operation is continued until dissolution of the compound of the invention is complete.

i.v. Solution:
The compound of the invention is dissolved in a concentration below the saturation solubility in a physiologically acceptable solvent (e.g. isotonic saline solution, glucose solution 5% and/or PEG 400 solution 30%). The solution is subjected to sterile filtration and dispensed into sterile and pyrogen-free injection vessels.

The invention claimed is:
1. A compound of the formula (I)

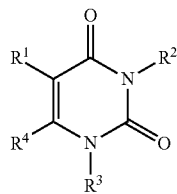

(I)

in which
$R^1$ represents a group of the formula

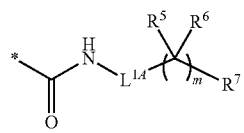

where
represents the point of attachment to the uracil group,
m represents 0 or 1,
$L^{14}$ represents a bond or $(C_1-C_4)$-alkanediyl, in which $(C_1-C_4)$-alkanediyl may be substituted by 1 to 3 substituents independently of one another selected from the group consisting of fluorine, trifluoromethyl, $(C_1-C_4)$-alkyl, $(C_3-C_7)$-cycloalkyl, hydroxy and $(C_1-C_4)$-alkoxy,
$R^5$ represents hydrogen or $(C_1-C_4)$-alkyl,
$R^6$ represents hydrogen or $(C_1-C_4)$-alkyl,
in which $(C_1-C_4)$-alkyl may be substituted by 1 or 2 substituents independently of one another selected from the group consisting of fluorine, trifluoromethyl, $(C_1-C_4)$-alkyl, hydroxy and $(C_1-C_4)$-alkoxy,
or
$R^5$ and $R^6$ together with the carbon atoms to which they are attached form a 3- to 7-membered carbocycle,
$R^7$ represents hydrogen, cyano, $(C_3-C_7)$-cycloalkyl, hydroxycarbonyl or $(C_1-C_4)$-alkoxycarbonyl,
$R^2$ represents a group of the formula

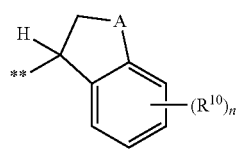

where
** represents the point of attachment to the uracil nitrogen atom,
A represents $CH_2-$, $-CH_2-CH_2-$, $-O-CH_2-\#\#$ or oxygen, in which ## represents the point of attachment to the phenyl ring,
n represents a number 0, 1 or 2,
$R^{10}$ represents hydrogen, halogen, difluoromethyl, trifluoromethyl, $(C_1-C_4)$-alkyl, difluoromethoxy, trifluoromethoxy or $(C_1-C_4)$-alkoxy,
$R^3$ represents

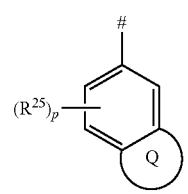

in which
\# represents the point of attachment to the uracil nitrogen atom,
the ring Q represents 5- to 7-membered heterocyclyl or 5- or 6-membered heteroaryl,
in which 5- to 7-membered heterocyclyl may be substituted by 1 to 4 substituents independently selected from the group of halogen, difluoromethyl, trifluoromethyl, trideuteromethyl, $(C_1-C_6)$-alkyl, $(C_3-C_7)$-cycloalkyl, oxo, hydroxyl, $(C_1-C_4)$-alkylcarbonyl, $(C_1-C_4)$-alkoxycarbonyl, aminocarbonyl and $(C_1-C_4)$-alkyl sulfonyl,
in which 5- or 6-membered heteroaryl may be substituted by 1 to 2 substituents independently of one another selected from the group consisting of $(C_1-C_6)$-alkyl, $(C_3-C_7)$-cycloalkyl, hydroxy, $(C_1-C_4)$-alkylcarbonyl, $(C_1-C_4)$-alkoxycarbonyl, aminocarbonyl and $(C_1-C_4)$-alkylsulfonyl, and
in which two $(C_1-C_6)$-alkyl radicals attached to a carbon atom of 5- to 7-membered heterocyclyl together with the carbon atom to which they are attached may form a 3- to 6-membered carbocycle, $R^{25}$ represents halogen, $(C_1-C_4)$-alkyl or $(C_1-C_4)$-alkoxy, p represents a number 0, 1, 2 or 3, and $R^4$ represents hydrogen, and the salts, solvates and solvates of the salts thereof.

2. The compound of claim 1, wherein $R^1$ represents a group of the formula

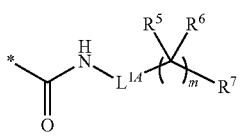

where
* represents the point of attachment to the uracil group,
m represents 0 or 1,
$L^{1A}$ represents a bond or $(C_1-C_4)$-alkanediyl,
$R^5$ represents hydrogen or $(C_1-C_4)$-alkyl,
$R^6$ represents hydrogen or $(C_1-C_4)$-alkyl,
in which $(C_1-C_4)$-alkyl may be substituted by 1 or 2 substituents independently of one another selected from the group consisting of fluorine, trifluoromethyl, $(C_1-C_4)$-alkyl, hydroxy and $(C_1-C_4)$-alkoxy, or
$R^5$ and $R^6$ together with the carbon atoms to which they are attached form a 3- to 6-membered carbocycle,
$R^7$ represents hydrogen, $(C_1-C_4)$-alkyl, cyano, $(C_3-C_6)$-cycloalkyl, hydroxycarbonyl or $(C_1-C_4)$-alkoxycarbonyl, $R^2$ represents a group of the formula

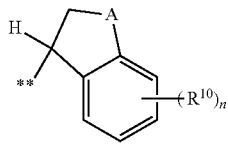

where
** represents the point of attachment to the uracil nitrogen atom,
A represents $CH_2-$ or $-CH_2-CH_2-$,
n represents a number 0, 1 or 2,
$R^{10}$ represents hydrogen, fluorine, chlorine, difluoromethyl, trifluoromethyl or methyl, $R^3$ represents a group of the formula

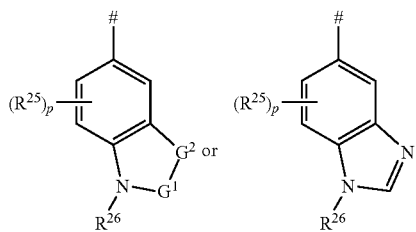

where
represents the point of attachment to the uracil nitrogen atom,
$G^1$ represents C=O or $SO_2$,
$G^2$ represents $CR^{27A}R^{27B}$, $NR^{28}$, O or S,
where
$R^{27A}$ represents hydrogen, fluorine, $(C_1-C_4)$-alkyl or hydroxy,
$R^{27B}$ represents hydrogen, fluorine, chlorine, $(C_1-C_4)$-alkyl or trifluoromethyl,
or
$R^{27A}$ and $R^{27B}$ together with the carbon atom to which they are attached form a 3- to 6-membered carbocycle,
$R^{28}$ represents hydrogen, $(C_1-C_6)$-alkyl or $(C_3-C_7)$-cycloalkyl,
$R^{25}$ represents fluorine or methyl,
p represents a number 0 or 1,
$R^{26}$ represents hydrogen, $(C_1-C_6)$-alkyl or $(C_3-C_6)$-cycloalkyl,
$R^4$ represents hydrogen,
and the salts, solvates and solvates of the salts thereof.

3. The compound of claim 1 wherein
$R^1$ represents a group of the formula

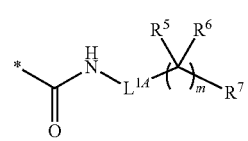

where
* represents the point of attachment to the uracil group,
m represents 0 or 1,
$L^{1A}$ represents a bond, methanediyl or ethanediyl,
$R^5$ represents hydrogen,
$R^6$ represents hydrogen or methyl,
in which methyl may be substituted by hydroxy,
or
$R^5$ and $R^6$ together with the carbon atom to which they are attached form a 3- to 5-membered carbocycle,
$R^7$ represents hydrogen, cyano, hydroxycarbonyl, methoxycarbonyl or ethoxycarbonyl,
$R^2$ represents a group of the formula

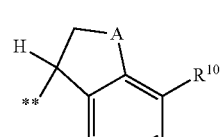

where
** represents the point of attachment to the uracil nitrogen atom,
A represents $-CH_2-$ or $-CH_2-CH_2-$,
$R^{10}$ represents chlorine or trifluoromethyl, $R^3$ represents a group of the formula

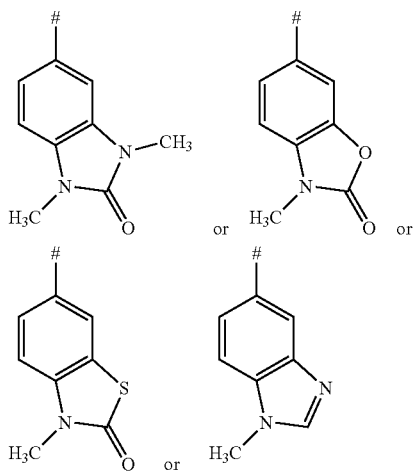

where
represents the point of attachment to the uracil nitrogen atom,
$R^4$ represents hydrogen,
and the salts, solvates and solvates of the salts thereof.

4. A method of preparing the compound of claim 1 wherein
[A] a compound of the formula (II)

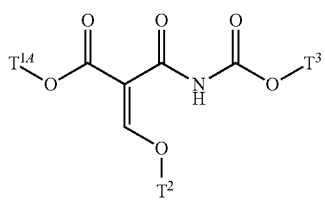

(II)

in which
$T^{1A}$ represents $(C_1-C_4)$-alkyl,
$T^2$ represents $(C_1-C_4)$-alkyl,
$T^3$ represents $(C_1-C_4)$-alkyl,
is reacted in an inert solvent, optionally in the presence of a suitable base, with a compound of the formula (III)

$R^3-NH_2$ (III), in which $R^3$ has the meaning given above
to give a compound of the formula (IV)

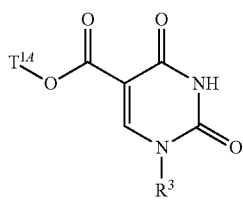

(IV)

in which $T^{1A}$ and $R^3$ each have the meanings given above, this is then reacted in an inert solvent, in the presence of a suitable base, with a compound of the formula (V)

$X^1-R^2$ (V)

in which $R^2$ has the meaning given above
and
$X^1$ represents hydroxy or a suitable leaving group, in particular chlorine, bromine or iodine,
to give a compound of the formula (VI)

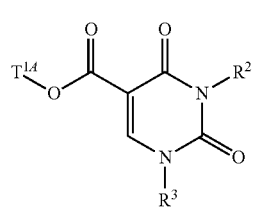

(VI)

in which $T^{1A}$, $R^2$ and $R^3$ each have the meanings given above,
the compound of the formula (VI) is then hydrolyzed in an inert solvent in the presence of a suitable acid or base to give a compound of the formula (VII)

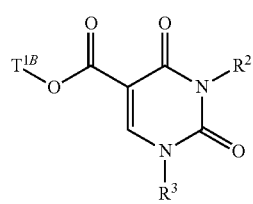

(VII)

in which $T^{1B}$ represents hydrogen and
in which $R^2$ and $R^3$ each have the meanings given above,
and then in an inert solvent with a compound of the formula (VIII)

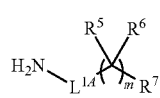

(VIII)

converted into a compound of the formula (I-1)

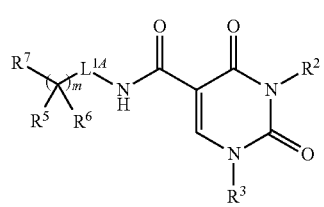

(I-1)

in which $R^2$, $R^3$, $R^5$, $R^6$, $R^7$, $L^{1A}$ and m each have the meanings given above, or

[B] a compound of the formula (IX)

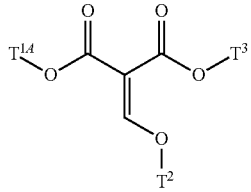
(IX)

in which $T^{1A}$, $T^2$ and $T^3$ each have the meanings mentioned above,
is converted in an inert solvent or else without solvent with a compound of the formula (III) into a compound of the formula (X)

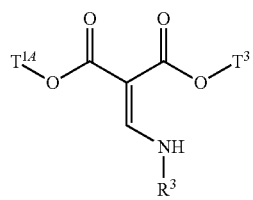
(X)

in which $R_3$, $T^{1A}$ and $T^3$ each have the meanings given above, this is subsequently reacted in an inert solvent with chlorosulfonyl isocyanate to give a compound of the formula (IV) and this is subsequently converted analogously to process [A] into a compound of the formula (I-1), or

[C] a compound of the formula (XI)

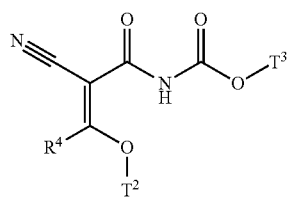
(XI)

in which
$T^2$ represents $(C_1-C_4)$-alkyl,
$T^3$ represents $(C_1-C_4)$-alkyl and
$R^4$ has the meaning given above,
is reacted in an inert solvent, optionally in the presence of a suitable base, with a compound of the formula (III) to give a compound of the formula (XII)

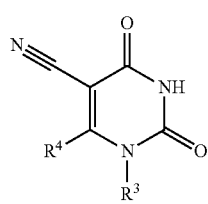
(XII)

in which $R^3$ and $R^4$ each have the meanings given above,
and this is then, by reaction with a compound of the formula (V) in an inert solvent,
if appropriate in the presence of a suitable base,
converted into a compound of the formula (I-2)

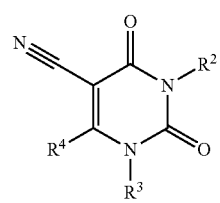
(I-2)

in which $R^2$, $R^3$ and $R^4$ each have the meanings given above, or

[D] a compound of the formula (I-2) is converted with an azide source in the presence of a catalyst in an inert solvent into a compound of the formula (I-3)

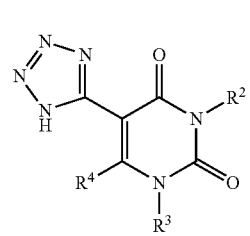
(I-3)

in which $R^2$, $R^3$ and $R^4$ each have the meanings given above, or

[E] a compound of the formula (I-2) is converted with hydroxylamine into a compound of the formula (XIII)

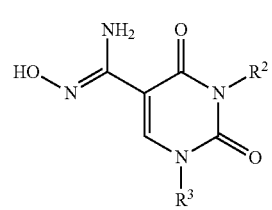
(XIII)

in which $R^2$ and $R^3$ each have the meanings given above,
and then in an inert solvent with a carbonyl donor or a thiocarbonyl donor, if appropriate in the presence of a base, to give a compound of the formula (I-4)

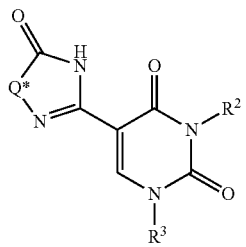
(I-4)
in which R² and R³ each have the meanings given above and in which
Q* represents oxygen or sulfur,
any protecting groups are detached and/or the compounds of the formulae (I-1), (I-2), (I-3) and (I-4) are, where appropriate, converted with the appropriate (i) solvents and/or (ii) bases or acids to the solvates, salts and/or solvates of the salts thereof.
* * * * *